(12) United States Patent
Delgoffe

US011583555B2

(10) Patent No.: US 11,583,555 B2
(45) Date of Patent: Feb. 21, 2023

(54) GENETIC RE-ENGINEERING OF IMMUNE CELLS TO IMPROVE METABOLIC FITNESS FOR IMMUNOTHERAPY

(71) Applicant: University of Pittsburgh—Of the Commonwealth System of Higher Education, Pittsburgh, PA (US)

(72) Inventor: Greg M. Delgoffe, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 436 days.

(21) Appl. No.: 16/305,181

(22) PCT Filed: Jun. 26, 2017

(86) PCT No.: PCT/US2017/039252
§ 371 (c)(1),
(2) Date: Nov. 28, 2018

(87) PCT Pub. No.: WO2017/223557
PCT Pub. Date: Dec. 28, 2017

(65) Prior Publication Data
US 2019/0350973 A1 Nov. 21, 2019

Related U.S. Application Data

(60) Provisional application No. 62/354,338, filed on Jun. 24, 2016.

(51) Int. Cl.
| | |
|---|---|
| *A61K 35/17* | (2015.01) |
| *A61P 35/00* | (2006.01) |
| *A61K 38/20* | (2006.01) |
| *A61K 45/06* | (2006.01) |
| *C12N 5/0783* | (2010.01) |
| *C12N 15/86* | (2006.01) |

(52) U.S. Cl.
CPC .......... *A61K 35/17* (2013.01); *A61K 38/2013* (2013.01); *A61K 45/06* (2013.01); *A61P 35/00* (2018.01); *C12N 5/0636* (2013.01); *C12N 15/86* (2013.01); *C12N 2501/2302* (2013.01); *C12N 2501/2307* (2013.01); *C12N 2501/2315* (2013.01)

(58) Field of Classification Search
CPC .... A61K 35/17; A61K 38/2013; A61K 45/06; A61P 35/00; C12N 5/0636; C12N 15/86
See application file for complete search history.

(56) References Cited

U.S. PATENT DOCUMENTS

2015/0283233 A1* 10/2015 Khan .................. A61K 38/20
424/192.1
2019/0031759 A1* 1/2019 Reiter ................ C07K 14/7051

FOREIGN PATENT DOCUMENTS

WO WO 2015/164594 A1 10/2015

OTHER PUBLICATIONS

Attwood, "The Babel of Bioinformatics", Science 290: 471-473, 2000 (Year: 2000).*
Skolnick et al., "From genes to protein structure and function: novel applications of computational approaches in the genomic era", Trends in Biotech. 18: 34-39, 2000 (Year: 2000).*
Sanchis-Gomar et al. "Mitochondrial biogenesis in health and disease. Molecular and therapeutic approaches", Curr Pharm Des. 2014;20(35):5619-33. (Year: 2014).*
Burns et al. "Modulation of PPAR activity via phosphorylation", Biochim Biophys Acta. Aug. 2007; 1771(8): 952-960. (Year: 2007).*
Kawalekar et al. "Distinct Signaling of Coreceptors Regulates Specific Metabolism Pathways and Impacts Memory Development in CAR T Cells", Immunity. Feb. 16, 2016;44(2):380-90. (Year: 2016).*
Rodgers et al. "Cdc2-like kinase 2 is an insulin-regulated suppressor of hepatic gluconeogenesis", Cell Metab. Jan. 2010;11(1):23-34 (Year: 2010).*
Baixauli et al., "Mitochondrial Respiration Controls Lysosomal Function during Inflammatory T Cell Responses," *Cell Metab.* 22:485-498, 2015.
Blankenstein et al., "Targeting cancer-specific mutations by T cell receptor gene therapy," *Curr Opin Immunol.* 33:112-119, 2015.
Delgoffe & Powell, "Feeding an army: the metabolism of T cells in activation, anergy, and exhaustion," *Mol Immunol.* 68:492-496, 2015.
Delgoffe, "Mitochondrial dysfunction and metabolic insufficiency underlie intratumoral T cell exhaustion," Poster presented at Keystone Symposium on Immunometabolism, Banff, Alberta, Canada, Feb. 25, 2016.
Dotti et al., "Design and Development of Therapies using Chimeric Antigen Receptor-Expressing T cells," *Immunol Rev*, 257:107-126, 2014.
Guo et al., "Chimeric Antigen Receptor-Modified T Cells for Solid Tumors: Challenges and Prospects," *J Immunol Res*. 2016:3350339, 2016 (11 pages).
Harris and Kranz, "Adoptive T Cell Therapies: A Comparison of T Cell Receptors and Chimeric Antigen Receptors," *Trends Pharmacol Sci*. 37:220-230, 2016.
Jensen & Riddell, "Designing chimeric antigen receptors to effectively and safely target tumors," *Curr Opin Immunol.* 33:9-15 2015.

(Continued)

*Primary Examiner* — Amy E Juedes
*Assistant Examiner* — Peter Johansen
(74) *Attorney, Agent, or Firm* — Klarquist Sparkman, LLP

(57) ABSTRACT

The present disclosure provides recombinant T cells that include a vector encoding one or more of peroxisome proliferator-activated receptor (PPAR) gamma coactivator 1-alpha (PGC1α), mitochondrial transcription factor A (Tfam), GA binding protein transcription factor alpha subunit (GABPA), and estrogen-related receptor alpha (ERRα). Such recombinant T cells can also include a chimeric antigen receptor (CAR) or a recombinant T cell receptor (TCR). Methods of using these recombinant T cells in cancer immunotherapy are provided. Also provided are kits and compositions that can be used with such methods.

20 Claims, 36 Drawing Sheets

Specification includes a Sequence Listing.

(56) References Cited

OTHER PUBLICATIONS

Kawalekar et al., "Distinct Signaling of Coreceptors Regulates Specific Metabolism Pathways and Impacts Memory Development in CAR T Cells," *Immunity* 44:330-390, 2016.

Lu et al., "Phosphorylation of Human TFAM in Mitochondria Impairs DNA Binding and Promotes Degradation by the AAA+ Lon Protease," *Mol. Cell* 49:121-132, 2013.

Michalek et al., "Estrogen-related receptor-α is a metabolic regulator of effector T-cell activation and differentiation," *Proc Natl Acad Sci U.S.A.* 108:18348-18353, 2011.

Morello et al.., "Mesothelin-Targeted CARs: Driving T Cells to Solid Tumors," *Cancer Discov.* 6:133-146, 2016.

Scharping et al., "The Tumor Microenvironment Represses T Cell Mitochondrial Biogenesis to Drive Intratumoral T Cell Metabolic Insufficiency and Dysfunction," *Immunity* 45:374-388, 2016.

Tremblay et al., "Phosphorylation-Dependent Sumoylation Regulates Estrogen-Related Receptor-αand -γ Transcriptional Activity Through a Synergy Control Motif," *Mol Endocrinol.* 22:570-584, 2008.

Yu et al., "Critical Requirement of GABPα for Normal T Cell Development," *J Biol Chem*. 285:10179-10188, 2010.

International Search Report and Written Opinion dated Sep. 25, 2017 for PCT/US2017/039252 (11 pages).

Fan et al., "Suppression of mitochondrial respiration through recruitment of p160 myb binding protein to PGC-1α: modulation by p38 MAPK," *Genes & Development*, 18(3): 278-289, 2004.

Kakarla et al., "Antitumor Effects of Chimeric Receptor Engineered Human T Cells Directed to Tumor Stroma," *Mol. Ther.* 21(8): 1611-1620, 2013.

Liu et al., "Targeting PD-L1 in non-small cell lung cancer using CAR T cells," *Oncogenesis*, 9(8): pp. 1-11, 2020.

Min et al., "c-Met specific CAR-T cells as a targeted therapy for non-small cell lung cancer cell A549," *Bioengineered*, 13(4): 9232-9248, 2022.

Wei et al., "PSCA and MUC1 in non-small-cell lung cancer as targets of chimeric antigen receptor T cells," *Oncoimmunology*, 6(3): e128,-1722, 11 pages, 2017.

\* cited by examiner

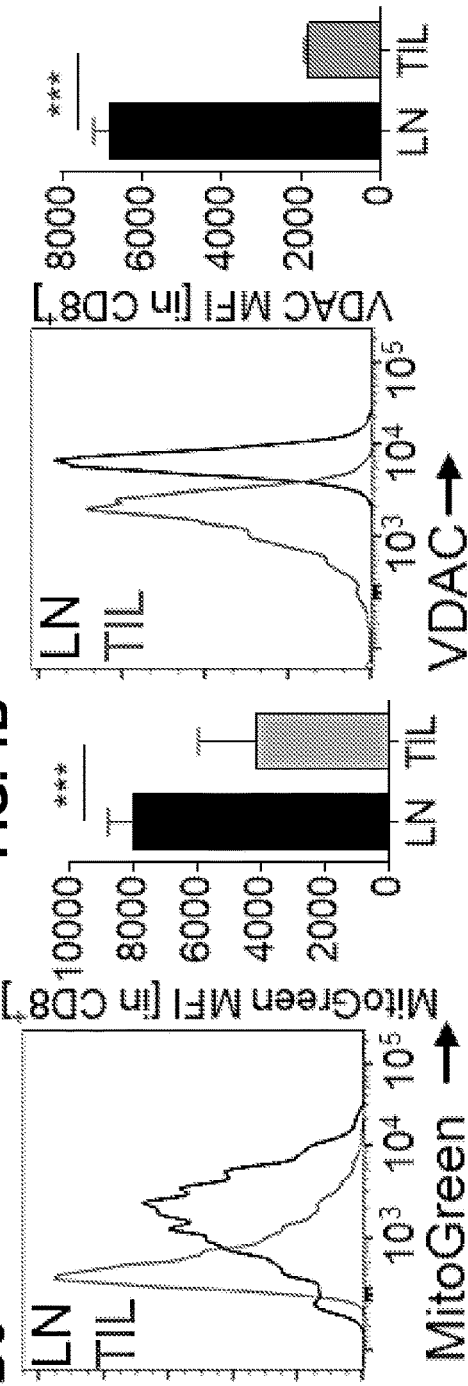
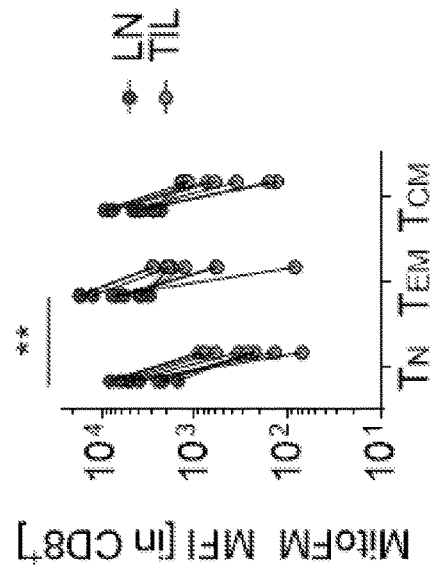
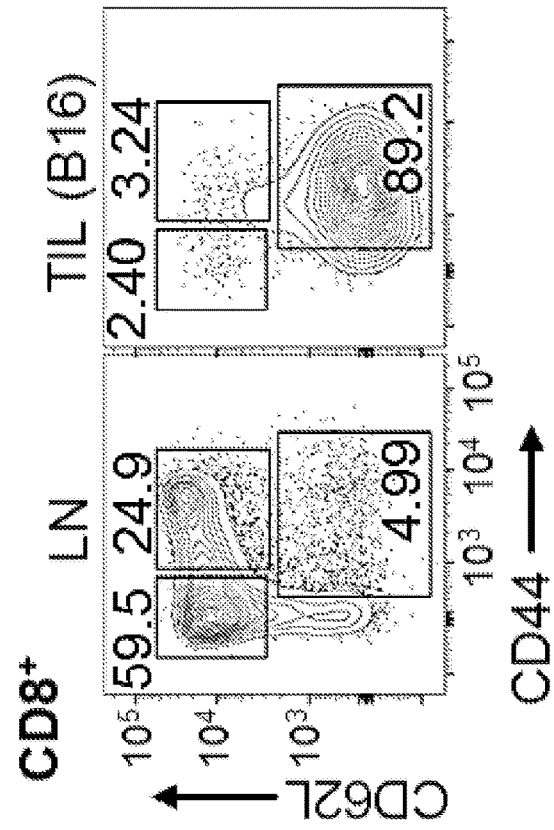
FIG. 1B
FIG. 1C

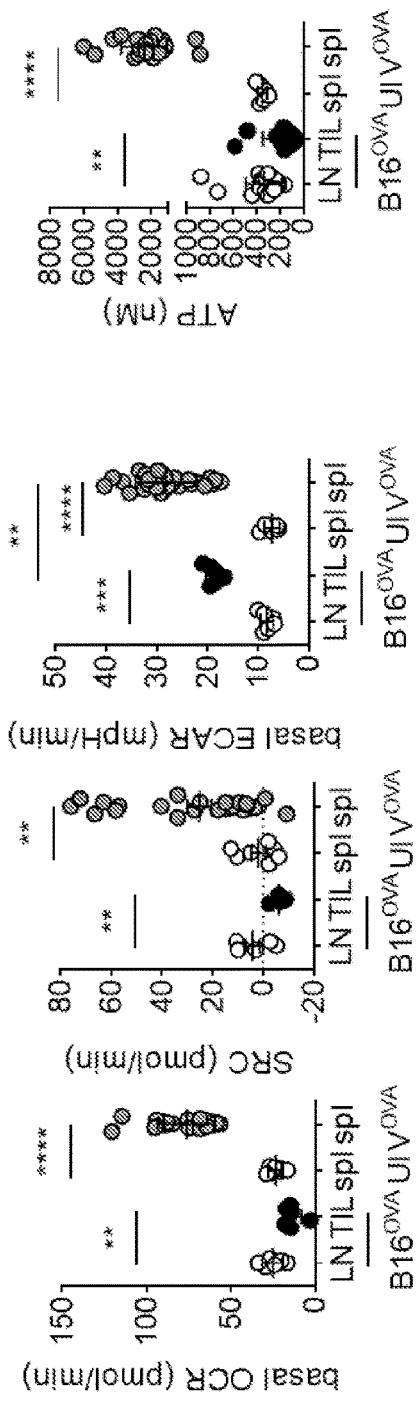
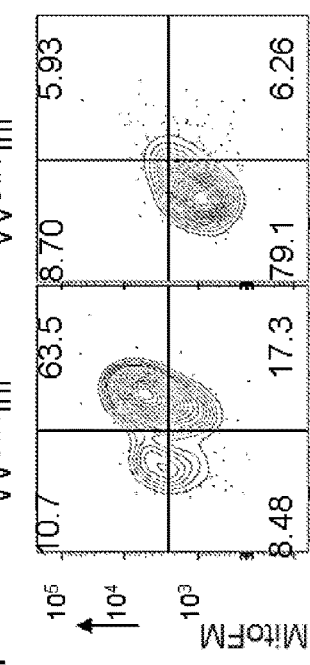
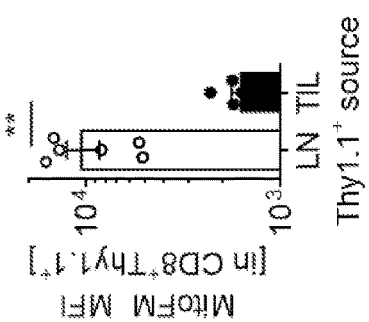

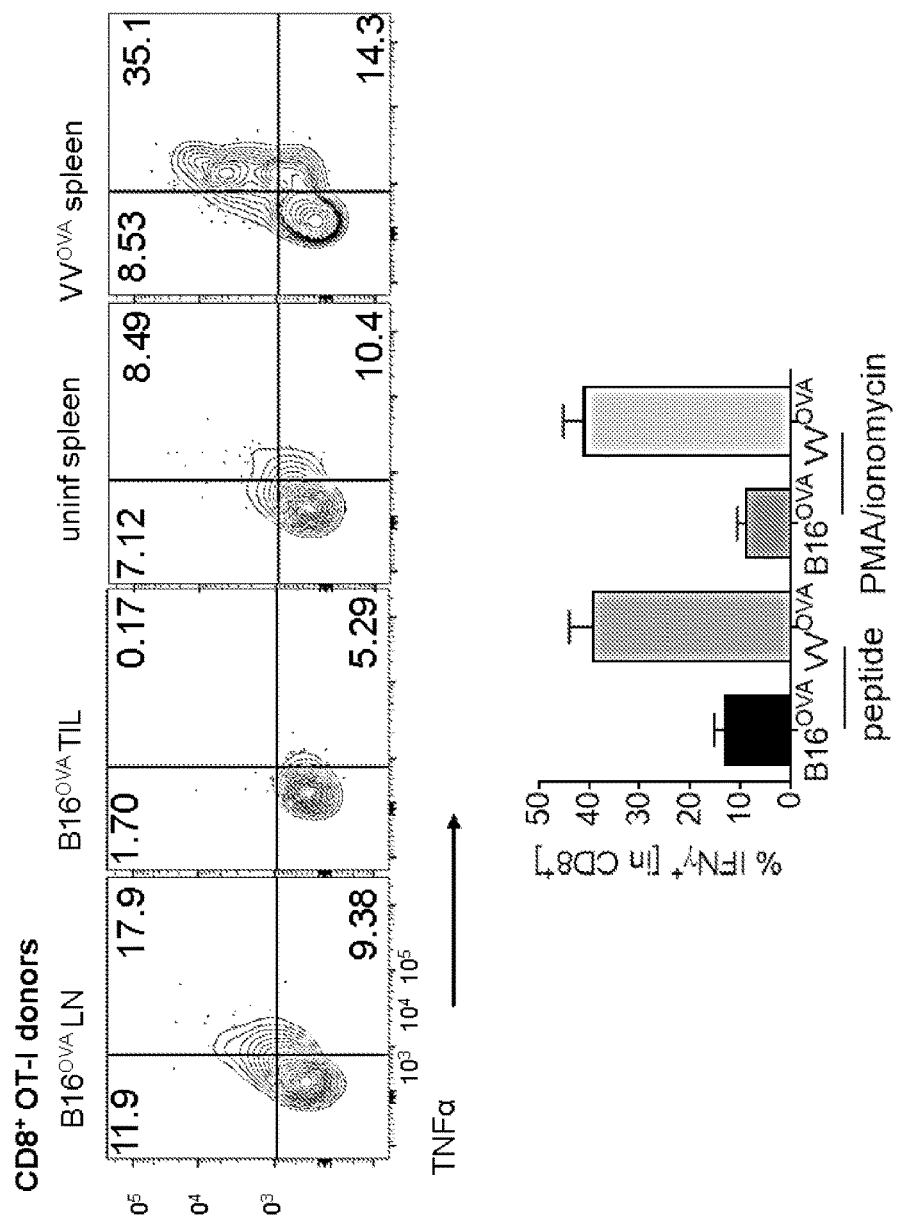
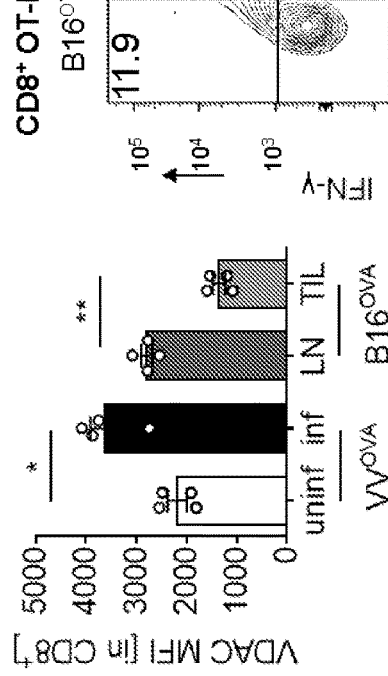
FIG. 4A
FIG. 4B

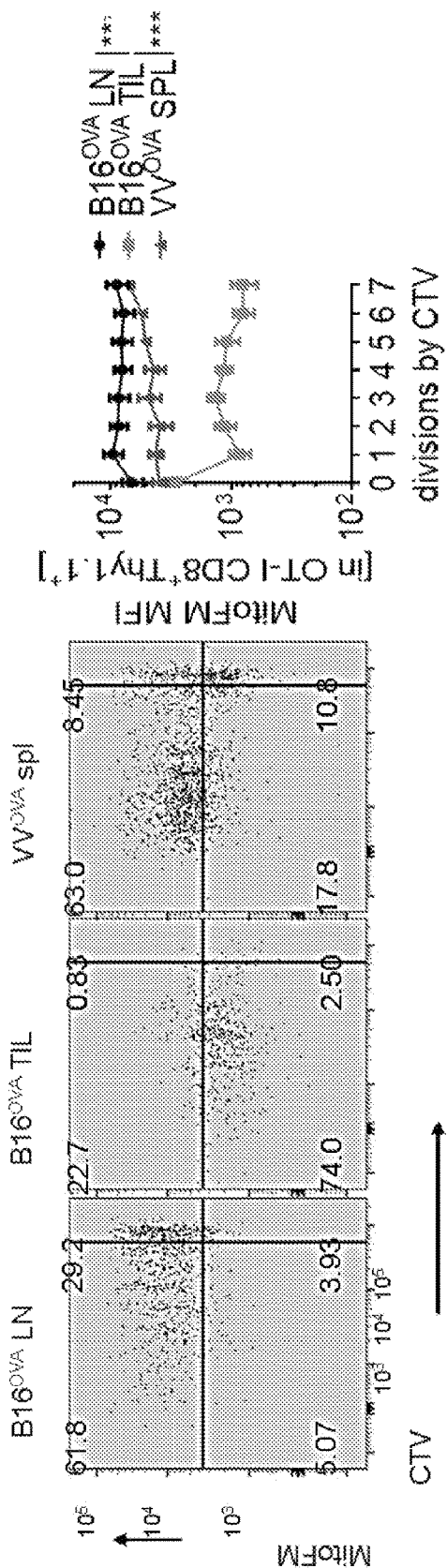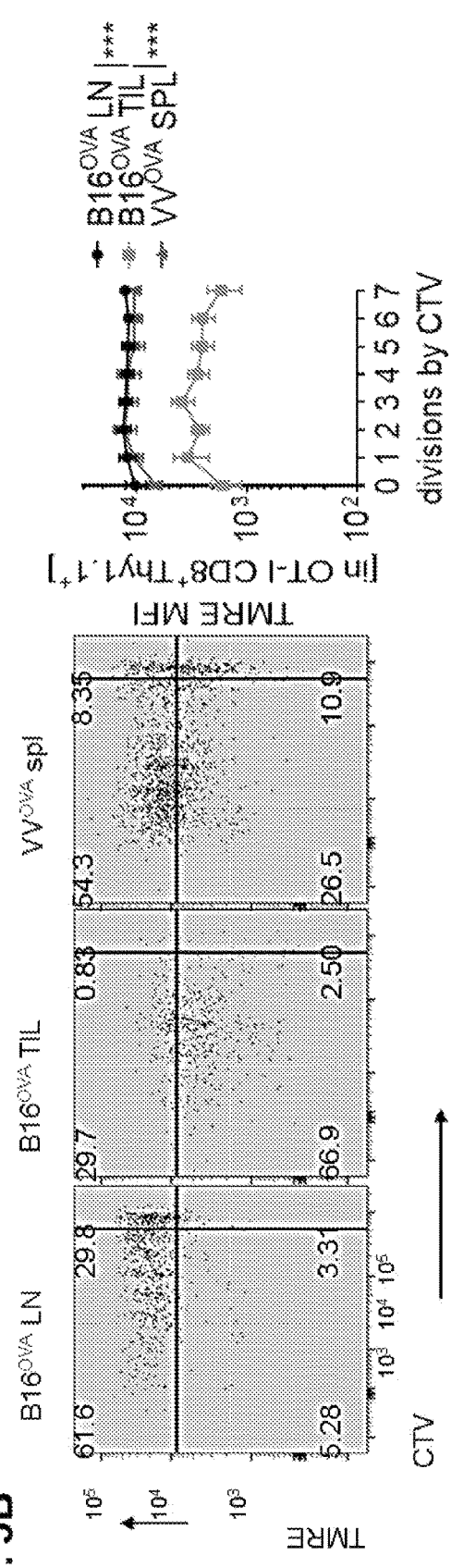
FIG. 5A
FIG. 5B

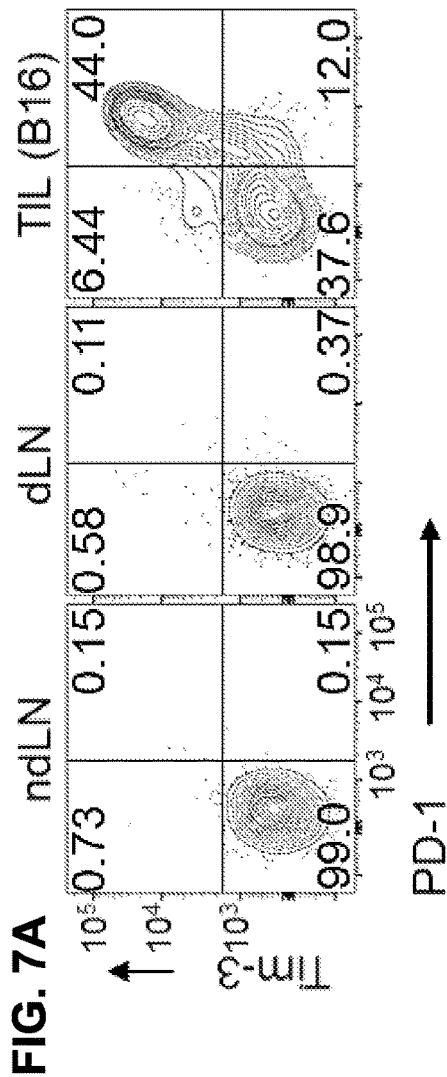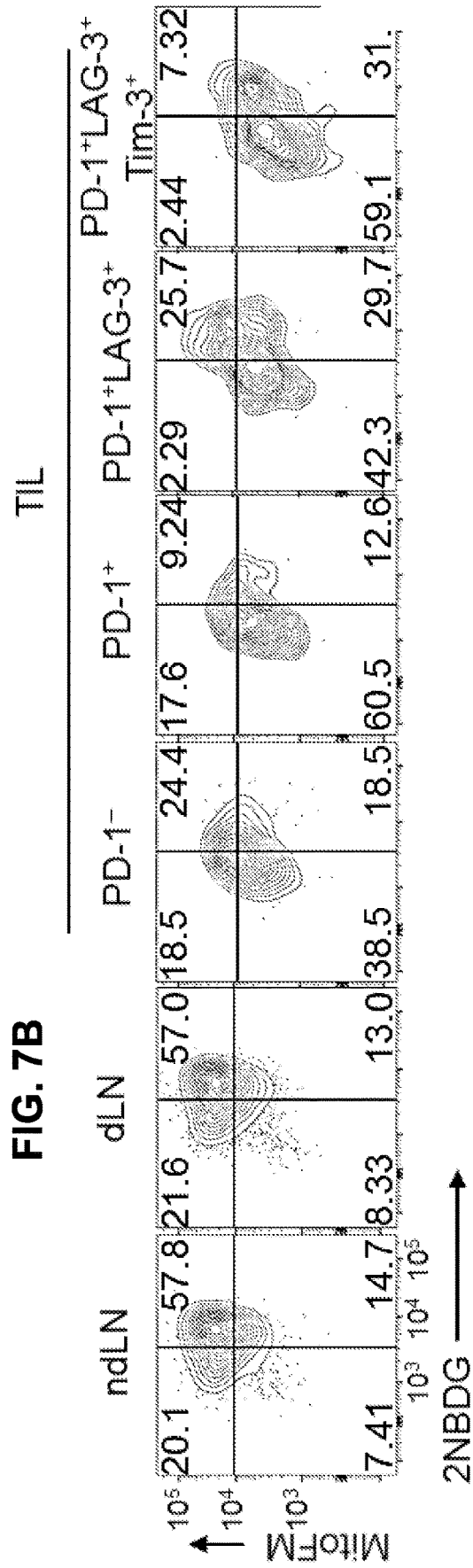
FIG. 7A
FIG. 7B

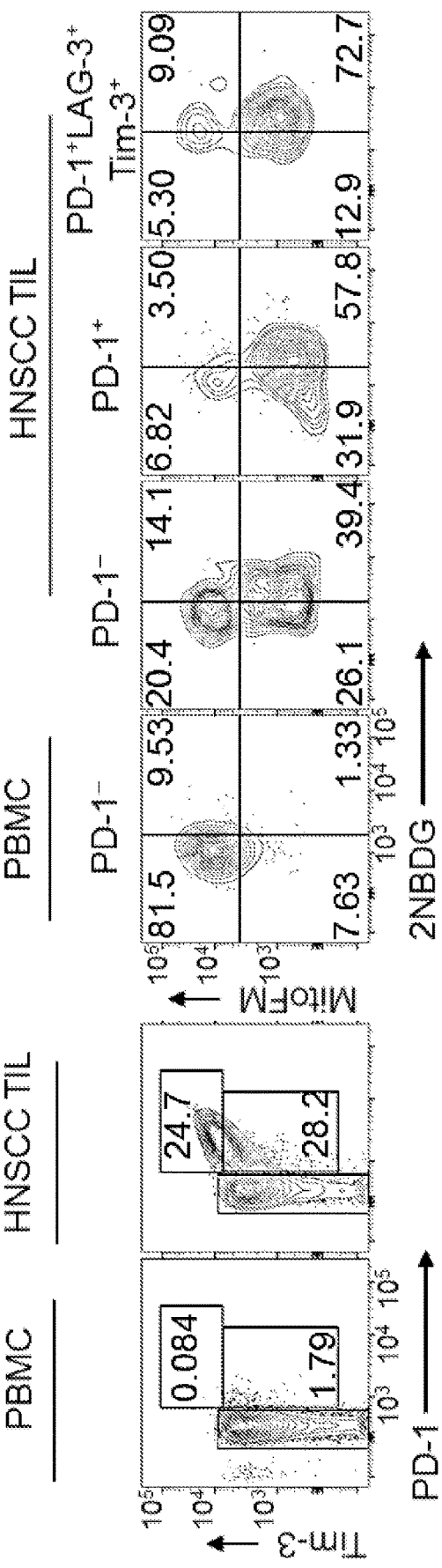

FIG. 9A Day 14 B16 melanoma

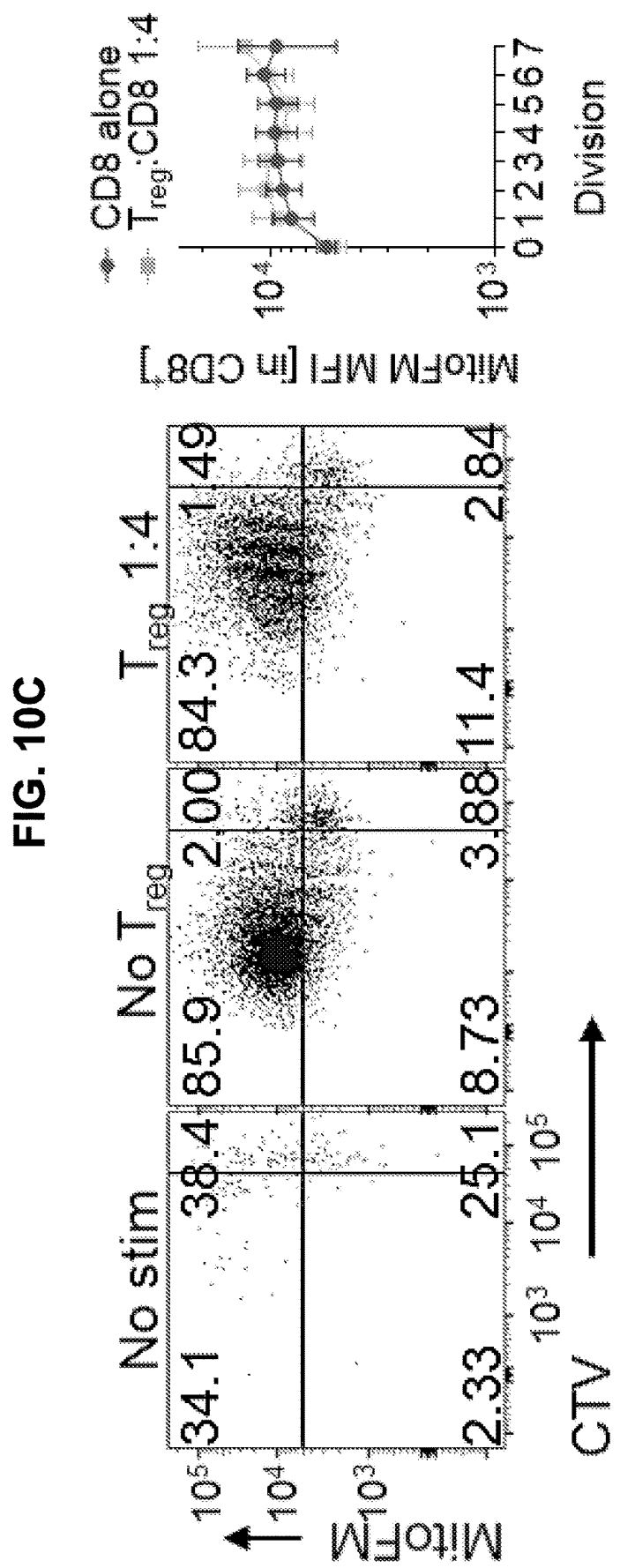

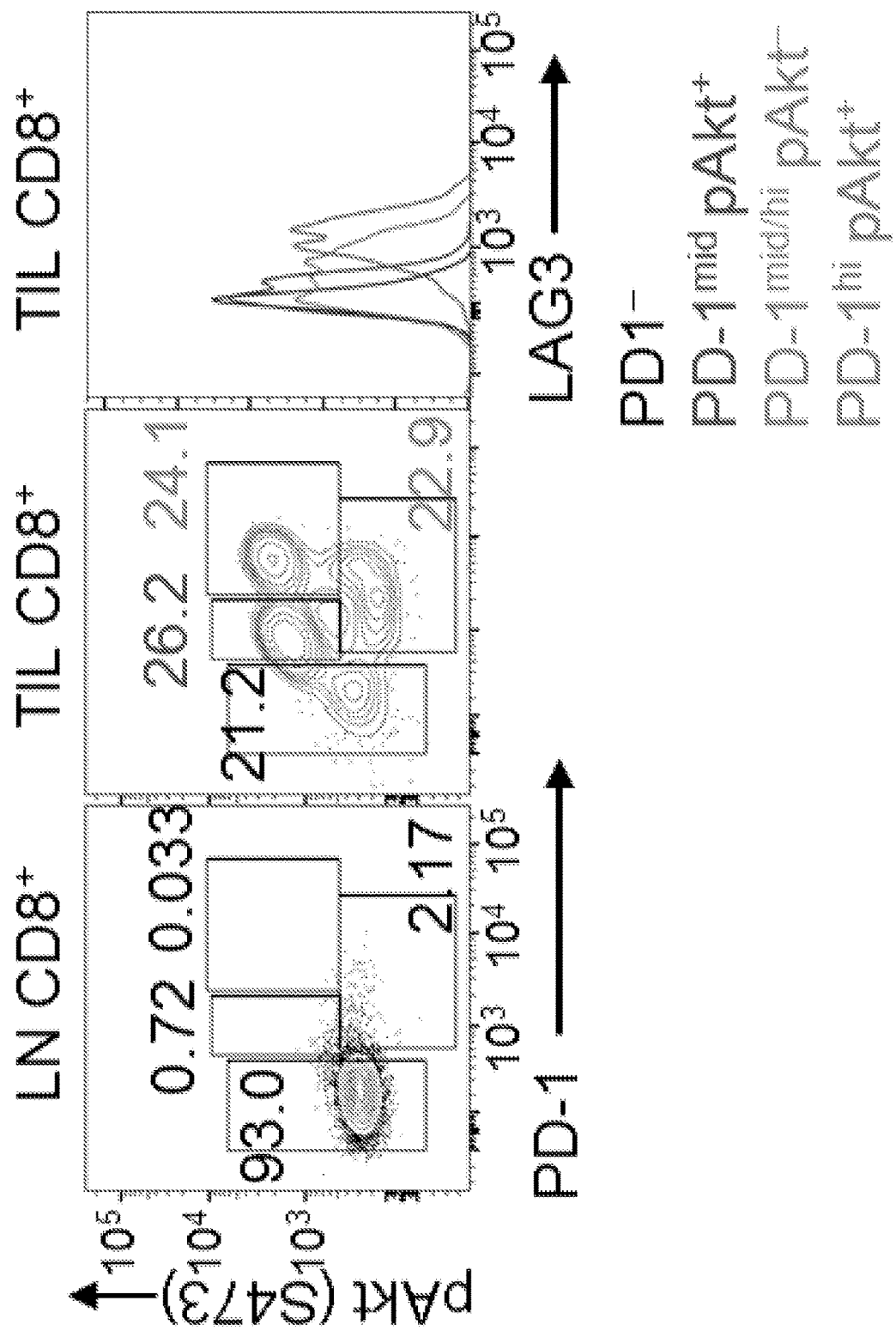

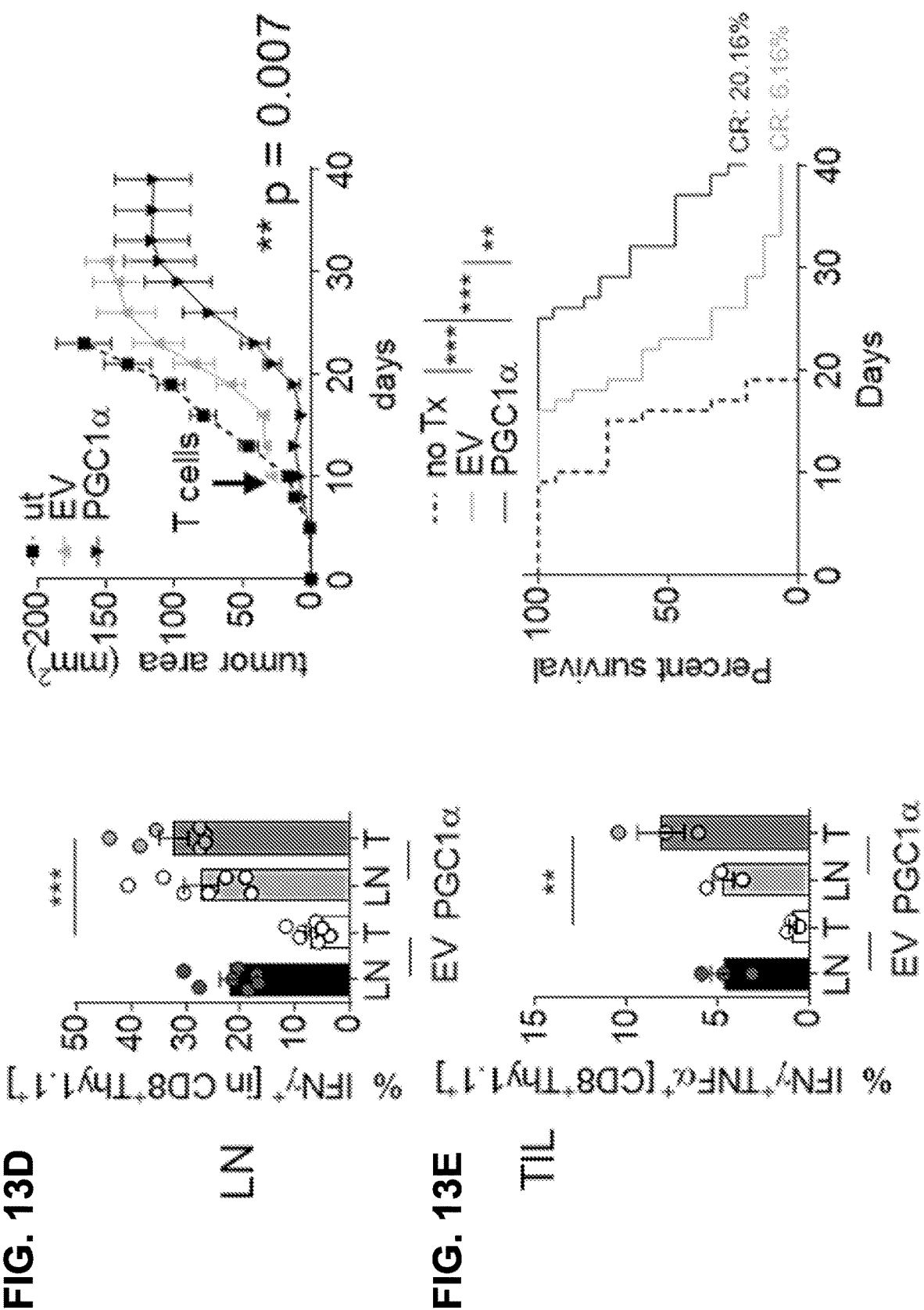

SEQUENCE LISTING

```
<160> NUMBER OF SEQ ID NOS: 9

<210> SEQ ID NO 1
<211> LENGTH: 2284
<212> TYPE: DNA
<213> ORGANISM: Homo sapiens
<220> FEATURE:
<221> NAME/KEY: CDS
<222> LOCATION: (222)..(1493)

<400> SEQUENCE: 1
gctggaggaa gcggagtagg aagcggccgc gatgtcctttt tgtgtcctac aagcagccgg      60
cggcgccgcc gagtgagggg acgcggcgcg gtggggcggc gcggcccgag gaggcggcgg     120 aggagggggcc gcccgcggcc cccggctcac tccggcactc cgggccgctc ggcccccatg     180
cctgcccgac cgcgctgccg gagccccagg tgaccagcgc c atg tcc agc cag gtg     236
                                              Met Ser Ser Gln Val
                                                1               5 gtg ggc att gag cct ctc tac atc aag gca gag ccg gcc agc cct gac        284
Val Gly Ile Glu Pro Leu Tyr Ile Lys Ala Glu Pro Ala Ser Pro Asp
             10                  15                  20 agt cca aag ggt tcc tcg gag aca gag acc gag cct cct gtg gcc ctg        332
Ser Pro Lys Gly Ser Ser Glu Thr Glu Thr Glu Pro Pro Val Ala Leu
         25                  30                  35 gcc cct ggt cca gct ccc act cgc tgc ctc cca ggc cac aag gaa gag        380
Ala Pro Gly Pro Ala Pro Thr Arg Cys Leu Pro Gly His Lys Glu Glu
     40                  45                  50 gag gat ggg gag ggg gct ggg cct ggc gag cag ggc ggt ggg aag ctg        428
Glu Asp Gly Glu Gly Ala Gly Pro Gly Glu Gln Gly Gly Gly Lys Leu
 55                  60                  65 gtg ctc agc tcc ctg ccc aag cgc ctc tgc ctg gtc tgt ggg gac gtg        476
Val Leu Ser Ser Leu Pro Lys Arg Leu Cys Leu Val Cys Gly Asp Val
 70                  75                  80                  85 gcc tcc ggc tac cac tat ggt gtg gca tcc tgt gag gcc tgc aaa gcc        524
Ala Ser Gly Tyr His Tyr Gly Val Ala Ser Cys Glu Ala Cys Lys Ala
                 90                  95                 100
```

```
ttc ttc aag agg acc atc cag ggg agc atc gag tac agc tgt ccg gcc      572
Phe Phe Lys Arg Thr Ile Gln Gly Ser Ile Glu Tyr Ser Cys Pro Ala
        105                 110                 115 tcc aac gag tgt gag atc acc aag cgg aga cgc aag gcc tgc cag gcc      620
Ser Asn Glu Cys Glu Ile Thr Lys Arg Arg Arg Lys Ala Cys Gln Ala
        120                 125                 130 tgc cgc ttc acc aag tgc ctg cgg gtg ggc atg ctc aag gag gga gtg      668
Cys Arg Phe Thr Lys Cys Leu Arg Val Gly Met Leu Lys Glu Gly Val
        135                 140                 145 cgc ctg gac cgc gtc cgg ggt ggg cgg cag aag tac aag cgg cgg ccg      716
Arg Leu Asp Arg Val Arg Gly Gly Arg Gln Lys Tyr Lys Arg Arg Pro
150             155                 160                 165 gag gtg gac cca ctg ccc ttc ccg ggc ccc ttc cct gct ggg ccc ctg      764
Glu Val Asp Pro Leu Pro Phe Pro Gly Pro Phe Pro Ala Gly Pro Leu
                170                 175                 180 gca gtc gct gga ggc ccc cgg aag aca gca gcc cca gtg aat gca ctg      812
Ala Val Ala Gly Gly Pro Arg Lys Thr Ala Ala Pro Val Asn Ala Leu
            185                 190                 195 gtg tct cat ctg ctg gtg gtt gag cct gag aag ctc tat gcc atg cct      860
Val Ser His Leu Leu Val Val Glu Pro Glu Lys Leu Tyr Ala Met Pro
            200                 205                 210 gac ccc gca ggc cct gat ggg cac ctc cca gcc gtg gct acc ctc tgt      908
Asp Pro Ala Gly Pro Asp Gly His Leu Pro Ala Val Ala Thr Leu Cys
215             220                 225 gac ctc ttt gac cga gag att gtg gtc acc atc agc tgg gcc aag agc      956
Asp Leu Phe Asp Arg Glu Ile Val Val Thr Ile Ser Trp Ala Lys Ser
230             235                 240                 245 atc cca ggc ttc tca tcg ctg tcg ctg tct gac cag atg tca gta ctg     1004
Ile Pro Gly Phe Ser Ser Leu Ser Leu Ser Asp Gln Met Ser Val Leu
                250                 255                 260 cag agc gtg tgg atg gag gtg ctg gtg ctg ggt gtg gcc cag cgc tca     1052
Gln Ser Val Trp Met Glu Val Leu Val Leu Gly Val Ala Gln Arg Ser
                265                 270                 275 ctg cca ctg cag gat gag ctg gcc ttc gct gag gac tta gtc ctg gat     1100
Leu Pro Leu Gln Asp Glu Leu Ala Phe Ala Glu Asp Leu Val Leu Asp
            280                 285                 290 gaa gag ggg gca cgg gca gct ggc ctg ggg gaa ctg ggg gct gcc ctg     1148
Glu Glu Gly Ala Arg Ala Ala Gly Leu Gly Glu Leu Gly Ala Ala Leu
295                 300                 305 ctg caa cta gtg cgg cgg ctg cag gcc ctg cgg ctg gag cga gag gag     1196
Leu Gln Leu Val Arg Arg Leu Gln Ala Leu Arg Leu Glu Arg Glu Glu
310                 315                 320                 325 tat gtt cta cta aag gcc ttg gcc ctt gcc aat tca gac tct gtg cac     1244
Tyr Val Leu Leu Lys Ala Leu Ala Leu Ala Asn Ser Asp Ser Val His
                330                 335                 340 atc gaa gat gcc gag gct gtg gag cag ctg cga gaa gct ctg cac gag     1292
Ile Glu Asp Ala Glu Ala Val Glu Gln Leu Arg Glu Ala Leu His Glu
            345                 350                 355 gcc ctg ctg gag tat gaa gcc ggc cgg gct ggc ccc gga ggg ggt gct     1340
Ala Leu Leu Glu Tyr Glu Ala Gly Arg Ala Gly Pro Gly Gly Gly Ala
        360                 365                 370 gag cgg cgg cgg gcg ggc agg ctg ctc ctc acg cta ccg ctc ctc cgc     1388
Glu Arg Arg Arg Ala Gly Arg Leu Leu Leu Thr Leu Pro Leu Leu Arg
375                 380                 385 cag aca gcg ggc aaa gtg ctg gcc cat ttc tat ggg gtg aag ctg gag     1436
Gln Thr Ala Gly Lys Val Leu Ala His Phe Tyr Gly Val Lys Leu Glu
390                 395                 400                 405 ggc aag gtg ccc atg cac aag ctg ttc ttg gag atg ctc gag gcc atg     1484
Gly Lys Val Pro Met His Lys Leu Phe Leu Glu Met Leu Glu Ala Met
                410                 415                 420
```

```
atg gac tga ggcaaggggt gggactggtg ggggttctgg caggacctgc        1533
Met Asp ctagcatggg gtcagcccca agggctgggg cggagctggg gtctgggcag tgccacagcc   1593
tgctggcagg gccagggcaa tgccatcagc ccctgggaac aggccccacg ccctctcctc   1653
cccctcctag ggggtgtcag aagctgggaa cgtgtgtcca ggctctgggc acagtgctgc   1713
cccttgcaag ccataacgtg cccccagagt gtagggggcc ttgcggaagc cataggggc    1773 tgcacgggat gcgtgggagg cagaaaccta tctcaggag ggaaggggat ggaggccaga    1833
gtctcccagt gggtgatgct tttgctgctg cttaatccta ccccctcttc aaagcagagt   1893
gggacttgga gagcaaaggc ccatgccccc ttcgctcctc ctctcatcat ttgcattggg   1953
cattagtgtc ccccttgaa gcaataactc caagcagact ccagccctg gaccctggg     2013 gtggccaggg cttccccatc agctcccaac gagcctcctc aggggtagg agagcactgc   2073 ctctatgccc tgcagagcaa taacactata tttattttg ggtttggcca gggaggcgca   2133
gggacatggg gcaagccagg gcccagagcc cttggctgta cagagactct attttaatgt   2193
atatttgctg caaagagaaa ccgcttttgg ttttaaacct ttaatgagaa aaaaatatat   2253
aataccgagc tcaaaaaaaa aaaaaaaaa a                                  2284

<210> SEQ ID NO 2
<211> LENGTH: 423
<212> TYPE: PRT
<213> ORGANISM: Homo sapiens

<400> SEQUENCE: 2

Met Ser Ser Gln Val Gly Ile Glu Pro Leu Tyr Ile Lys Ala Glu
1               5                   10                  15

Pro Ala Ser Pro Asp Ser Pro Lys Gly Ser Ser Glu Thr Glu Thr
                20                  25                  30

Pro Pro Val Ala Leu Ala Pro Gly Pro Ala Pro Thr Arg Cys Leu Pro
                35                  40                      45

Gly His Lys Glu Glu Asp Gly Glu Gly Ala Gly Pro Gly Glu Gln
        50                  55                  60

Gly Gly Gly Lys Leu Val Leu Ser Ser Leu Pro Lys Arg Leu Cys Leu
65                  70                  75                  80

Val Cys Gly Asp Val Ala Ser Gly Tyr His Tyr Gly Val Ala Ser Cys
                85                  90                  95

Glu Ala Cys Lys Ala Phe Phe Lys Arg Thr Ile Gln Gly Ser Ile Glu
                100                 105                 110

Tyr Ser Cys Pro Ala Ser Asn Glu Cys Glu Ile Thr Lys Arg Arg Arg
        115                 120                 125

Lys Ala Cys Gln Ala Cys Arg Phe Thr Lys Cys Leu Arg Val Gly Met
    130                 135                 140

Leu Lys Glu Gly Val Arg Leu Asp Arg Val Arg Gly Gly Arg Gln Lys
145                 150                 155                 160

Tyr Lys Arg Arg Pro Glu Val Asp Pro Leu Pro Phe Pro Gly Pro Phe
                165                 170                 175

Pro Ala Gly Pro Leu Ala Val Ala Gly Gly Pro Arg Lys Thr Ala Ala
                180                 185                 190

Pro Val Asn Ala Leu Val Ser His Leu Leu Val Val Glu Pro Glu Lys
        195                 200                 205

Leu Tyr Ala Met Pro Asp Pro Ala Gly Pro Asp Gly His Leu Pro Ala
    210                 215                 220
```

```
Val Ala Thr Leu Cys Asp Leu Phe Asp Arg Glu Ile Val Thr Ile
225                 230                 235                 240

Ser Trp Ala Lys Ser Ile Pro Gly Phe Ser Ser Leu Ser Leu Ser Asp
            245                 250                 255

Gln Met Ser Val Leu Gln Ser Val Trp Met Glu Val Leu Val Leu Gly
            260                 265                 270

Val Ala Gln Arg Ser Leu Pro Leu Gln Asp Glu Leu Ala Phe Ala Glu
            275                 280                 285

Asp Leu Val Leu Asp Glu Glu Gly Ala Arg Ala Ala Gly Leu Gly Glu
            290                 295                 300

Leu Gly Ala Ala Leu Leu Gln Leu Val Arg Arg Leu Gln Ala Leu Arg
305                 310                 315                 320

Leu Glu Arg Glu Glu Tyr Val Leu Leu Lys Ala Leu Ala Leu Ala Asn
                325                 330                 335

Ser Asp Ser Val His Ile Glu Asp Ala Glu Val Glu Gln Leu Arg
            340                 345                 350

Glu Ala Leu His Glu Ala Leu Leu Glu Tyr Glu Ala Gly Arg Ala Gly
            355                 360                 365

Pro Gly Gly Gly Ala Glu Arg Arg Ala Gly Arg Leu Leu Thr
370                 375                 380

Leu Pro Leu Leu Arg Gln Thr Ala Gly Lys Val Leu Ala His Phe Tyr
385                 390                 395                 400

Gly Val Lys Leu Glu Gly Lys Val Pro Met His Lys Leu Phe Leu Glu
                405                 410                 415

Met Leu Glu Ala Met Met Asp
            420

<210> SEQ ID NO 3
<211> LENGTH: 4745
<212> TYPE: DNA
<213> ORGANISM: Homo sapiens
<220> FEATURE:
<221> NAME/KEY: CDS
<222> LOCATION: (151)..(1515)

<400> SEQUENCE: 3
gcaatgcatt atgggccgcc gtttcagtcg gtcgacgctc accggacagg aagcgtctcg      60
gagacagtct gcgaccggac gggtctaggt gagacagaag ccaaacagga ggaggaagtg     120
gagggactga tcctttgaaa tactccagcc atg act aaa aga gaa gca gag gag     174
                                  Met Thr Lys Arg Glu Ala Glu Glu
                                    1               5 ctg ata gaa att gag att gat gga aca gag aaa gca gag tgc aca gaa     222
Leu Ile Glu Ile Glu Ile Asp Gly Thr Glu Lys Ala Glu Cys Thr Glu
        10                  15                  20 gaa agc att gta gaa caa acc tac gcg cca gct gaa tgt gta agc cag     270
Glu Ser Ile Val Glu Gln Thr Tyr Ala Pro Ala Glu Cys Val Ser Gln
25                  30                  35                  40 gcc ata gac atc aat gaa cca ata ggc aat tta aag aaa ctg cta gaa     318
Ala Ile Asp Ile Asn Glu Pro Ile Gly Asn Leu Lys Lys Leu Leu Glu
                45                  50                  55 cca aga cta cag tgt tct ttg gat gct cat gaa att tgt ctg caa gat     366
Pro Arg Leu Gln Cys Ser Leu Asp Ala His Glu Ile Cys Leu Gln Asp
            60                  65                  70 atc cag ctg gat cca gaa cga agt tta ttt gac caa gga gta aaa aca     414
Ile Gln Leu Asp Pro Glu Arg Ser Leu Phe Asp Gln Gly Val Lys Thr
        75                  80                  85
```

```
gat gga act gta cag ctt agt gta cag gta att tct tac caa gga att      462
Asp Gly Thr Val Gln Leu Ser Val Gln Val Ile Ser Tyr Gln Gly Ile
 90              95              100 gaa cca aag tta aac atc ctt gaa att gtt aaa cct gcg gac act gtt      510
Glu Pro Lys Leu Asn Ile Leu Glu Ile Val Lys Pro Ala Asp Thr Val
105             110              115              120 gag gtt gtt att gat cca gat gcc cac cat gct gaa tca gaa gca cat      558
Glu Val Val Ile Asp Pro Asp Ala His His Ala Glu Ser Glu Ala His
            125              130              135 ctt gtt gaa gaa gct caa gtg ata act ctt gat ggc aca aaa cac atc      606
Leu Val Glu Glu Ala Gln Val Ile Thr Leu Asp Gly Thr Lys His Ile
        140              145              150 aca acc att tca gat gaa act tca gaa caa gtg aca aga tgg gct gct      654
Thr Thr Ile Ser Asp Glu Thr Ser Glu Gln Val Thr Arg Trp Ala Ala
            155              160              165 gca ctg gaa ggc tat agg aaa gaa caa gaa cgc ctt ggg ata ccc tat      702
Ala Leu Glu Gly Tyr Arg Lys Glu Gln Glu Arg Leu Gly Ile Pro Tyr
        170              175              180 gat ccc ata cag tgg tcc aca gac caa gtc ctg cat tgg gtg gtt tgg      750
Asp Pro Ile Gln Trp Ser Thr Asp Gln Val Leu His Trp Val Val Trp
185             190              195              200 gta atg aag gaa ttc agc atg acc gat ata gac ctc acc aca ctc aac      798
Val Met Lys Glu Phe Ser Met Thr Asp Ile Asp Leu Thr Thr Leu Asn
            205              210              215 att tcg ggg aga gaa tta tgt agt ctc aac caa gaa gat ttt ttt cag      846
Ile Ser Gly Arg Glu Leu Cys Ser Leu Asn Gln Glu Asp Phe Phe Gln
        220              225              230 cgg gtt cct cgg gga gaa att ctc tgg agt cat ctg gaa ctt ctc cga      894
Arg Val Pro Arg Gly Glu Ile Leu Trp Ser His Leu Glu Leu Leu Arg
            235              240              245 aaa tat gta ttg gca agt caa gaa caa cag atg aat gaa ata gtt aca      942
Lys Tyr Val Leu Ala Ser Gln Glu Gln Gln Met Asn Glu Ile Val Thr
        250              255              260 att gat caa cct gtg caa att att cca gca tca gtg caa tct gct aca      990
Ile Asp Gln Pro Val Gln Ile Ile Pro Ala Ser Val Gln Ser Ala Thr
265             270              275              280 cct act acc att aaa gtt ata aat agt agt gcg aaa gca gcc aaa gta     1038
Pro Thr Thr Ile Lys Val Ile Asn Ser Ser Ala Lys Ala Ala Lys Val
            285              290              295 caa aga gcg ccg agg att tca gga gaa gat aga agc tca cct ggg aac     1086
Gln Arg Ala Pro Arg Ile Ser Gly Glu Asp Arg Ser Ser Pro Gly Asn
        300              305              310 aga aca gga aac aat ggc caa atc caa cta tgg cag ttt ttg cta gaa     1134
Arg Thr Gly Asn Asn Gly Gln Ile Gln Leu Trp Gln Phe Leu Leu Glu
            315              320              325 ctt ctt act gat aag gac gct cga gac tgc att tct tgg gtt ggt gat     1182
Leu Leu Thr Asp Lys Asp Ala Arg Asp Cys Ile Ser Trp Val Gly Asp
        330              335              340 gaa ggt gaa ttt aag cta aat cag cct gaa ctg gtt gca cag aaa tgg     1230
Glu Gly Glu Phe Lys Leu Asn Gln Pro Glu Leu Val Ala Gln Lys Trp
345             350              355              360 gga cag cgt aaa aat aag cct acg atg aac tat gag aaa ctc agt cgt     1278
Gly Gln Arg Lys Asn Lys Pro Thr Met Asn Tyr Glu Lys Leu Ser Arg
            365              370              375 gca tta aga tat tat tac gat ggg gac atg att tgt aaa gtt caa ggc     1326
Ala Leu Arg Tyr Tyr Tyr Asp Gly Asp Met Ile Cys Lys Val Gln Gly
        380              385              390 aag aga ttt gtg tac aag ttt gtc tgt gac ttg aag act ctt att gga     1374
Lys Arg Phe Val Tyr Lys Phe Val Cys Asp Leu Lys Thr Leu Ile Gly
            395              400              405
```

```
tac agt gca gcg gag ttg aac cgt ttg gtc aca gaa tgt gaa cag aag         1422
Tyr Ser Ala Ala Glu Leu Asn Arg Leu Val Thr Glu Cys Glu Gln Lys
    410                 415                 420 aaa ctt gca aag atg cag ctc cat gga att gcc cag cca gtc aca gca         1470
Lys Leu Ala Lys Met Gln Leu His Gly Ile Ala Gln Pro Val Thr Ala
425                 430                 435                 440 gta gct ctg gct act gct tct ctg caa acg gaa aag gat aat tga             1515
Val Ala Leu Ala Thr Ala Ser Leu Gln Thr Glu Lys Asp Asn
                445                 450 gccccaggac attctgagac tccaaagtct tcttaaaat gtttagagca agtatagctc        1575
ttacctttat tactgaattt gaatcttctt ttatttctag gctgtacagt ctgatgcatg       1635 attttttat aaatatttca tactcttgtg aatttggatc ttttactttt gagcatatat        1695
tttagaatat gtgtatgtta aaggatctcc acaatgtctg cagtgtgaag gcaggttcat       1755
tgtggaatag tttaacagtc aggaaggcta aactggtcag tattaatgtg tagccctacc      1815
aaaaatagcc agtagtatct gaaaatgaaa ataaatgaa gtatctctag gaaacagtct       1875
ggcttaacta ttttgaaaa tataactgtt tccctctct gctgctttag atgttgcttt        1935
acatagaacc agaaaatgga atttctcagc taaagcatgt gtgcctgttt catctaatca      1995
agcagagcta aaatgttcat accgaataaa tttatattaa taaattacta aactaagagt      2055
atcaggttat ttatatattt gcaagcaaag gacagtaaga agttgactgg caaaagagca      2115
gtgctgaagg aggagatcca ggtttaaatc tggcttatta actcaagcca attttaagga      2175
ttttctgtat agattactca tgtcagacca agaatttaaa ttattttgag agaggcattt      2235
aattctaata aaccagctgt tataaaaatt ataaaatgat ctctgttttt cctgtcagag      2295
atttaaaaaa ctgaaaaggt atacctcaac ccaaaaataa aggtttgttt tggtttgtta      2355
tggcttcctt ttttaaaaaa ttaccctgta gtgccagttt attatgcaaa gcagcttata      2415
ttcctttgtt tctgataaaa tgaagacttt aaatcagtca gtagtacttt accttcaag       2475 gcattagtaa attacttgca aatagttta aaggaaaat acgacctttg ttataggcag        2535
tcttctcttt aagacaatac ttttccactt gttttccttt tccatattat atatgtgtat      2595
tcatatagct gtatacatat tcagttgatc atttataaa catatgaagg cataaagata      2655
tacagaagaa aaattattaa acaactcatt ttaagattca aattaactaa ttcctgcata      2715
tatgacattc cttacataag cgaacactaa acaaaaatgg ctagaaatgt ctttttcttt      2775
cttttctctc tttgttgttt aaggtattaa gcacgaatta ttacatgaga ctggcagata     2835
gctattaatc ctcttacaga tttgagaaag ttgattctca aatatttatg caccttctcc      2895
ttcattgttt tctttaaatc tgtcctctta aaaagcttct taagagctca gttaatgctt      2955
ttgacttaac taggagaaaa aggcatgata atacaggcaa gatggcattg ttagcaattc      3015
tggtagtggt ttggaatgaa tcctaagagg cagggatctt aaggacaagg aagagaagag      3075
agagagggag ggatctttga tctctttctc tggtaatctt aatgcataat tttactaaaa      3135
catgttctca attcattcat attattaagc tcttcctgca gttgatatct gagcagagta      3195
agatttgtat ttccattttt acttttttga aagagaatat atggacagat tattagtaca      3255
atttgggcac tgtggtttta agaatatctg agtaaaataa caatatgaaa taataaacag      3315
aagctctaac gtcaggtaac aaatagacag caagaaaggt tttgcaccat cctcttacgg      3375
cctagagagt tgacaagttg cttgtagttt taaaaaaata taaagtata cccttctggt       3435 atatcatcaa gagcttaaga atcttggctt tcatatttaa aatgctttg gggagacata       3495
```

-continued

```
tattaaaatt ttagccaaga tgatagacat gtctcaatta tatatgtgtg tgtatgtttt    3555
taaagctaaa aacattactt ttagatccct agaatgaaaa ttttttttctc atctatgcaa    3615 ttcccatatg gttttttttt aaatcatatt ttattcattt tctcccttta gcaatttttca   3675 ttttatttct cataatttga acagagacag ttctcataca tgatcagatg cttttttttt    3735
cttcttacca tcatttatgc atgacatagg taatgtgact aatttctcca gttgattcaa    3795
gaaactcatt actttgcctc aaattatatg taaaatattt gttttactta ggttacagtt    3855
atcagaaagg tagttttttt cttctattaa aatataacat tgtgaaagaa aataaaattt    3915
atgctattct ttgctttgtt tttataaatg aattttttcat agaatttaca gtatattcaa    3975
aggaagaaag ataaaattat tggtcatcat ttgtaccttta gaagtacaag aatttaagta   4035
aaagaaatgt tcattttttgt tttaaaattt gttttccatg tgaagttttt attgagccaa   4095
ctttcataca tatcttgcta gcctaaagtc taaatatttg tgttggcatc agaaaaacaa    4155
atgaggcaga attgctatgt gtggttgatc ttcagataaa ttgactgatc acagttatt    4215 ttgtatcagt ctatgttatt aggaaaaatt gtttagttgt tttctccccct gattaatggt   4275 gatattcaag tatgatacaa aaagaattgt accaccaaat attttttgtga ggtctgctgt   4335 tttccatatt cattttatgc tactgccttt aagaaagaac tagtgtatcc ttgaaatagc    4395
acaaaaatgt tttaaaattc ataattgcaa aacaaatctg tgactaactt aatgtcttca    4455
gatctaaagg gtgtaaaaat attgatactt caatatttca cttgctgcca ggaaaaacaa    4515
aattctcaat cttttgtaaa tgggaggagg acttttgcat acattttttac tctttaaata   4575 acgacaacga cacttatact gtcataataa caattatgta tttctttgtg gttttaattt    4635
tttttgtaat tttacataaa acagttattt tctatttttta cgcagataaa tatttgtgca   4695
taaaatgtaa aaatagtaaa atgagaaaaa taaaactatt atacagtaaa                4745
```

<210> SEQ ID NO 4
<211> LENGTH: 454
<212> TYPE: PRT
<213> ORGANISM: Homo sapiens

<400> SEQUENCE: 4

```
Met Thr Lys Arg Glu Ala Glu Glu Leu Ile Glu Ile Glu Ile Asp Gly
1               5                   10                  15

Thr Glu Lys Ala Glu Cys Thr Glu Glu Ser Ile Val Glu Gln Thr Tyr
            20                  25                  30

Ala Pro Ala Glu Cys Val Ser Gln Ala Ile Asp Ile Asn Glu Pro Ile
        35                  40                  45

Gly Asn Leu Lys Lys Leu Leu Glu Pro Arg Leu Gln Cys Ser Leu Asp
    50                  55                  60

Ala His Glu Ile Cys Leu Gln Asp Ile Gln Leu Asp Pro Glu Arg Ser
65                  70                  75                  80

Leu Phe Asp Gln Gly Val Lys Thr Asp Gly Thr Val Gln Leu Ser Val
                85                  90                  95

Gln Val Ile Ser Tyr Gln Gly Ile Glu Pro Lys Leu Asn Ile Leu Glu
            100                 105                 110

Ile Val Lys Pro Ala Asp Thr Val Glu Val Ile Asp Pro Asp Ala
        115                 120                 125

His His Ala Glu Ser Glu Ala His Leu Val Glu Glu Ala Gln Val Ile
    130                 135                 140

Thr Leu Asp Gly Thr Lys His Ile Thr Thr Ile Ser Asp Glu Thr Ser
145                 150                 155                 160
```

Glu Gln Val Thr Arg Trp Ala Ala Leu Glu Gly Tyr Arg Lys Glu
            165                 170                 175

Gln Glu Arg Leu Gly Ile Pro Tyr Asp Pro Ile Gln Trp Ser Thr Asp
        180                 185                 190

Gln Val Leu His Trp Val Val Trp Val Met Lys Glu Phe Ser Met Thr
    195                 200                 205

Asp Ile Asp Leu Thr Thr Leu Asn Ile Ser Gly Arg Glu Leu Cys Ser
210                 215                 220

Leu Asn Gln Glu Asp Phe Phe Gln Arg Val Pro Arg Gly Glu Ile Leu
225                 230                 235                 240

Trp Ser His Leu Glu Leu Leu Arg Lys Tyr Val Leu Ala Ser Gln Glu
            245                 250                 255

Gln Gln Met Asn Glu Ile Val Thr Ile Asp Gln Pro Val Gln Ile Ile
        260                 265                 270

Pro Ala Ser Val Gln Ser Ala Thr Pro Thr Thr Ile Lys Val Ile Asn
    275                 280                 285

Ser Ser Ala Lys Ala Ala Lys Val Gln Arg Ala Pro Arg Ile Ser Gly
290                 295                 300

Glu Asp Arg Ser Ser Pro Gly Asn Arg Thr Gly Asn Asn Gly Gln Ile
305                 310                 315                 320

Gln Leu Trp Gln Phe Leu Leu Glu Leu Leu Thr Asp Lys Asp Ala Arg
            325                 330                 335

Asp Cys Ile Ser Trp Val Gly Asp Glu Gly Glu Phe Lys Leu Asn Gln
        340                 345                 350

Pro Glu Leu Val Ala Gln Lys Trp Gly Gln Arg Lys Asn Lys Pro Thr
    355                 360                 365

Met Asn Tyr Glu Lys Leu Ser Arg Ala Leu Arg Tyr Tyr Tyr Asp Gly
370                 375                 380

Asp Met Ile Cys Lys Val Gln Gly Lys Arg Phe Val Tyr Lys Phe Val
385                 390                 395                 400

Cys Asp Leu Lys Thr Leu Ile Gly Tyr Ser Ala Ala Glu Leu Asn Arg
            405                 410                 415

Leu Val Thr Glu Cys Glu Gln Lys Lys Leu Ala Lys Met Gln Leu His
        420                 425                 430

Gly Ile Ala Gln Pro Val Thr Ala Val Ala Leu Ala Thr Ala Ser Leu
    435                 440                 445

Gln Thr Glu Lys Asp Asn
    450

<210> SEQ ID NO 5
<211> LENGTH: 6849
<212> TYPE: DNA
<213> ORGANISM: Homo sapiens
<220> FEATURE:
<221> NAME/KEY: CDS
<222> LOCATION: (620)..(3031)

<400> SEQUENCE: 5
gcggtctctc gctctgcgcg cacacaccac acacacgcac acgcacacac acgcgcgcac      60
acacgcagcc ggcacaggcg gcggcggcgg ctgcccaagt caggacgaac ctatctaggt     120
accgtcttga gaaggcggca gcggcggcgg cggcggcggc ggcggcagcc cgagcatccc     180
tcctctcccg gagagggagc accgccgaga gtttccgttc cctttgccat tcccttcccc     240
ctccttttct tttattttcg agagaatttc ttcttggctt attggtttaa tttgattttt     300

| | | |
|---|---|---|
| aaaatttttgg gttgcttttg tgtatgtgtg cttttttttt ctttcctcat tttatttgca | | 360 |
| tccagagcat ggcgggctgc gggctgtcgg aagacaccct cttctcttcc ttcttttaca | | 420 |
| actacggctc ctcctgggaa accccttcca accaggtttt ttgcgaaaat cagtgaacta | | 480 |
| atattggtaa aattggagcc ccatggatga agggtacttt tctgcccctg gactgccctg | | 540 |
| gctgctgctt tggtaaaagc ttgcaaggag agagagtaac agccgctggc gaatccagtt | | 600 |

```
tgtgcaagca gcatcagca atg gat gag acc tcc cca agg ctg gaa gaa gac           652
                     Met Asp Glu Thr Ser Pro Arg Leu Glu Glu Asp
                      1               5                  10 tgg aaa aaa gta ctt cag cga gaa gca ggc tgg cag tgt gct gct ctg            700
Trp Lys Lys Val Leu Gln Arg Glu Ala Gly Trp Gln Cys Ala Ala Leu
         15                  20                  25 gtt ggt gaa gac cag cct ctt tgc cca gat ctt cct gaa ctt gat ctt            748
Val Gly Glu Asp Gln Pro Leu Cys Pro Asp Leu Pro Glu Leu Asp Leu
 30                  35                  40 tct gaa cta gat gtg aac gac ttg gat aca gac agc ttt ctg ggt gga            796
Ser Glu Leu Asp Val Asn Asp Leu Asp Thr Asp Ser Phe Leu Gly Gly
         45                  50                  55 ctc aag tgg tgc agt gac caa tca gaa ata ata tcc aat cag tac aac            844
Leu Lys Trp Cys Ser Asp Gln Ser Glu Ile Ile Ser Asn Gln Tyr Asn
 60                  65                  70                  75 aat gag cct tca aac ata ttt gag aag ata gat gaa gag aat gag gca            892
Asn Glu Pro Ser Asn Ile Phe Glu Lys Ile Asp Glu Glu Asn Glu Ala
             80                  85                  90 aac ttg cta gca gtc ctc aca gag aca cta gac agt ctc cct gtg gat            940
Asn Leu Leu Ala Val Leu Thr Glu Thr Leu Asp Ser Leu Pro Val Asp
                 95                 100                 105 gaa gac gga ttg ccc tca ttt gat gcg ctg aca gat gga gac gtg acc            988
Glu Asp Gly Leu Pro Ser Phe Asp Ala Leu Thr Asp Gly Asp Val Thr
         110                 115                 120 act gac aat gag gct agt cct tcc tcc atg cct gac ggc acc cct cca           1036
Thr Asp Asn Glu Ala Ser Pro Ser Ser Met Pro Asp Gly Thr Pro Pro
 125                 130                 135 ccc cag gag gca gaa gag ccg tct cta ctt aag aag ctc tta ctg gca           1084
Pro Gln Glu Ala Glu Glu Pro Ser Leu Leu Lys Lys Leu Leu Leu Ala
140                 145                 150                 155 cca gcc aac act cag cta agt tat aat gaa tgc agt ggt ctc agt acc           1132
Pro Ala Asn Thr Gln Leu Ser Tyr Asn Glu Cys Ser Gly Leu Ser Thr
         160                 165                 170 cag aac cat gca aat cac aat cac agg atc aga aca aac cct gca att           1180
Gln Asn His Ala Asn His Asn His Arg Ile Arg Thr Asn Pro Ala Ile
     175                 180                 185 gtt aag act gag aat tca tgg agc aat aaa gcg aag agt att tgt caa           1228
Val Lys Thr Glu Asn Ser Trp Ser Asn Lys Ala Lys Ser Ile Cys Gln
         190                 195                 200 cag caa aag cca caa aga cgt ccc tgc tcg gag ctt ctc aaa tat ctg           1276
Gln Gln Lys Pro Gln Arg Arg Pro Cys Ser Glu Leu Leu Lys Tyr Leu
 205                 210                 215 acc aca aac gat gac cct cct cac acc aaa ccc aca gag aac aga aac           1324
Thr Thr Asn Asp Asp Pro Pro His Thr Lys Pro Thr Glu Asn Arg Asn
220                 225                 230                 235 agc agc aga gac aaa tgc acc tcc aaa aag aag tcc cac aca cag tcg           1372
Ser Ser Arg Asp Lys Cys Thr Ser Lys Lys Lys Ser His Thr Gln Ser
         240                 245                 250 cag tca caa cac tta caa gcc aaa cca aca act tta tct ctt cct ctg           1420
Gln Ser Gln His Leu Gln Ala Lys Pro Thr Thr Leu Ser Leu Pro Leu
     255                 260                 265
```

```
acc cca gag tca cca aat gac ccc aag ggt tcc cca ttt gag aac aag    1468
Thr Pro Glu Ser Pro Asn Asp Pro Lys Gly Ser Pro Phe Glu Asn Lys
        270             275             280 act att gaa cgc acc tta agt gtg gaa ctc tct gga act gca ggc cta    1516
Thr Ile Glu Arg Thr Leu Ser Val Glu Leu Ser Gly Thr Ala Gly Leu
285             290             295 act cca ccc acc act cct cct cat aaa gcc aac caa gat aac cct ttt    1564
Thr Pro Pro Thr Thr Pro Pro His Lys Ala Asn Gln Asp Asn Pro Phe
300             305             310             315 agg gct tct cca aag ctg aag tcc tct tgc aag act gtg gtg cca cca    1612
Arg Ala Ser Pro Lys Leu Lys Ser Ser Cys Lys Thr Val Val Pro Pro
                320             325             330 cca tca aag aag ccc agg tac agt gag tct tct ggt aca caa ggc aat    1660
Pro Ser Lys Lys Pro Arg Tyr Ser Glu Ser Ser Gly Thr Gln Gly Asn
            335             340             345 aac tcc acc aag aaa ggg ccg gag caa tcc gag ttg tat gca caa ctc    1708
Asn Ser Thr Lys Lys Gly Pro Glu Gln Ser Glu Leu Tyr Ala Gln Leu
        350             355             360 agc aag tcc tca gtc ctc act ggt gga cac gag gaa agg aag acc aag    1756
Ser Lys Ser Ser Val Leu Thr Gly Gly His Glu Glu Arg Lys Thr Lys
365             370             375 cgg ccc agt ctg cgg ctg ttt ggt gac cat gac tat tgc cag tca att    1804
Arg Pro Ser Leu Arg Leu Phe Gly Asp His Asp Tyr Cys Gln Ser Ile
380             385             390             395 aat tcc aaa aca gaa ata ctc att aat ata tca cag gag ctc caa gac    1852
Asn Ser Lys Thr Glu Ile Leu Ile Asn Ile Ser Gln Glu Leu Gln Asp
                400             405             410 tct aga caa cta gaa aat aaa gat gtc tcc tct gat tgg cag ggg cag    1900
Ser Arg Gln Leu Glu Asn Lys Asp Val Ser Ser Asp Trp Gln Gly Gln
            415             420             425 att tgt tct tcc aca gat tca gac cag tgc tac ctg aga gag act ttg    1948
Ile Cys Ser Ser Thr Asp Ser Asp Gln Cys Tyr Leu Arg Glu Thr Leu
        430             435             440 gag gca agc aag cag gtc tct cct tgc agc aca aga aaa cag ctc caa    1996
Glu Ala Ser Lys Gln Val Ser Pro Cys Ser Thr Arg Lys Gln Leu Gln
445             450             455 gac cag gaa atc cga gcc gag ctg aac aag cac ttc ggt cat ccc agt    2044
Asp Gln Glu Ile Arg Ala Glu Leu Asn Lys His Phe Gly His Pro Ser
460             465             470             475 caa gct gtt ttt gac gac gaa gca gac aag acc ggt gaa ctg agg gac    2092
Gln Ala Val Phe Asp Asp Glu Ala Asp Lys Thr Gly Glu Leu Arg Asp
                480             485             490 agt gat ttc agt aat gaa caa ttc tcc aaa cta cct atg ttt ata aat    2140
Ser Asp Phe Ser Asn Glu Gln Phe Ser Lys Leu Pro Met Phe Ile Asn
            495             500             505 tca gga cta gcc atg gat ggc ctg ttt gat gac agc gaa gat gaa agt    2188
Ser Gly Leu Ala Met Asp Gly Leu Phe Asp Asp Ser Glu Asp Glu Ser
        510             515             520 gat aaa ctg agc tac cct tgg gat ggc acg caa tcc tat tca ttg ttc    2236
Asp Lys Leu Ser Tyr Pro Trp Asp Gly Thr Gln Ser Tyr Ser Leu Phe
525             530             535 aat gtg tct cct tct tgt tct tct ttt aac tct cca tgt aga gat tct    2284
Asn Val Ser Pro Ser Cys Ser Ser Phe Asn Ser Pro Cys Arg Asp Ser
540             545             550             555 gtg tca cca ccc aaa tcc tta ttt tct caa aga ccc caa agg atg cgc    2332
Val Ser Pro Pro Lys Ser Leu Phe Ser Gln Arg Pro Gln Arg Met Arg
                560             565             570
```

-continued

| | | |
|---|---|---|
| tct cgt tca agg tcc ttt tct cga cac agg tcg tgt tcc cga tca cca<br>Ser Arg Ser Arg Ser Phe Ser Arg His Arg Ser Cys Ser Arg Ser Pro<br>575 580 585 | 2380 |
| tat tcc agg tca aga tca agg tct cca ggc agt aga tcc tct tca aga<br>Tyr Ser Arg Ser Arg Ser Arg Ser Pro Gly Ser Arg Ser Ser Ser Arg<br>590 595 600 | 2428 |
| tcc tgc tat tac tat gag tca agc cac tac aga cac cgc acg cac cga<br>Ser Cys Tyr Tyr Tyr Glu Ser Ser His Tyr Arg His Arg Thr His Arg<br>605 610 615 | 2476 |
| aat tct ccc ttg tat gtg aga tca cgt tca aga tcg ccc tac agc cgt<br>Asn Ser Pro Leu Tyr Val Arg Ser Arg Ser Arg Ser Pro Tyr Ser Arg<br>620 625 630 635 | 2524 |
| cgg ccc agg tat gac agc tac gag gaa tat cag cac gag agg ctg aag<br>Arg Pro Arg Tyr Asp Ser Tyr Glu Glu Tyr Gln His Glu Arg Leu Lys<br>640 645 650 | 2572 |
| agg gaa gaa tat cgc aga gag tat gag aag cga gag tct gag agg gcc<br>Arg Glu Glu Tyr Arg Arg Glu Tyr Glu Lys Arg Glu Ser Glu Arg Ala<br>655 660 665 | 2620 |
| aag caa agg gag agg cag agg cag aag gca att gaa gag cgc cgt gtg<br>Lys Gln Arg Glu Arg Gln Arg Gln Lys Ala Ile Glu Glu Arg Arg Val<br>670 675 680 | 2668 |
| att tat gtc ggt aaa atc aga cct gac aca aca cgg aca gaa ctg agg<br>Ile Tyr Val Gly Lys Ile Arg Pro Asp Thr Thr Arg Thr Glu Leu Arg<br>685 690 695 | 2716 |
| gac cgt ttt gaa gtt ttt ggt gaa att gag gag tgc aca gta aat ctg<br>Asp Arg Phe Glu Val Phe Gly Glu Ile Glu Glu Cys Thr Val Asn Leu<br>700 705 710 715 | 2764 |
| cgg gat gat gga gac agc tat ggt ttc att acc tac cgt tat acc tgt<br>Arg Asp Asp Gly Asp Ser Tyr Gly Phe Ile Thr Tyr Arg Tyr Thr Cys<br>720 725 730 | 2812 |
| gat gct ttt gct gct ctt gaa aat gga tac act ttg cgc agg tca aac<br>Asp Ala Phe Ala Ala Leu Glu Asn Gly Tyr Thr Leu Arg Arg Ser Asn<br>735 740 745 | 2860 |
| gaa act gac ttt gag ctg tac ttt tgt gga cgc aag caa ttt ttc aag<br>Glu Thr Asp Phe Glu Leu Tyr Phe Cys Gly Arg Lys Gln Phe Phe Lys<br>750 755 760 | 2908 |
| tct aac tat gca gac cta gat tca aac tca gat gac ttt gac cct gct<br>Ser Asn Tyr Ala Asp Leu Asp Ser Asn Ser Asp Asp Phe Asp Pro Ala<br>765 770 775 | 2956 |
| tcc acc aag agc aag tat gac tct ctg gat ttt gat agt tta ctg aaa<br>Ser Thr Lys Ser Lys Tyr Asp Ser Leu Asp Phe Asp Ser Leu Leu Lys<br>780 785 790 795 | 3004 |
| gaa gct cag aga agc ttg cgc agg taa catgttccct agctgaggat<br>Glu Ala Gln Arg Ser Leu Arg Arg<br>800 | 3051 |
| gacagaggga tggcgaatac ctcatgggac agcgcgtcct tccctaaaga ctattgcaag | 3111 |
| tcatacttag gaatttctcc tactttacac tctctgtaca aaacaaaac aaaacaacaa | 3171 |
| caatacaaca agaacaacaa caacaataac aacaatggtt tacatgaaca cagctgctga | 3231 |
| agaggcaaga gacagaatga tatccagtaa gcacatgttt attcatgggt gtcagctttg | 3291 |
| cttttcctgg agtctcttgg tgatggagtg tgcgtgtgtg catgtatgtg tgtgtgtatg | 3351 |
| tatgtgtgtg gtgtgtgtgc ttggtttagg ggaagtatgt gtgggtacat gtgaggactg | 3411 |
| ggggcacctg accagaatgc gcaagggcaa accatttcaa atggcagcag ttccatgaag | 3471 |
| acacgcttaa aacctagaac ttcaaaatgt tcgtattcta ttcaaaagga aatatatata | 3531 |
| tatatatata tatatatata tatatatata aattaaaaag gaaagaaaac taacaaccaa | 3591 |

```
ccaaccaacc aaccaaccac aaaccaccct aaaatgacag ccgctgatgt ctgggcatca    3651
gcctttgtac tctgtttttt taagaaagtg cagaatcaac ttgaagcaag ctttctctca    3711
taacgtaatg attatatgac aatcctgaag aaaccacagg ttccatagaa ctaatatcct    3771
gtctctctct ctctctctct ctctctcttt ttttttttctt tttccttttg ccatggaatc    3831
tgggtgggag aggatactgc gggcaccaga atgctaaagt ttcctaacat tttgaagttt    3891
ctgtagttca tccttaatcc tgacacccat gtaaatgtcc aaaatgttga tcttccactg    3951
caaatttcaa aagccttgtc aatggtcaag cgtgcagctt gttcagcggt tctttctgag    4011
gagcggacac cgggttacat tactaatgag agttgggtag aactctctga tgatgtgttca   4071 gatagtgtaa ttgctacatt ctctgatgta gttaagtatt tacagatgtt aaatggagta    4131
ttttattttt atgtatatac tatacaacaa tgttctttttt tgttacagct atgcactgta   4191
aatgcagcct tcttttcaaa actgctaaat ttttcttaat caagaatatt caaatgtaat    4251
tatgaggtga aacaattatt gtacactaac atatttagaa gctgaactta ctgcttatat    4311
atatttgatt gtaaaaacaa aaagacagtg tgtgtgtctg ttgagtgcaa caagagcaaa    4371
atgatgcttt ccgcacatcc atcccttagg tgagcttcaa tctaagcatc ttgtcaagaa    4431
atatcctagt cccctaaagg tattaaccac ttctgcgata ttttttccaca ttttcttgtc   4491 gcttgttttt ctttgaagtt ttatacactg gatttgttag gggaatgaaa ttttctcatc    4551 taaaatttt ctagaagata tcatgatttt atgtaaagtc tctcaatggg taaccattaa     4611
gaaatgtttt tattttctct atcaacagta gttttgaaac tagaagtcaa aaatctttttt   4671 aaaatgctgt tttgttttaa ttttttgtgat tttaatttga tacaaaatgc tgaggtaata   4731
attatagtat gattttttaca ataattaatg tgtgtctgaa gactatcttt gaagccagta   4791
tttctttccc ttggcagagt atgacgatgg tatttatctg tattttttac agttatgcat    4851
cctgtataaa tactgatatt tcattccttt gtttactaaa gagacatatt tatcagttgc    4911
agatagccta tttattataa attatgagat gatgaaaata ataaagccag tggaaatttt    4971
ctacctagga tgcatgacaa ttgtcaggtt ggagtgtaag tgcttcattt gggaaattca    5031
gcttttgcag aagcagtgtt tctacttgca ctagcatggc ctctgacgtg accatggtgt    5091
tgttcttgat gacattgctt ctgctaaatt taataaaaac ttcagaaaaa cctccatttt    5151
gatcatcagg atttcatctg agtgtggagt ccctggaatg gaattcagta acatttggag    5211
tgtgtattca agtttctaaa ttgagattcg attactgttt ggctgacatg acttttctgg    5271
aagacatgat acacctacta ctcaattgtt cttttccttt ctctcgccca acacgatctt    5331
gtaagatgga tttcaccccc aggccaatgc agctaatttt gatagctgca ttcatttatc    5391
accagcatat tgtgttctga gtgaatccac tgtttgtcct gtcggatgct tgcttgattt    5451
tttggcttct tatttctaag tagatagaaa gcaataaaaa tactatgaaa tgaaagaact    5511
tgttcacagg ttctgcgtta caacagtaac acatctttaa tccgcctaat tcttgttgtt    5571
ctgtaggtta aatgcaggta ttttaactgt gtgaacgcca aactaaagtt tacagtcttt    5631
ctttctgaat tttgagtatc ttctgttgta gaataataat aaaaagacta ttaagagcaa    5691
taaattattt ttaagaaatc gagatttagt aaatcctatt atgtgttcaa ggaccacatg    5751
tgttctctat tttgccttta aattttttgtg aaccaatttt aaatacattc tccttttttgc  5811 cctggattgt tgacatgagt ggaatacttg gtttctttttc ttacttatca aaagacagca   5871
ctacagatat catattgagg attaattttat ccccccctacc cccagcctga caaatattgt   5931
taccatgaag atagttttcc tcaatggact tcaaattgca tctagaatta gtggagcttt    5991
```

-continued

```
tgtatcttct gcagacactg tgggtagccc atcaaaatgt aagctgtgct cctctcattt    6051
ttatttttat ttttttggga gagaatattt caaatgaaca cgtgcacccc atcatcactg    6111
gaggcaaatt tcagcataga tctgtaggat ttttagaaga ccgtgggcca ttgccttcat    6171
gccgtggtaa gtaccacatc tacaattttg gtaaccgaac tggtgcttta gtaatgtgga    6231 ttttttttctt ttttaaaaga gatgtagcag ataattctt ccagtgcaac aaaatcaatt    6291
ttttgctaaa cgactccgag aacaacagtt gggctgtcaa cattcaaagc agcagagagg    6351
gaactttgca ctattggggt atgatgtttg ggtcagttga taaaaggaaa ccttttcatg    6411
cctttagatg tgagcttcca gtaggtaatg attatgtgtc ctttcttgat ggctgtaatg    6471
agaacttcaa tcactgtagt ctaagacctg atctatagat gacctagaat agccatgtac    6531
tataatgtga tgattctaaa tttgtaccta tgtgacagac attttcaata atgtgaactg    6591
ctgatttgat ggagctactt taagatttgt aggtgaaagt gtaatactgt tggttgaact    6651
atgctgaaga gggaaagtga gcgattagtt gagcccttgc cgggccttt ttccacctgc    6711 caattctaca tgtattgttg tggttttatt cattgtatga aaattcctgt gatttttttt    6771
aaatgtgcag tacacatcag cctcactgag ctaataaagg gaaacgaatg tttcaaatct    6831
aaaaaaaaaa aaaaaaaa                                                  6849
```

<210> SEQ ID NO 6
<211> LENGTH: 803
<212> TYPE: PRT
<213> ORGANISM: Homo sapiens

<400> SEQUENCE: 6

```
Met Asp Glu Thr Ser Pro Arg Leu Glu Glu Asp Trp Lys Lys Val Leu
1               5                   10                  15

Gln Arg Glu Ala Gly Trp Gln Cys Ala Ala Leu Val Gly Glu Asp Gln
            20                  25                  30

Pro Leu Cys Pro Asp Leu Pro Glu Leu Asp Leu Ser Glu Leu Asp Val
        35                  40                  45

Asn Asp Leu Asp Thr Asp Ser Phe Leu Gly Gly Leu Lys Trp Cys Ser
    50                  55                  60

Asp Gln Ser Glu Ile Ile Ser Asn Gln Tyr Asn Asn Glu Pro Ser Asn
65                  70                  75                  80

Ile Phe Glu Lys Ile Asp Glu Glu Asn Glu Ala Asn Leu Leu Ala Val
                85                  90                  95

Leu Thr Glu Thr Leu Asp Ser Leu Pro Val Asp Glu Asp Gly Leu Pro
            100                 105                 110

Ser Phe Asp Ala Leu Thr Asp Gly Asp Val Thr Thr Asp Asn Glu Ala
        115                 120                 125

Ser Pro Ser Ser Met Pro Asp Gly Thr Pro Pro Gln Glu Ala Glu
    130                 135                 140

Glu Pro Ser Leu Leu Lys Lys Leu Leu Leu Ala Pro Ala Asn Thr Gln
145                 150                 155                 160

Leu Ser Tyr Asn Glu Cys Ser Gly Leu Ser Thr Gln Asn His Ala Asn
                165                 170                 175

His Asn His Arg Ile Arg Thr Asn Pro Ala Ile Val Lys Thr Glu Asn
            180                 185                 190

Ser Trp Ser Asn Lys Ala Lys Ser Ile Cys Gln Gln Gln Lys Pro Gln
        195                 200                 205
```

```
Arg Arg Pro Cys Ser Glu Leu Leu Lys Tyr Leu Thr Thr Asn Asp Asp
    210                 215                 220
Pro Pro His Thr Lys Pro Thr Glu Asn Arg Asn Ser Ser Arg Asp Lys
225                 230                 235                 240
Cys Thr Ser Lys Lys Lys Ser His Thr Gln Ser Gln Ser Gln His Leu
                245                 250                 255
Gln Ala Lys Pro Thr Thr Leu Ser Leu Pro Leu Thr Pro Glu Ser Pro
            260                 265                 270
Asn Asp Pro Lys Gly Ser Pro Phe Glu Asn Lys Thr Ile Glu Arg Thr
        275                 280                 285
Leu Ser Val Glu Leu Ser Gly Thr Ala Gly Leu Thr Pro Pro Thr Thr
    290                 295                 300
Pro Pro His Lys Ala Asn Gln Asp Asn Pro Phe Arg Ala Ser Pro Lys
305                 310                 315                 320
Leu Lys Ser Ser Cys Lys Thr Val Val Pro Pro Ser Lys Lys Pro
                325                 330                 335
Arg Tyr Ser Glu Ser Ser Gly Thr Gln Gly Asn Asn Ser Thr Lys Lys
                340                 345                 350
Gly Pro Glu Gln Ser Glu Leu Tyr Ala Gln Leu Ser Lys Ser Ser Val
            355                 360                 365
Leu Thr Gly Gly His Glu Glu Arg Lys Thr Lys Arg Pro Ser Leu Arg
    370                 375                 380
Leu Phe Gly Asp His Asp Tyr Cys Gln Ser Ile Asn Ser Lys Thr Glu
385                 390                 395                 400
Ile Leu Ile Asn Ile Ser Gln Glu Leu Gln Asp Ser Arg Gln Leu Glu
                405                 410                 415
Asn Lys Asp Val Ser Ser Asp Trp Gln Gly Gln Ile Cys Ser Ser Thr
            420                 425                 430
Asp Ser Asp Gln Cys Tyr Leu Arg Glu Thr Leu Glu Ala Ser Lys Gln
        435                 440                 445
Val Ser Pro Cys Ser Thr Arg Lys Gln Leu Gln Asp Gln Glu Ile Arg
    450                 455                 460
Ala Glu Leu Asn Lys His Phe Gly His Pro Ser Gln Ala Val Phe Asp
465                 470                 475                 480
Asp Glu Ala Asp Lys Thr Gly Glu Leu Arg Asp Ser Asp Phe Ser Asn
                485                 490                 495
Glu Gln Phe Ser Lys Leu Pro Met Phe Ile Asn Ser Gly Leu Ala Met
            500                 505                 510
Asp Gly Leu Phe Asp Asp Ser Glu Asp Glu Ser Asp Lys Leu Ser Tyr
        515                 520                 525
Pro Trp Asp Gly Thr Gln Ser Tyr Ser Leu Phe Asn Val Ser Pro Ser
    530                 535                 540
Cys Ser Ser Phe Asn Ser Pro Cys Arg Asp Ser Val Ser Pro Pro Lys
545                 550                 555                 560
Ser Leu Phe Ser Gln Arg Pro Gln Arg Met Arg Ser Arg Ser Arg Ser
                565                 570                 575
Phe Ser Arg His Arg Ser Cys Ser Arg Ser Pro Tyr Ser Arg Ser Arg
            580                 585                 590
Ser Arg Ser Pro Gly Ser Arg Ser Ser Arg Ser Cys Tyr Tyr Tyr
        595                 600                 605
Glu Ser Ser His Tyr Arg His Arg Thr His Arg Asn Ser Pro Leu Tyr
    610                 615                 620
```

-continued

| | | | | | | | | | | | | | | |
|---|---|---|---|---|---|---|---|---|---|---|---|---|---|---|
| Val | Arg | Ser | Arg | Ser | Arg | Pro | Tyr | Ser | Arg | Pro | Arg | Tyr | Asp | |
| 625 | | | | 630 | | | | 635 | | | | 640 | | |

| | | | | | | | | | | | | |
|---|---|---|---|---|---|---|---|---|---|---|---|---|
| Ser | Tyr | Glu | Glu | Tyr | Gln | His | Glu | Arg | Leu | Lys | Arg | Glu | Tyr | Arg |
| | | | 645 | | | | | 650 | | | | | 655 |

| | | | | | | | | | | | | |
|---|---|---|---|---|---|---|---|---|---|---|---|---|
| Arg | Glu | Tyr | Glu | Lys | Arg | Glu | Ser | Glu | Arg | Ala | Lys | Gln | Arg | Glu | Arg |
| | | | 660 | | | | | 665 | | | | | 670 |

Gln Arg Gln Lys Ala Ile Glu Glu Arg Arg Val Ile Tyr Val Gly Lys
             675                 680                 685

Ile Arg Pro Asp Thr Thr Arg Thr Glu Leu Arg Asp Arg Phe Glu Val
690                 695                 700

Phe Gly Glu Ile Glu Glu Cys Thr Val Asn Leu Arg Asp Asp Gly Asp
705                 710                 715                 720

Ser Tyr Gly Phe Ile Thr Tyr Arg Tyr Thr Cys Asp Ala Phe Ala Ala
                725                 730                 735

Leu Glu Asn Gly Tyr Thr Leu Arg Arg Ser Asn Glu Thr Asp Phe Glu
                740                 745                 750

Leu Tyr Phe Cys Gly Arg Lys Gln Phe Phe Lys Ser Asn Tyr Ala Asp
                755                 760                 765

Leu Asp Ser Asn Ser Asp Asp Phe Asp Pro Ala Ser Thr Lys Ser Lys
770                 775                 780

Tyr Asp Ser Leu Asp Phe Asp Ser Leu Leu Lys Glu Ala Gln Arg Ser
785                 790                 795                 800

Leu Arg Arg

```
<210> SEQ ID NO 7
<211> LENGTH: 5223
<212> TYPE: DNA
<213> ORGANISM: Homo sapiens
<220> FEATURE:
<221> NAME/KEY: CDS
<222> LOCATION: (406)..(1050)

<400> SEQUENCE: 7
```

| | |
|---|---|
| ggggtgaggc cgccgccgcg gtccctccat caccctcctg gcccggcaga ggaacccact | 60 |
| gctccgggcg gccggggaca gaggtggctc aacagcgccg cctcgaagcc agagccctcc | 120 |
| gcaggctaga ggattgcggt ttcccttcat ctccgcggct cttattcctc ccccgcaagg | 180 |
| ccgcccaccg gggtacgctc tcccgcgcct gcgccaattc cgccccgccc cgccccatc | 240 |
| taccgaccgg atgttagcag atttcccata gtgcctcgct agtggcgggc atgataacac | 300 |
| acgccggagg gtcgcacgcg ggttccagtt gtgattgctg gagttgtgta ttgccaggag | 360 |
| gctctccgag attggggtcg ggtcactgcc tcatccaccg gagcg atg gcg ttt ctc | 417 |
|                                                                                     Met Ala Phe Leu | |
|                                                                                                 1 | |
| cga agc atg tgg ggc gtg ctg agt gcc ctg gga agg tct gga gca gag | 465 |
| Arg Ser Met Trp Gly Val Leu Ser Ala Leu Gly Arg Ser Gly Ala Glu | |
| 5                   10                 15                 20 | |
| ctg tgc acc ggc tgt gga agt cga ctg cgc tcc ccc ttc agt ttt gtg | 513 |
| Leu Cys Thr Gly Cys Gly Ser Arg Leu Arg Ser Pro Phe Ser Phe Val | |
|                   25                 30                 35 | |
| tat tta ccg agg tgg ttt tca tct gtc ttg gca agt tgt cca aag aaa | 561 |
| Tyr Leu Pro Arg Trp Phe Ser Ser Val Leu Ala Ser Cys Pro Lys Lys | |
|                            40                 45                 50 | |
| cct gta agt tct tac ctt cga ttt tct aaa gaa caa cta ccc ata ttt | 609 |
| Pro Val Ser Ser Tyr Leu Arg Phe Ser Lys Glu Gln Leu Pro Ile Phe | |
| 55                  60                 65 | |

```
aaa gct cag aac cca gat gca aaa act aca gaa cta att aga aga att     657
Lys Ala Gln Asn Pro Asp Ala Lys Thr Thr Glu Leu Ile Arg Arg Ile
    70              75                  80 gcc cag cgt tgg agg gaa ctt cct gat tca aag aaa aaa ata tat caa     705
Ala Gln Arg Trp Arg Glu Leu Pro Asp Ser Lys Lys Lys Ile Tyr Gln
 85              90                  95                 100 gat gct tat agg gcg gag tgg cag gta tat aaa gaa gag ata agc aga     753
Asp Ala Tyr Arg Ala Glu Trp Gln Val Tyr Lys Glu Glu Ile Ser Arg
                105                 110                 115 ttt aaa gaa cag cta act cca agt cag att atg tct ttg gaa aaa gaa     801
Phe Lys Glu Gln Leu Thr Pro Ser Gln Ile Met Ser Leu Glu Lys Glu
            120                 125                 130 atc atg gac aaa cat tta aaa agg aaa gct atg aca aaa aaa aaa gaa     849
Ile Met Asp Lys His Leu Lys Arg Lys Ala Met Thr Lys Lys Lys Glu
        135                 140                 145 aag ctg aag act gta aag gaa aac tgg aaa aat ctg tct gac tct gaa     897
Lys Leu Lys Thr Val Lys Glu Asn Trp Lys Asn Leu Ser Asp Ser Glu
    150                 155                 160 aag gaa tta tat att cag cat gct aaa gag gac gaa act cgt tat cat     945
Lys Glu Leu Tyr Ile Gln His Ala Lys Glu Asp Glu Thr Arg Tyr His
165             170                 175                 180 aat gaa atg aag tct tgg gaa gaa caa atg att gaa gtt gga cga aag     993
Asn Glu Met Lys Ser Trp Glu Glu Gln Met Ile Glu Val Gly Arg Lys
                185                 190                 195 gat ctt cta cgt cgc aca ata aag aaa caa cga aaa tat ggt gct gag    1041
Asp Leu Leu Arg Arg Thr Ile Lys Lys Gln Arg Lys Tyr Gly Ala Glu
            200                 205                 210 gag tgt taa aagtagaaga ttgagatgtg ttcacaatgg ataggcacag             1090
Glu Cys gaaaccagtt aggtctcaat acctgaagct atcgtaaaat taagaaagga taaagttggt   1150
aaacctttta tatttagtat cttttttattc agctcatgga cttctgccag cataatactt  1210
gctttggaaa acccagataa aggttcatgc aaactttatt ttgtgtttag gaactactga   1270
ggatcagagt aatccaagca aatgtgaatc attttacctt tgacaaaggt aaatcagact   1330
atgaagtttt ttttatacag gatgatgact atggaaagag tactcttgtt tccttatatt   1390
atggaggcag gagtttcgtt ttcaaaattg ttacaaattg tagaagccac ggtgttctgt   1450
gatataagtg tgtgttttttc ataaagcagg cagaactcat ctaggtaaat tacagttcct  1510
aggtataatt cacattgtat tcagagttga tggttgtaca tataagtgat tgctggtttt   1570
agttgcaact ttgtataaaa gggactgaga aattttataaa cttttttctt actgtctttt  1630
ttctaaagta aaaacaaaga aattatgtgc cagatttatg catattattt tatgttgcat   1690
agaataaaat ttttaatctt taatttttaca tttcctaaat atattttaag acgaaacatt  1750
tgttctatag ctttttccctt tttttaagta aggaatttta ttttttttctg aattattttc 1810 tctcgtgagt atattgatcc agaaagaaaa cttgtattat gtgtgttttta aaatgagaaa 1870 tctaaaaaac gaaaagtctc caaagtctct ggaatttgaa acactttgca taacgtataa   1930
aagcctgttt aagagacagc caactatggc ctgtggatca aatccagcct gctgcctgct   1990
ttttatggcc tgtgagctag gaattgtgtt tataatttta aatgtttttt tttaaagact   2050
tttatgatac ttgaaaatta acatgaatat ttagtgttca taaataaagt tgttgaaac    2110 acaaccaaga tcattctttt acttgtctat ggctgctttt ctgtggcaga gtagctgcca   2170
cagaaactat agcccacaaa gcctgatatt tactgtctgt ctgtttatgg aaaaaattta   2230
tcaacccatg gtctatagta tagtgtgata tgactactgt tccaatgtat tgaagtgttg   2290
```

```
ggatagtttt ttcaaatgtt ttcagatgtt cttgttttag aatcattgtc acctttaaga    2350
ggaaaaaggt catcactaga taatctaaac aaattgttgc ttctcagtgt tagcaaggaa    2410
aataatctag tttcaaatta cattgcagta taatgaaaaa gatccatata ctgtggaatg    2470
atattctttt aaaattattt gctatggctt ggtaaaaatg tacttttttcc agtagcacat   2530 atcacaagaa cctcactgta gttgaaagcc atctttcttt agtatttgtt tatccttta    2590 ggagagtcaa gcaaaggttt tcaccacctg tttgagcaga ataattctca tcagttcaca    2650
gatataggat aactcaattt atatgcactt tatgcgttat gcaaatatt tagaaattgt     2710 agattctaga tctccagaaa gactttgaag actttgatgt cacaaaaaga tgacttgtta    2770
tatgctgagc ttgacaaagg taggaatggg agagaaaaat agtagcttat gaggaaatat    2830
gaggctttaa atatataaag ttggatattt taaaataact ttccctgtg ggagcttctc     2890 actctgggtg cagacaggac agtgttggcc attggtgaaa tagataggat gggtttgagg    2950
ccagagcagt ctgggagtag ggggaaagag aaggaggtgt gctagtgtct atcacaggct    3010
ttctcaatta ggtttgcagg agaaaaagcc ctaagtccct gtgtcatcta gaatggtact    3070
aattatgtac agtccctagg agaatggaga aaatcataac tcaaatcatc gactcaattc    3130
tgttctcttc agatgagctc agagagcaca taggagtgtt tgtaatgagg ggtatgtaat    3190
gattgagata gaggaatgag ttacataaac atctcgggac aaatgcagca tagaaaacat    3250
ctttgtagtt accctgcggg gaaatttcct ctgagttctt ttaacattaa ctacccgtat    3310
tattttatac ttaacattca tatcatacct tcccaaatat attgggaagt tcagtgttaa    3370
gtacgtttct caagtactta acaacttaat atagggagga aaggtgtaaa cagtgaaaaa    3430
agagcaaaac tatttatgg taattttatg gtagtatcag cttgtatttg gttctctgtt    3490
tctaaaataa tgtaattttt aatattttaa ataataggat aacctggttt ccaagccttt    3550
ttttcccccg acatccagaa tacacactgg atccaagcct ttcttaaaca tcagtacatg    3610
tggaagactg gcatgccata taccaaatgc cattcagctg taacagtata cacagatttt    3670
ctcttataaa gaataagaac atcataacca atgaccactc atataaagtc ttatttgtgt    3730
gtgtgtgtgt gtgtgtgtgc acgtgtgtgt gttagagtct cattatattg ctcaggctgg    3790
agggcatggt gtgatcttgg ctcactgcag ccttgacctc ctgggctcaa gtgatccttc    3850
cgagtcgttg gactacagt aggtgaacac caccatgcct ggctaatttt tgtattttt     3910 ttttaatcaa gatgggatct tgctatgttg cccaggctgg tctcaaactc ctggcatcaa    3970
gcgttcctcc ttccttggcc tccttaagtg ctgggattat aggtgtgagc caccatgctt    4030
gaccataaag ccttactatt tcttttggag acacagtctt gctctgtcca agctggaatg    4090
cagtgatgtg atcatggctc actgcagcct tgaactccca ggcttaagag atcctcccat    4150
ctcagcctcc tgagtagctg ggattatagg tgcagaccat caagccttgc tattattttt    4210
tagacttttc ttaatttcat ccaacaaagt agttgctgta ggagctgagt gttagaagga    4270
aagatgctga agaaatgaaa tcaagcaggg tgtatactgt catgaatagg catacagtag    4330
tttttatact tttgttcttt ggagtaccaa tgttaggttt tacaaaagta atttgatgag    4390
gggaaggagg gttgtgtatt tattttactt tctgatgttt gcttaaataa tactgtgtac    4450
gtattcagct tgctgtaatt ctgtaattac gctattgcgt ttggctaact ccttttttgga   4510 aatgtctttt tttttgtaca aggcatgtgt tagttttttac taattgctct gaatgtgtat    4570
atttagattt ctgaattgaa aaaaaatagc gtacaataag tagatttaaa gtaattagaa    4630
```

-continued

```
cactttattg attttctga tgttttctgt atctaaaatt tatcaccacc aggttgtgct    4690
aaaacagcag gaagtttta tattgtgagt gacagtaccc attatttctc ttaattttac    4750
taacatttac tataagaata ttctctcgct ctttctcca ctcacagcca ttctccctcc    4810
ttctcttcat aacatcaagc tgtcacagac aaatctgaaa atgttacaag cacagactat    4870
gttgtatgtt ttgaaatttt agaacagtaa tgttcttttt aaaattgaac ttctgcagag    4930
taagaaaatg aatacattta ttactttaaa tttgtaaaat tttccaaagt aaaaccatac    4990
aaagctagtg tcagtctctc tcattgttca caaataaagg acttttgtta attgattaaa    5050
tcacttacta tattcgatat gaaatatata aaacatacaa ccattatcta atacatttca    5110
gaatgtttca ctggttacag gagccagtaa ataaagttga ctctaaacag gaattttaaa    5170
taaactaaac atttttcat caccaagcat catttaaaaa aaaaaaaaa aaa              5223
```

<210> SEQ ID NO 8
<211> LENGTH: 214
<212> TYPE: PRT
<213> ORGANISM: Homo sapiens

<400> SEQUENCE: 8

```
Met Ala Phe Leu Arg Ser Met Trp Gly Val Leu Ser Ala Leu Gly Arg
1               5                   10                  15

Ser Gly Ala Glu Leu Cys Thr Gly Cys Gly Ser Arg Leu Arg Ser Pro
                20                  25                  30

Phe Ser Phe Val Tyr Leu Pro Arg Trp Phe Ser Ser Val Leu Ala Ser
            35                  40                  45

Cys Pro Lys Lys Pro Val Ser Ser Tyr Leu Arg Phe Ser Lys Glu Gln
        50                  55                  60

Leu Pro Ile Phe Lys Ala Gln Asn Pro Asp Ala Lys Thr Thr Glu Leu
65                  70                  75                  80

Ile Arg Arg Ile Ala Gln Arg Trp Arg Glu Leu Pro Asp Ser Lys Lys
                85                  90                  95

Lys Ile Tyr Gln Asp Ala Tyr Arg Ala Glu Trp Gln Val Tyr Lys Glu
            100                 105                 110

Glu Ile Ser Arg Phe Lys Glu Gln Leu Thr Pro Ser Gln Ile Met Ser
        115                 120                 125

Leu Glu Lys Glu Ile Met Asp Lys His Leu Lys Arg Lys Ala Met Thr
    130                 135                 140

Lys Lys Lys Glu Lys Leu Lys Thr Val Lys Glu Asn Trp Lys Asn Leu
145                 150                 155                 160

Ser Asp Ser Glu Lys Glu Leu Tyr Ile Gln His Ala Lys Glu Asp Glu
                165                 170                 175

Thr Arg Tyr His Asn Glu Met Lys Ser Trp Glu Glu Gln Met Ile Glu
            180                 185                 190

Val Gly Arg Lys Asp Leu Leu Arg Arg Thr Ile Lys Lys Gln Arg Lys
        195                 200                 205

Tyr Gly Ala Glu Glu Cys
    210
```

<210> SEQ ID NO 9
<211> LENGTH: 798
<212> TYPE: PRT
<213> ORGANISM: Homo sapiens

<400> SEQUENCE: 9

```
Met Ala Trp Asp Met Cys Asn Gln Asp Ser Glu Ser Val Trp Ser Asp
1               5                   10                  15

Ile Glu Cys Ala Ala Leu Val Gly Glu Asp Gln Pro Leu Cys Pro Asp
            20                  25                  30

Leu Pro Glu Leu Asp Leu Ser Glu Leu Asp Val Asn Asp Leu Asp Thr
        35                  40                  45

Asp Ser Phe Leu Gly Gly Leu Lys Trp Cys Ser Asp Gln Ser Glu Ile
    50                  55                  60

Ile Ser Asn Gln Tyr Asn Asn Glu Pro Ser Asn Ile Phe Glu Lys Ile
65                  70                  75                  80

Asp Glu Glu Asn Glu Ala Asn Leu Leu Ala Val Leu Thr Glu Thr Leu
                85                  90                  95

Asp Ser Leu Pro Val Asp Glu Asp Gly Leu Pro Ser Phe Asp Ala Leu
            100                 105                 110

Thr Asp Gly Asp Val Thr Thr Asp Asn Glu Ala Ser Pro Ser Ser Met
        115                 120                 125

Pro Asp Gly Thr Pro Pro Gln Glu Ala Glu Glu Pro Ser Leu Leu
130                 135                 140

Lys Lys Leu Leu Leu Ala Pro Ala Asn Thr Gln Leu Ser Tyr Asn Glu
145                 150                 155                 160

Cys Ser Gly Leu Ser Thr Gln Asn His Ala Asn His Asn His Arg Ile
                165                 170                 175

Arg Thr Asn Pro Ala Ile Val Lys Thr Glu Asn Ser Trp Ser Asn Lys
            180                 185                 190

Ala Lys Ser Ile Cys Gln Gln Gln Lys Pro Gln Arg Arg Pro Cys Ser
        195                 200                 205

Glu Leu Leu Lys Tyr Leu Thr Thr Asn Asp Asp Pro His Thr Lys
210                 215                 220

Pro Thr Glu Asn Arg Asn Ser Ser Arg Asp Lys Cys Thr Ser Lys Lys
225                 230                 235                 240

Lys Ser His Thr Gln Ser Gln Ser Gln His Leu Gln Ala Lys Pro Thr
                245                 250                 255

Thr Leu Ser Leu Pro Leu Thr Pro Glu Ser Pro Asn Asp Pro Lys Gly
            260                 265                 270

Ser Pro Phe Glu Asn Lys Thr Ile Glu Arg Thr Leu Ser Val Glu Leu
        275                 280                 285

Ser Gly Thr Ala Gly Leu Thr Pro Thr Thr Pro Pro His Lys Ala
290                 295                 300

Asn Gln Asp Asn Pro Phe Arg Ala Ser Pro Lys Leu Lys Ser Ser Cys
305                 310                 315                 320

Lys Thr Val Val Pro Pro Ser Lys Lys Pro Arg Tyr Ser Glu Ser
                325                 330                 335

Ser Gly Thr Gln Gly Asn Asn Ser Thr Lys Lys Gly Pro Glu Gln Ser
            340                 345                 350

Glu Leu Tyr Ala Gln Leu Ser Lys Ser Ser Val Leu Thr Gly Gly His
        355                 360                 365

Glu Glu Arg Lys Thr Lys Arg Pro Ser Leu Arg Leu Phe Gly Asp His
370                 375                 380

Asp Tyr Cys Gln Ser Ile Asn Ser Lys Thr Glu Ile Leu Ile Asn Ile
385                 390                 395                 400
```

```
Ser Gln Glu Leu Gln Asp Ser Arg Gln Leu Glu Asn Lys Asp Val Ser
                405                 410                 415
Ser Asp Trp Gln Gly Gln Ile Cys Ser Ser Thr Asp Ser Asp Gln Cys
            420                 425                 430
Tyr Leu Arg Glu Thr Leu Glu Ala Ser Lys Gln Val Ser Pro Cys Ser
        435                 440                 445
Thr Arg Lys Gln Leu Gln Asp Gln Glu Ile Arg Ala Glu Leu Asn Lys
    450                 455                 460
His Phe Gly His Pro Ser Gln Ala Val Phe Asp Asp Glu Ala Asp Lys
465                 470                 475                 480
Thr Gly Glu Leu Arg Asp Ser Asp Phe Ser Asn Glu Gln Phe Ser Lys
                485                 490                 495
Leu Pro Met Phe Ile Asn Ser Gly Leu Ala Met Asp Gly Leu Phe Asp
            500                 505                 510
Asp Ser Glu Asp Glu Ser Asp Lys Leu Ser Tyr Pro Trp Asp Gly Thr
        515                 520                 525
Gln Ser Tyr Ser Leu Phe Asn Val Ser Pro Ser Cys Ser Ser Phe Asn
    530                 535                 540
Ser Pro Cys Arg Asp Ser Val Ser Pro Pro Lys Ser Leu Phe Ser Gln
545                 550                 555                 560
Arg Pro Gln Arg Met Arg Ser Arg Ser Arg Ser Phe Ser Arg His Arg
                565                 570                 575
Ser Cys Ser Arg Ser Pro Tyr Ser Arg Ser Arg Ser Arg Ser Pro Gly
            580                 585                 590
Ser Arg Ser Ser Ser Arg Ser Cys Tyr Tyr Tyr Glu Ser Ser His Tyr
        595                 600                 605
Arg His Arg Thr His Arg Asn Ser Pro Leu Tyr Val Arg Ser Arg Ser
    610                 615                 620
Arg Ser Pro Tyr Ser Arg Arg Pro Arg Tyr Asp Ser Tyr Glu Glu Tyr
625                 630                 635                 640
Gln His Glu Arg Leu Lys Arg Glu Glu Tyr Arg Arg Glu Tyr Glu Lys
                645                 650                 655
Arg Glu Ser Glu Arg Ala Lys Gln Arg Glu Arg Gln Arg Gln Lys Ala
            660                 665                 670
Ile Glu Glu Arg Arg Val Ile Tyr Val Gly Lys Ile Arg Pro Asp Thr
        675                 680                 685
Thr Arg Thr Glu Leu Arg Asp Arg Phe Glu Val Phe Gly Glu Ile Glu
    690                 695                 700
Glu Cys Thr Val Asn Leu Arg Asp Asp Gly Asp Ser Tyr Gly Phe Ile
705                 710                 715                 720
Thr Tyr Arg Tyr Thr Cys Asp Ala Phe Ala Ala Leu Glu Asn Gly Tyr
                725                 730                 735
Thr Leu Arg Arg Ser Asn Glu Thr Asp Phe Glu Leu Tyr Phe Cys Gly
            740                 745                 750
Arg Lys Gln Phe Phe Lys Ser Asn Tyr Ala Asp Leu Asp Ser Asn Ser
        755                 760                 765
Asp Asp Phe Asp Pro Ala Ser Thr Lys Ser Lys Tyr Asp Ser Leu Asp
    770                 775                 780
Phe Asp Ser Leu Leu Lys Glu Ala Gln Arg Ser Leu Arg Arg
785                 790                 795
```

GENETIC RE-ENGINEERING OF IMMUNE CELLS TO IMPROVE METABOLIC FITNESS FOR IMMUNOTHERAPY

CROSS-REFERENCE TO RELATED APPLICATIONS

This is the U.S. National Stage of International Application No. PCT/US2017/039252, filed Jun. 26, 2017, which was published in English under PCT Article 21(2), which in turn claims the benefit of U.S. Provisional Application No. 62/354,338 filed Jun. 24, 2016. The provisional application is incorporated herein in its entirety.

FIELD

The present disclosure provides recombinant T cells that have increased expression of PGC1α, TFAM, GABPA, and ERRα, and methods of their use, for example in the treatment of a tumor. Also provided are kits and compositions that can be used with such methods.

BACKGROUND

The immune system has evolved multiple cellular mechanisms for the detection and elimination of abnormal or stressed cells in a wide array of environments. Early detection of cancer, via immunosurveillance, can occur almost anywhere, facilitating destruction of early transformed cells expressing neoantigen. However, as cancers immunoedit and escape this initial immune detection, they also generate an extraordinarily immunosuppressive microenvironment which restricts T cell infiltration, activation, and effector function both through direct repression (via cytokines, adenosine, prostaglandins, glucose restriction, etc.) as well as the recruitment of immunosuppressive populations tasked with maintaining immune tolerance (Jiang et al., 2015). The result is an ineffectual antitumor immune response and consequent tumor progression.

Recent advances in cancer immunotherapy have revealed that the T cell response to cancer can be reinvigorated in a variety of ways, resulting in durable and effective benefit in a wide array of cancer types (La-Beck et al., 2015; Mahoney et al., 2015; Ribas, 2015). These include engineering chimeric antigen receptors to better target T cells to tumor antigens, personalized antigen vaccines to persistent neoepitopes, and, probably most prominently, antibody-mediated blockade of co-inhibitory 'checkpoint' molecules, like programmed death-1 (PD-1), cytotoxic T lymphocyte antigen 4 (CTLA-4), lymphocyte activation gene 3 (LAG-3), T cell immunoglobulin and mucin-containing gene 3 (Tim-3), among others (La-Beck et al., 2015). These molecules are highly upregulated on tumor-infiltrating T cells and are thought to act to negatively regulate T cell activation and effector function. This elevated and sustained expression of co-inhibitory molecules is indicative of a hyporesponsive phenotype, originally discovered in chronic viral infection, termed T cell 'exhaustion' (Wherry and Kurachi, 2015). Thought to occur from chronic activation and inflammation, antigen persistence results in continued TCR and cytokine signals, which promote upregulation of these receptors, resulting a hyporesponsiveness functionally similar to anergy but mechanistically distinct (Crespo et al., 2013; Schietinger and Greenberg, 2014). Importantly, T cells can still have an exhausted phenotype in the absence of co-inhibitory molecules (Legat et al., 2013; Odorizzi et al., 2015), shedding light on the fact that while these co-inhibitory molecules have been extensively studied at the molecular and biochemical levels, it is still unclear what the contribution of co-inhibitory molecule signaling is to the initiation and/or maintenance of the exhausted phenotype. Thus for improving the treatment of cancer, chronic viral infections, and other diseases, it is critical to understand the mechanisms behind the dysfunction in chronically activated T cells (Pauken and Wherry, 2015). This is especially important considering that, while checkpoint blockade has had remarkable success in the clinic, the majority of patients still do not respond to these therapies (La-Beck et al., 2015).

Carrying out effector function is a metabolically demanding process (Pearce et al., 2013). T cells must efficiently divide and replicate their genome very rapidly and with fidelity, synthesize high levels of cytokines, and deliver cytotoxic payload to target cells. Recent discoveries of T cells' dependence on nutrient sensing and availability and flux through various glycolytic pathways have shown that metabolism represents a key mechanism by which the immune system can be regulated (Delgoffe and Powell, 2015). They also suggest that the fate and function of T cells are intrinsically tied to their metabolism, and that a T cell (like any other cell) requires the machinery to generate bioenergetic intermediates to support proliferation and effector function (Delgoffe and Powell, 2015).

T cells utilize aerobic glycolysis, diverting glucose into cytosolic lactate fermentation rather than mitochondrial acetyl-CoA oxidation to support their expansion and proliferation during their effector phase (Pearce et al., 2013; Roos and Loos, 1970). The precise contributions of this pathway and teleologic reasoning for its function remain the subject of much study, but nevertheless the mitochondria remain an essential component of T cell metabolism. Effector T cells significantly upregulate oxidative phosphorylation activity and memory T cell precursors become increasingly dependent on mitochondria to mediate fatty acid oxidation over time (van der Windt et al., 2012; van der Windt et al., 2013). Furthermore, the mitochondria remain important organelles for biosynthesis, calcium buffering, and mediating programmed cell death (Rizzuto et al., 2012; Wenner, 2012). Thus, while T cells may divert glucose metabolism away from mitochondrial pathways during activation, mitochondria are still critical for maintaining the health and integrity of the T cell in both effector and memory phases.

While the effects of glucose deprivation in tumor microenvironments on glycolytic metabolism and T cell function have garnered much recent interest, the mitochondrial phenotype of T cells infiltrating tumors remains unclear (Chang et al., 2015; Ho et al., 2015; Siska and Rathmell, 2015; Zhao et al., 2015).

SUMMARY

It is shown herein that T cells infiltrating solid tumors display an overall phenotype of metabolic insufficiency, characterized most prominently by a crippling loss of mitochondrial function and mass. Loss of mitochondrial function in tumor-reactive T cells occurs specifically in the tumor microenvironment, largely independently of PD-1 blockade, and due to a defect in PPAR-gamma coactivator 1α (PGC1α)-programmed mitochondrial biogenesis. This defect is due in part to chronic Akt signaling, which represses Foxo transcription factor activity and consequent PGC1α expression. Metabolic reprogramming of T cells through enforced PGC1α expression rescues mitochondrial function, intratumoral T cell proliferation, and a superior antitumor response characterized by cytokine production and tumor control.

Provided herein are recombinant T cells that can be used to improve cellular immunotherapy, such as chimeric antigen receptor (CAR) T cell therapy or T cell receptor (TCR) gene therapy. For example, the disclosure provides recombinant T cells containing a vector that encodes one or more of peroxisome proliferator-activated receptor (PPAR) gamma coactivator 1-alpha (PGC1α), mitochondrial transcription factor A (Tfam), GA binding protein transcription factor alpha subunit GABPA), and estrogen-related receptor alpha (ERRα). Expression of the vector in the T cell results in increased expression of one or more of these genes, and thus increased activity of these proteins. In some examples, the PGC1α, Tfam, GABPA, and/or ERRα expressed from the vector is a variant sequence that encodes a protein that is resistant to negative regulation. For example, the PGC1α resistant to negative regulation may include a S572A mutation (based on the human sequence, S571A in mouse), the Tfam resistant to negative regulation may include a S55A, S56A, and/or S61A (see e.g., Lu et al., *Molecular Cell* 49:121-32, 2013) mutation, the GABPA resistant to negative regulation may include a T280E mutation (see e.g., Jain and Jaiswal, *J. Biol. Chem.* 281:12132-42, 2006), and the ERRα resistant to negative regulation may include a S19A mutation (see e.g., Tremblay et al., *Mol. Endocrinol.* 22:570-84, 2008).

The recombinant T cell expressing PGC1α, Tfam, GABPA, and/or ERRα may also include a chimeric antigen receptor (CAR), or a recombinant T cell receptor (TCR) (such as a TCR that targets the T cells to a tumor cells, such as WT1 for acute myeloid leukemia and chronic myeloid leukemia). The CAR or recombinant TCR can be expressed from the same or a different vector than the PGC1α, Tfam, GABPA, and/or ERRα.

The vectors used to generate such recombinant T cells, such as a vector that includes a nucleic acid molecule encoding one or more of PGC1α, Tfam, GABPA, and ERRα and a nucleic acid molecule encoding a CAR a recombinant TCR, are provided herein. Examples of vectors that can be used include viral vectors, such as a lentiviral vector or retrovirus.

Also provided are methods for producing such recombinant T cells, for example ex vivo. T cells used for such methods can be obtained from a subject having cancer that will later receive the generated recombinant T cells, or from a donor subject. Such methods can include introducing the vector encoding one or more of PGC1α, Tfam, GABPA, and ERRα (which may also encode a CAR or TCR), into a T cell, thereby generating the recombinant T cell. In some examples, a separate vector encoding a CAR or TCR is introduced into the T cell, thereby generating the recombinant T cell. Such methods can further include culturing or growing the transformed recombinant T cells under conditions that permit expression of one or more of PGC1α, Tfam, GABPA, and ERRα (and in some examples also a CAR or TCR). In some examples, the recombinant T cells are incubated or culture in the presence of interleukin 2 (IL-2), interleukin 15 (IL-15), and/or interleukin 7 (IL-7). In some examples, the recombinant T cells are cultured for a period of days or weeks (such as at least 1 week, at least 2 weeks, at least 3 weeks, at least 4 weeks, or at least 6 weeks). In some examples, the method includes monitoring the recombinant T cells, for example determining the number of cells, determining or measuring the mitochondrial activity and/or mass of the recombinant T cells, and/or determining or measuring expression of one or more of PGC1α, PD-1, LAG-3, Tim-3, PGC1α, Tfam, GABPA, ERRα, CAR, and TCR.

The disclosed recombinant T cells can be used in cancer immunotherapy, for example to treat a tumor in vivo. Both solid and liquid tumors can be treated, such as a leukemia, lymphoma, colorectal cancer, melanoma, cervical cancer, lung cancer, ovarian cancer, bladder cancer, breast cancer, or head and neck cancer. For example, effective amount of the recombinant T cells are administered to the subject, thereby treating a tumor (such as a primary tumor and/or a metastasis) in the subject. In some examples, such subjects are also administered an effective amount of IL-2 to the subject before, after, or both before and after, administering the recombinant T cells. In some examples, the subject is administered an effective amount of nonmyeloablative chemotherapy or radiotherapy to deplete native lymphocytes prior to administering an effective amount of the disclosed recombinant T cells. In some examples, the subject is also treated with an effective amount of chemotherapy, radiation therapy, biologic therapy, or combinations thereof. Such methods can treat the tumor in the subject by reducing the volume or weight of the tumor, reducing the number of metastases, reducing the size or weight of a metastasis, or combinations thereof. In some examples the subject administered the disclosed recombinant T cells was previously treated unsuccessfully with a chemotherapy, radiation therapy, biologic therapy, or combinations thereof (e.g., the tumor in the subject did not significantly decrease in size or even increased in size, and/or metastasized). In some examples the subject has a tumor that was not responsive to a PD-1 antagonist or a PD-L1 antagonist (e.g., the tumor in the subject did not significantly decrease in size or even increased in size, and/or metastasized), such as an antibody that specifically binds PD-1 or PD-L1, such as Atezolizumab, MPDL3280A, BNS-936558 (Nivolumab), Pembrolizumab, Pidilizumab, CT011, AMP-224, AMP-514, MEDI-0680, BMS-936559, BMS935559, MEDI-4736, MPDL-3280A, MSB-0010718C.

Also provided are compositions and kits that can be used with the disclosed methods. In some examples, the composition or kits include recombinant T cells and/or vectors disclosed herein, for example in combination with a pharmaceutically acceptable carrier. In one example, the kit, further includes one or more of a transfection reagent, culture medium, antibiotic, IL2, IL15, IL7, anti-CD3, and anti-CD28 (e.g., anti-CD3/anti-CD28 stimulatory beads). In some examples, in a kit, such reagents are present in a separate container.

The foregoing and other objects and features of the disclosure will become more apparent from the following detailed description, which proceeds with reference to the accompanying figures.

BRIEF DESCRIPTION OF THE DRAWINGS

FIGS. 1A-1E. (A) MitoTracker Deep Red FM, MitoTracker Green FM, and TMRE staining of CD8$^+$ T cells from spleen and LNs. The indicated histogram represents T cells pre-incubated with 100-111 μM CCCP, which collapses membrane potential. Results from CCCP titration are tabulated below. (B) MitoTracker Green FM and intracellular VDAC staining of LN and TIL from d14 B16 tumors as in FIG. 1A. (C) MitoTracker Deep Red FM staining of naïve (CD62L$^{hi}$CD44$^{lo}$), effector memory (CD62L$^{lo}$CD44$^{hi}$), and central memory (CD62L$^{hi}$CD44$^{hi}$) CD8$^+$ T cells from LN and tumor-infiltrating compartments. (D) 2NBDG uptake and MitoTracker FM staining measurements from CD8+ and CD4+ T cells infiltrating day 18 MC38 tumors or (E) LLC tumors or from the nondraining or draining LN. Results represent 3 (A, B, D, E), or 6 (C) independent experiments. p<0.01, *p<0.001 by unpaired (B) or paired (C) t test. Error bars indicate s.e.m.

FIGS. 3A-3D. Loss of mitochondrial function and mass is not simply a phenotype of robust activation in vivo. (A), Representative flow cytogram and tabulated results of 2NBDG uptake and MitoTracker FM measurements of OT-I T cells injected into B16$^{OVA}$-bearing or VV$^{OVA}$-infected, or uninfected congenically mismatched hosts for 6 d. Plots are gated on CD8+ T cells and the congenic allele marker (Thy 1). (B) Seahorse measurements (OCR, SRC, and ECAR) from cells in A. (C) ATP measurements from purified donor cells from A. (D) Flow cytogram of glucose uptake and mitochondrial mass of OT-I (Thy1.1+) T cells adoptively transferred into B16$^{OVA}$ bearing mice for 6 days, isolated from either LN or tumor, then transferred into VV$^{OVA}$-infected mice for 6 days. Flow cytogram depicts splenic CD8+ Thy1.1+ cells. *, p<0.05, p<0.01, *p<0.001 by unpaired t-test. Results represent four (A-C) or three (D) experiments. Circles represent individual animals. UI=uninfected V$^{OVA}$=VV$^{OVA}$-infected (1×10$^6$ PFU IP), spl=spleen. Error bars indicate s.e.m.

FIGS. 4A-4B. Tumor infiltrating T cells do not efficiently elaborate cytokines. (A) Cytokine production of OT-I T cells injected as in FIG. 3. Some were rechallenged with peptide overnight and others were stimulated with PMA/ionomycin, as tabulated below from TIL or spleen of VV$^{OVA}$ infected mice. (B) VDAC staining of OT-I T cells transferred as in A. Error bars indicate s.e.m.

FIGS. 5A-5E. T cell mitochondrial dysfunction is induced upon entry into the tumor microenvironment. (A) Representative flow cytogram and tabulated data of LN and TIL of naïve, CTV-labeled, OT-I (Thy 1.1+) CD8+ T cells transferred into B16$^{OVA}$-bearing mice (5-7 mm tumors), or the spleens of the same progenitor cells transferred into B6 mice infected with 1×10$^6$ PFU VV$^{OVA}$ for 72 h. Cells were stained with MitoTracker Deep Red FM. (B) As in A, but with the mitochondrial membrane potential dye TMRE. (C) As in A, but with the cellular ROS indicator DCFDA. (D) As in A, but cells were permeabilized and stained intracellularly for LC3B. (E) Representative data from experiments as in A, but some mice received mitophagy inhibitor m-divi-1. Results represent the mean of three or four independent experiments, with n=7-9 mice per group. p<0.01, *p<0.001, ***p<0.0001 by two-way ANOVA. Error bars indicate s.e.m.

FIGS. 7A-7G. Mitochondrial dysfunction in intratumoral T cells is progressive and correlates with coinhibitory molecule expression in mouse and human tumors. (A), Representative flow cytogram of CD8+ T cells isolated from d14 B16-bearing C57/BL6 mice. (B) Flow cytogram showing mitochondrial mass and glucose competency of CD8+ T cell subsets. (C,D) Tabulated data from B. (E) ATP measurements from CD8+ T cells sorted directly ex vivo from tumors based on the indicated expression. Results are compared to LN CD8+CD44$^{hi}$ cells (T$_{eff}$). (F) Cytogram of coinhibitory molecules and (G) mitochondrial/glucose status of CD8+ cells from PBMC or TIL from HNSCC patients. Data represent the mean or are representative of 3-5 independent experiments. *, p<0.05, p<0.01, *p<0.001 by unpaired t-test. Error bars indicate s.e.m.

FIGS. 9A-9D. PD-1 blockade does not rescue metabolic dysfunction in intratumoral T cells. (A) Representative flow cytogram of CD8+ T cells from LN and TIL preparations in B16-bearing mice receiving thrice-weekly injections of anti-PD1 or its isotype control. (B) Tabulated results from A as well as MC38-bearing mice. Each dot represents a mouse in this experiment. (C) Percentage of mice experiencing tumor regression in several experiments conducted as in B. (D) Flow cytogram and tabulated values of MitoTracker FM staining during cell division of OT-I T cells transferred into established B16$^{OVA}$ tumors under the cover of anti-PD1 or its isotype control. Data are representative of five (A,B) or three (C,D) of independent experiments. Error bars indicate s.e.m.

FIGS. 10A-10C. Regulatory T cells do not mediate mitochondrial dysfunction in tumor-infiltrating CD8+ T cells (A), Flow cytogram of CD4+ T cells from B16-bearing Foxp3$^{GFP.Cre.ERT2}$ or Foxp3$^{DTR.GFP}$ mice treated for 3 days with diphtheria toxin. (B), Representative flow cytogram and tabulated data of MitoTracker FM staining in CD8+ T cells from mice in A. (C), Flow cytogram and tabulated data of CellTrace Violet labeled CD8+ T cells stimulated with anti-CD3 and APCs in the presence or absence of flow-cytometrically purified T$_{reg}$ cells (CD4+ GFP+ cells from a Foxp3$^{GFP}$ mouse). Results are representative of (A), or represent the mean of (B, C) two of three independent experiments. Error bars indicate s.e.m.

FIGS. 12A-12G. PGC1α is repressed progressively upon entry into the tumor microenvironment. (A) qPCR analysis of Ppargc1a (encoding PGC1α) from CD8+ T cells sorted from the indicated compartments based on co-inhibitory molecule expression from day 14 B16 tumors. Results are normalized to cyclophilin B expression and scaled to LN-resident CD4+ T cells. (B) PGC1α MFI (per division) of congenically mismatched, CTV-labeled OT-I T cells transferred into B16$^{OVA}$ bearing mice for 72 h under the cover of anti-PD1 treatment or its isotype control. (C) of MitoFM staining of CD8+ T cells isolated from Ppargc1a$^{fl}$/Cd4$^{Cre}$ mice or Cd4$^{Cre}$ controls after in vitro expansion. (D) Metabolic flux measurements (Seahorse) from the cells in C. (E) Representative flow cytogram and tabulated results of PGC1α versus T-bet and (F) Ki67 staining. (G) Representative flow cytogram depicting phospho-Akt (S473) activation as a function of PD-1 status. Results are representative of three (A, C, E, F), five (B, G), or two (D) independent experiments. *p<0.05, ****p<0.0001 by unpaired (C) or paired (E,F) t test. Error bars indicate s.e.m.

FIGS. 13A-13E. Bolstering mitochondrial biogenesis improves intratumoral T cell function. (A) Metabolic analysis of OT-I T cells retrovirally transduced with an empty mCherry vector or one encoding PGC1α. MitoTracker FM staining at various timepoints post transduction is indicated. OCR, SRC, and ECAR values are from day 5-7 post transduction. (B) Representative flow cytogram of LN- and TIL-resident OT-I T cells transduced as in A and transferred into B16$^{OVA}$ bearing C57/BL6 mice. Proportion of the transferred cells in LN and TIL and tabulated MitoTracker FM staining is reported. (C) Flow cytogram depicting cytokine synthesis in OT-I T cells transferred as in b and restimulated directly ex vivo with cognate peptide. Results are tabulated to the right. (D) Tumor growth plot of B16$^{OVA}$ bearing mice treated therapeutically upon detection of palpable tumors on day 7 with 250,000 (<4 mm$^2$) or 500,000 (>4 mm$^2$) of PGC1α or control-expressing cells (E) Survival plot from e. n=15-17 mice per group. Results represent 6 (A-B), 4 (C), or 3 (D,E) independent experiments. p<0.01, *p<0.001 by unpaired t-test (A-C), two-way ANOVA with repeated measures (D), or log-rank test (E). Error bars indicate s.e.m.

SEQUENCE LISTING

Figure 1A:
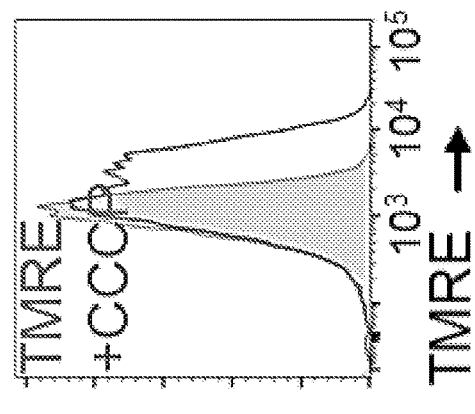
Figure 1A:
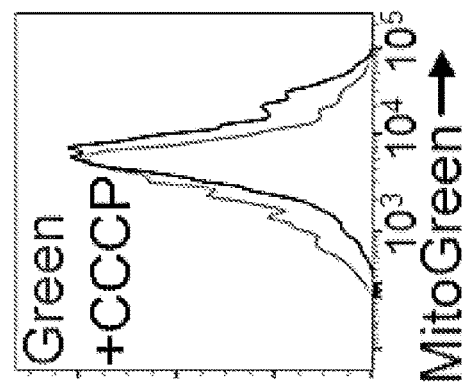
Figure 1A:
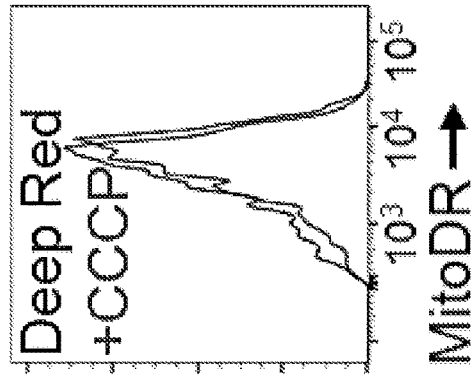
Figure 1A:
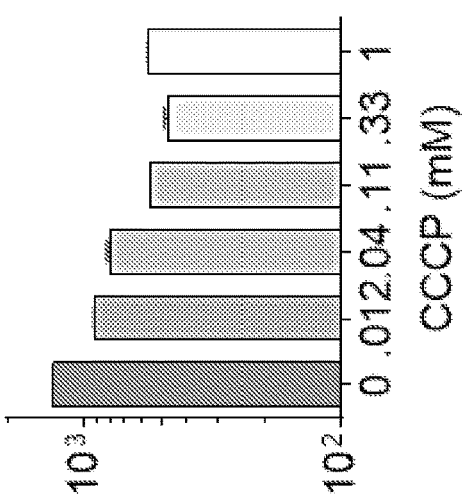
Figure 1A:
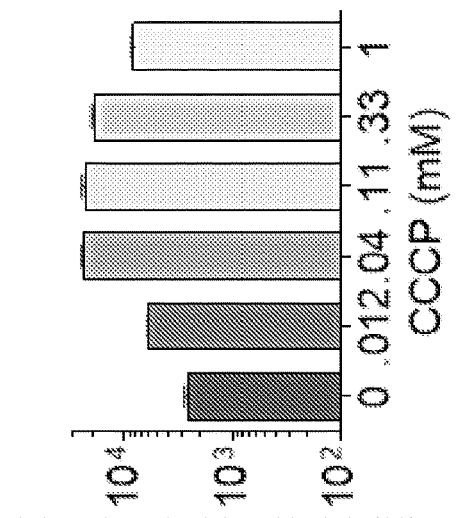
Figure 1A:
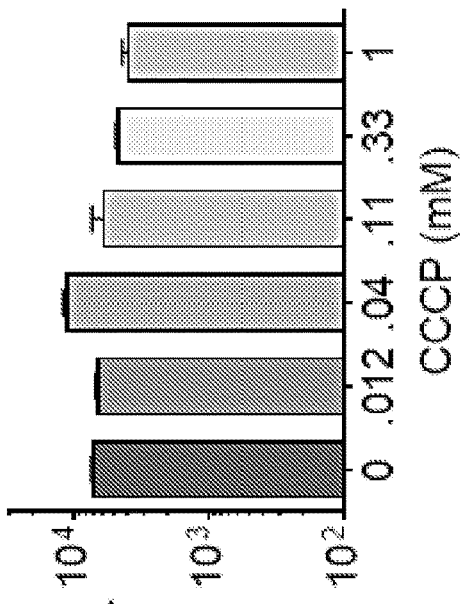

The nucleic and amino acid sequences are shown using standard letter abbreviations for nucleotide bases, and three letter code for amino acids, as defined in 37 C.F.R. 1.822. The Sequence Listing is submitted as an ASCII text file, created on Mar. 10, 2021, 68 KB, which is incorporated by reference herein. In the accompanying sequence listing:

SEQ ID NOS: 1 and 2: Exemplary human ERRα nucleic acid and protein sequence, respectively (see GenBank® Accession Nos. NM_004451.4 and NP_004442.3, respectively).

SEQ ID NOS: 3 and 4: Exemplary human GABPA nucleic acid and protein sequence, respectively (see GenBank® Accession Nos. NM_001197297.1 and NP_001184226.1, respectively).

SEQ ID NOS: 5 and 6: Exemplary human PGC1α nucleic acid and protein sequence, respectively (see GenBank® Accession Nos. NM_001330751.1 and NP_001317680.1, respectively).

SEQ ID NOS: 7 and 8: Exemplary human Tfam nucleic acid and protein sequence, respectively (see GenBank® Accession Nos. NM_001270782.1 and NP_001257711.1, respectively).

SEQ ID NO: 9: Exemplary human PGC1α isoform 2 protein sequence (see GenBank® Accession No. NP_037393.1).

DETAILED DESCRIPTION

Unless otherwise noted, technical terms are used according to conventional usage. Definitions of common terms in molecular biology can be found in Benjamin Lewin, Genes VII, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995; and other similar references.

As used herein, the singular forms "a," "an," and "the," refer to both the singular as well as plural, unless the context clearly indicates otherwise. As used herein, the term "comprises" means "includes." Thus, "comprising a nucleic acid molecule" means "including a nucleic acid molecule" without excluding other elements. It is further to be understood that any and all base sizes given for nucleic acids are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. All references, including patent applications and patents, and sequences associated with the GenBank® Accession Numbers listed (as of Jun. 24, 2016) are herein incorporated by reference.

In order to facilitate review of the various embodiments of the disclosure, the following explanations of specific terms are provided:

Administration: To provide or give a subject an agent, such as a disclosed recombinant T cell or other therapeutic agent, by any effective route. Exemplary routes of administration include, but are not limited to, injection (such as subcutaneous, intramuscular, intradermal, intraperitoneal, intratumoral, and intravenous), transdermal, intranasal, and inhalation routes.

Cancer: A malignant tumor characterized by abnormal or uncontrolled cell growth. Other features often associated with cancer include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc. "Metastatic disease" refers to cancer cells that have left the original tumor site and migrate to other parts of the body for example via the bloodstream or lymph system.

Chimeric antigen receptor (CAR): Artificial, engineered T cell receptors, which graft an arbitrary specificity onto an immune effector cell. Typically, these receptors are used to graft the specificity of a monoclonal antibody onto a T cell; with transfer of their coding sequence facilitated by vectors. Using adoptive cell transfer, CARs can be useful to treating cancer. For example, T cells (obtained from the patient or from a donor) are modified so that they express receptors specific to the patient's particular cancer. The modified T cells, which can then recognize and kill the cancer cells, are introduced into the patient. First generation CARs typically included the intracellular domain from the CD3 ζ-chain, which is the primary transmitter of signals from endogenous TCRs. Second generation CARs added intracellular signaling domains from various costimulatory protein receptors (e.g., CD28, 41BB, ICOS) to the cytoplasmic tail of the CAR to provide additional signals to the T cell. Third generation CARs combine multiple signaling domains, such as CD3z-CD28-41BB or CD3z-CD28-OX40, to augment potency. Any of these CARs can be used herein.

Contact: Placement in direct physical association, including a solid or a liquid form. Contacting can occur in vitro or ex vivo, for example, by adding a reagent to a sample (such as one containing recombinant T cells), or in vivo by administering to a subject.

Effective amount: The amount of an agent (such as recombinant T cells disclosed herein) that is sufficient to effect beneficial or desired results.

A effective amount (also referred to as a therapeutically effective amount) may vary depending upon one or more of: the subject and disease condition being treated, the weight and age of the subject, the severity of the disease condition, the manner of administration and the like, which can readily be determined by one of ordinary skill in the art. The beneficial therapeutic effect can include enablement of diagnostic determinations; amelioration of a disease, symptom, disorder, or pathological condition; reducing or preventing the onset of a disease, symptom, disorder or condition; and generally counteracting a disease, symptom, disorder or pathological condition. In one embodiment, an "effective amount" (e.g., of recombinant T cells disclosed herein) is an amount sufficient to reduce the volume/size of a tumor, the weight of a tumor, the number of metastases, reduce the volume/size of a metastasis, the weight of a metastasis, or combinations thereof, for example by at least 10%, at least 20%, at least 25%, at least 50%, at least 70%, at least 75%, at least 80%, at least 90%, at least 95%, or at least 99% (as compared to no administration of the therapeutic agent). In one embodiment, an "effective amount" (e.g., of a vector encoding a target gene(s), such as TCR, CAR, PGC1α, Tfam, GABPA, and/or ERRα) is an amount sufficient to increase the activity and/or expression of the target gene(s) in an exhausted tumor-infiltrating T cell, for example by at least 10%, at least 20%, at least 25%, at least 50%, at least 70%, at least 75%, at least 80%, at least 90%, at least 95%, at least 99%, at least 100%, at least 200%, at least 300%, at least 400%, at least 500%, or at least 600% (as compared to no administration of the therapeutic agent).

Estrogen-related receptor alpha (ERRα): (e.g., OMIM 601998): Also known as NR3B1, is an orphan nuclear receptor involved in the activation of mitochondrial genes and mitochondrial biogenesis. ERRα sequences are publically available, for example from the GenBank® sequence database (e.g., Accession Nos. NP_004442.3, P11474.3, AAH63795.2, JAA39845.1, AAB51250.1, AAQ17212.1, and AAS20260.1 provide exemplary ERRα protein sequences, while Accession Nos. NM_004451.4, NM_001282450.1, NM_001282451.1, NM_007953.2 and NM_001008511.2 provide exemplary ERRα nucleic acid sequences). One of ordinary skill in the art can identify additional ERRα nucleic acid and protein sequences, including ERRα variants, such as those having at least 80%, at least 85%, at least 90%, at least 92%, at least 95%, at least 98%, or at least 99% sequence identity to these GenBank® sequences. In some examples, a variant ERRα is one that is resistant to negative regulation. Examples of a mutation that can be made to ERRα to increase its resistance to negative regulation includes but is not limited to S19A.

Increase or Decrease: A statistically significant positive or negative change, respectively, in quantity from a control value (such as a value representing no therapeutic agent). An increase is a positive change, such as an increase at least 50%, at least 100%, at least 200%, at least 300%, at least 400% or at least 500% as compared to the control value. A decrease is a negative change, such as a decrease of at least 20%, at least 25%, at least 50%, at least 75%, at least 80%, at least 90%, at least 95%, at least 98%, at least 99%, or at least 100% decrease as compared to a control value. In some examples the decrease is less than 100%, such as a decrease of no more than 90%, no more than 95%, or no more than 99%.

Isolated: An "isolated" biological component (such as T cells, a nucleic acid molecule, or a protein) has been substantially separated, produced apart from, or purified away from other biological components in the cell or tissue of an organism in which the component occurs, such as other cells (e.g., RBCs), chromosomal and extrachromosomal DNA and RNA, and proteins. Nucleic acids and proteins that have been "isolated" include nucleic acids and proteins purified by standard purification methods. The term also embraces nucleic acids and proteins prepared by recombinant expression in a host cell as well as chemically synthesized nucleic acids and proteins. Isolated T cells, or isolated recombinant T cells, in some examples are at least 50% pure, such as at least 75%, at least 80%, at least 90%, at least 95%, at least 98%, or at least 100% pure.

Mitochondrial transcription factor A (Tfam or mtTFA): (e.g., OMIM 600438): A mitochondrial transcription factor involved in the activation of mitochondrial transcription and participates in mitochondrial genome replication. Tfam binds mitochondrial promoter DNA to aid transcription of the mitochondrial genome. Tfam sequences are publically available, for example from the GenBank® sequence database (e.g., Accession Nos. NP_003192.1, NP_001257711.1, NP_033386.1, AAH62022.1, NP_001123683.1, and NP_001029188.2 provide exemplary Tfam protein sequences, while Accession Nos. CR407653.1, NM_003201.2, NM_001270782.1, NM_009360.4 and NM_031326.1 provide exemplary Tfam nucleic acid sequences). One of ordinary skill in the art can identify additional Tfam nucleic acid and protein sequences, including Tfam variants, such as those having at least 80%, at least 85%, at least 90%, at least 92%, at least 95%, at least 98%, or at least 99% sequence identity to these GenBank® sequences. In some examples, a variant Tfam is one that is resistant to negative regulation. Examples of mutations that can be made to Tfam to increase its resistance to negative regulation include but are not limited to 55A, S56A, and S61A GA binding protein transcription factor, alpha subunit (GABPA) (aka E4TF1-10, Nft2, Nrf2, Rch04A07): (e.g., OMIM 600609): One of three GA-binding protein transcription factor subunits which functions as a DNA-binding subunit, likely involved in activation of cytochrome oxidase expression and nuclear control of mitochondrial function. GABPA sequences are publically available, for example from the GenBank® sequence database (e.g., Accession Nos. NP_001184226.1, NM_008065.2, NP_001102311.1, and NP_001253514.1 provide exemplary GABPA protein sequences, while Accession Nos. NM_001197297.1, NP_032091.2, NM_001108841.1, and NM_001266585.1 provide exemplary GABPA nucleic acid sequences). One of ordinary skill in the art can identify additional GABPA nucleic acid and protein sequences, including GABPA variants, such as those having at least 80%, at least 85%, at least 90%, at least 92%, at least 95%, at least 98%, or at least 99% sequence identity to these GenBank® sequences. In some examples, a variant GABPA is one that is resistant to negative regulation. An examples of a mutation that can be made to GABPA to increase its resistance to negative regulation includes but is not limited to T280E.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence (such as a TCR, CAR, PGC1α, Tfam, GABPA, or ERRα coding sequence). Generally, operably linked DNA sequences are contiguous and, where necessary to join two protein coding regions, in the same reading frame.

Programmed cell death protein 1 (PD-1 or CD279) (e.g., OMIM 600244): A cell surface receptor that belongs to the immunoglobulin superfamily and is expressed on T cells and pro-B cells. PD-1 binds two ligands, PD-L1 and PD-L2. The human form is a 268 aa type 1 transmembrane protein. PD-1 is an inhibitory receptor that mediates T-cell exhaustion. PD-1 sequences are publically available, for example from the GenBank® sequence database (e.g., Accession Nos. NP_005009.2 (mature peptide is aa 21-288), CAA48113.1, NP_001301026.1 (mature peptide is aa 25-288), and CAA48113.1 (mature peptide is aa 21-288) provide exemplary PD-1 protein sequences, while Accession Nos. L27440.1, NM_005018.2, X67914.1, AB898677.1 and EU295528.2 provide exemplary PD-1 nucleic acid sequences). One of ordinary skill in the art can identify additional PD-1 nucleic acid and protein sequences, including PD-1 variants, such as those having at least 80%, at least 85%, at least 90%, at least 92%, at least 95%, at least 98%, or at least 99% sequence identity to these GenBank® sequences.

Peroxisome proliferator-activated receptor (PPAR) gamma coactivator 1-alpha (PGC1α or PPARGC1α): (e.g., OMIM 604517): A transcriptional coactivator that regulates the genes involved in energy metabolism. PGC-1α is a regulator of mitochondrial biogenesis and function. PGC-1α sequences are publically available, for example from the GenBank® sequence database (e.g., Accession Nos. NP_001317680.1, NP_037393.1, NP_032930.1, and NP_112637.1 provide exemplary PGC-1α protein sequences, while Accession Nos. NM_001330751.1, NM_013261.3, NM_008904.2, and NM_031347.1 provide exemplary PGC-1α nucleic acid sequences). One of ordinary skill in the art can identify additional PGC-1α nucleic acid and protein sequences, including PGC-1α variants, such as those having at least 80%, at least 85%, at least 90%, at least 92%, at least 95%, at least 98%, or at least 99% sequence identity to these GenBank® sequences. In some examples, a variant PGC-1α is one that is resistant to negative regulation. An examples of a mutation that can be made to PGC-1α to increase its resistance to negative regulation includes but is not limited to S572A.

Pharmaceutically acceptable carriers: The pharmaceutically acceptable carriers useful in this invention are conventional. Remington's Pharmaceutical Sciences, by E. W. Martin, Mack Publishing Co., Easton, Pa., 15th Edition (1975), describes compositions and formulations suitable for pharmaceutical delivery of a therapeutic agent, such as a vector or recombinant T cell disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Promoter: An array of nucleic acid control sequences which direct transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription.

Examples of promoters include, but are not limited to the SV40 promoter, the CMV enhancer-promoter, and the CMV enhancer/β-actin promoter. Both constitutive and inducible promoters are included (see e.g., Bitter et al., *Methods in Enzymology* 153:516-544, 1987). Also included are those promoter elements which are sufficient to render promoter-dependent gene expression controllable for cell-type specific, tissue-specific, or inducible by external signals or agents; such elements may be located in the 5' or 3' regions of the gene. Promoters produced by recombinant DNA or synthetic techniques can also be used to provide for transcription of the nucleic acid sequences.

Recombinant: A recombinant nucleic acid molecule is one that has a sequence that is not naturally occurring (e.g., a mutated PGC1α, Tfam, GABPA, or ERRα) or has a sequence that is made by an artificial combination of two otherwise separated segments of sequence. This artificial combination can be accomplished by routine methods, such as chemical synthesis or by the artificial manipulation of isolated segments of nucleic acids, such as by genetic engineering techniques. Similarly, a recombinant protein is one encoded for by a recombinant nucleic acid molecule. Similarly, a recombinant or transgenic cell is one that contains a recombinant nucleic acid molecule and expresses a recombinant protein.

Sequence identity of amino acid sequences: The similarity between amino acid (or nucleotide) sequences is expressed in terms of the similarity between the sequences, otherwise referred to as sequence identity. Sequence identity is frequently measured in terms of percentage identity (or similarity or homology); the higher the percentage, the more similar the two sequences are. Homologs of a polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Variants of a native PGC1α, Tfam, GABPA, or ERRα protein or coding sequences (such as a protein (or coding sequence thereof) with increased resistance to negative regulation) are typically characterized by possession of at least about 80%, at least 90%, at least 95%, at least 96%, at least 97%, at least 98% or at least 99% sequence identity counted over the full length alignment with the amino acid sequence using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or at least 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Thus, a variant PGC1α, Tfam, GABPA, or ERRα protein or nucleic acid sequence can have at least 80%, at least 85%, at least 90%, at least 91%, at least 92%, at least 93%, at least 94%, at least 95%, at least 96%, at least 97%, at least 98% or at least 99% sequence identity to any of the sequences shown in the GenBank® Accession Nos. provided herein.

Subject: A vertebrate, such as a mammal, for example a human. Mammals include, but are not limited to, murines, simians, humans, farm animals, sport animals, and pets. In one embodiment, the subject is a non-human mammalian subject, such as a monkey or other non-human primate, mouse, rat, rabbit, pig, goat, sheep, dog, cat, horse, or cow. In some examples, the subject has a tumor, such as a cancer, that can be treated using the recombinant T cells disclosed herein. In some examples, the subject is a laboratory animal/organism, such as a mouse, rabbit, or rat.

T cells: White blood cells containing a T cell receptor on their cell surface, which play a role in cell-mediated immunity. In some examples, a T cell is obtained from the peripheral blood of a mammalian subject (such as one having cancer), for example via leukapheresis.

T cell receptor (TCR): A receptor found on the surface of T lymphocytes (or T cells) responsible for recognizing fragments of antigen as peptides bound to major histocompatibility complex (MHC) molecules. The TCR is composed of two different protein chains/ In humans, in 95% of T cells the TCR consists of an alpha (α) and beta (β) chain, whereas in 5% of T cells the TCR consists of gamma and delta (γ/δ) chains. This ratio changes during ontogeny and in diseased states as well as in different species. When the TCR engages with antigenic peptide and MHC (peptide/MHC), the T lymphocyte is activated through signal transduction, that is, a series of biochemical events mediated by associated enzymes, co-receptors, specialized adaptor molecules, and activated or released transcription factors. In one example, a TCR is a recombinant TCR, such as one used in TCR-engineered T cells.

Therapeutic agent: Refers to one or more molecules or compounds that confer some beneficial effect upon administration to a subject. The beneficial therapeutic effect can include enablement of diagnostic determinations; amelioration of a disease, symptom, disorder, or pathological condition; reducing or preventing the onset of a disease, symptom, disorder or condition; and generally counteracting a disease, symptom, disorder or pathological condition.

Transduced and Transformed: A virus or vector "transduces" a cell when it transfers nucleic acid into the cell. A cell is "transformed" or "transfected" by a nucleic acid transduced into the cell when the nucleic acid molecule becomes stably replicated by the cell, either by incorporation of the nucleic acid into the cellular genome, or by episomal replication.

Numerous methods of transfection are known to those skilled in the art, such as: chemical methods (e.g., calcium-phosphate transfection), physical methods (e.g., electroporation, microinjection, particle bombardment), fusion (e.g., liposomes), receptor-mediated endocytosis (e.g., DNA-protein complexes, viral envelope/capsid-DNA complexes) and by biological infection by viruses such as recombinant viruses {Wolff, J. A., ed, Gene Therapeutics, Birkhauser, Boston, USA (1994)}. In the case of infection by retroviruses, the infecting retrovirus particles are absorbed by the target cells, resulting in reverse transcription of the retroviral RNA genome and integration of the resulting provirus into the cellular DNA.

Transgene: An exogenous gene supplied by a vector. In one example, a transgene includes one or more PGC1α, Tfam, GABPA, or ERRα coding sequences, for example in combination with a CAR or TCR coding sequence.

Treating, Treatment, and Therapy: Any success or indicia of success in the attenuation or amelioration of an injury, pathology or condition, including any objective or subjective parameter such as abatement, remission, diminishing of symptoms or making the condition more tolerable to the patient, slowing in the rate of degeneration or decline, making the final point of degeneration less debilitating, improving a subject's physical or mental well-being, or prolonging the length of survival. The treatment may be assessed by objective or subjective parameters; including the results of a physical examination, blood and other clinical tests, and the like. In some examples, treatment with the disclosed methods results in a decrease in the number, volume, and/or weight of a tumor and/or metastases.

Tumor, neoplasia, malignancy or cancer: A neoplasm is an abnormal growth of tissue or cells which results from excessive cell division. Neoplastic growth can produce a tumor. The amount of a tumor in an individual is the "tumor burden" which can be measured as the number, volume, or weight of the tumor. A "non-cancerous tissue" is a tissue from the same organ wherein the malignant neoplasm formed, but does not have the characteristic pathology of the neoplasm. Generally, noncancerous tissue appears histologically normal. A "normal tissue" is tissue from an organ, wherein the organ is not affected by cancer or another disease or disorder of that organ. A "cancer-free" subject has not been diagnosed with a cancer of that organ and does not have detectable cancer.

Exemplary tumors, such as cancers, that can be treated using the disclosed recombinant T cells include solid tumors, such as breast carcinomas (e.g. lobular and duct carcinomas, such as a triple negative breast cancer), sarcomas, carcinomas of the lung (e.g., non-small cell carcinoma, large cell carcinoma, squamous carcinoma, and adenocarcinoma), mesothelioma of the lung, colorectal adenocarcinoma, stomach carcinoma, prostatic adenocarcinoma, ovarian carcinoma (such as serous cystadenocarcinoma and mucinous cystadenocarcinoma), ovarian germ cell tumors, testicular carcinomas and germ cell tumors, pancreatic adenocarcinoma, biliary adenocarcinoma, hepatocellular carcinoma, bladder carcinoma (including, for instance, transitional cell carcinoma, adenocarcinoma, and squamous carcinoma), renal cell adenocarcinoma, endometrial carcinomas (including, e.g., adenocarcinomas and mixed Mullerian tumors (carcinosarcomas)), carcinomas of the endocervix, ectocervix, and vagina (such as adenocarcinoma and squamous carcinoma of each of same), tumors of the skin (e.g., squamous cell carcinoma, basal cell carcinoma, malignant melanoma, skin appendage tumors, Kaposi sarcoma, cutaneous lymphoma, skin adnexal tumors and various types of sarcomas and Merkel cell carcinoma), esophageal carcinoma, carcinomas of the nasopharynx and oropharynx (including squamous carcinoma and adenocarcinomas of same), salivary gland carcinomas, brain and central nervous system tumors (including, for example, tumors of glial, neuronal, and meningeal origin), tumors of peripheral nerve, soft tissue sarcomas and sarcomas of bone and cartilage, head and neck squamous cell carcinoma, and lymphatic tumors (including B-cell and T-cell malignant lymphoma). In one example, the tumor is an adenocarcinoma.

The disclosed recombinant T cells can also be used to treat liquid tumors, such as a lymphatic, white blood cell, or other type of leukemia. In a specific example, the tumor treated is a tumor of the blood, such as a leukemia (for example acute lymphoblastic leukemia (ALL), chronic lymphocytic leukemia (CLL), acute myelogenous leukemia (AML), chronic myelogenous leukemia (CML), hairy cell leukemia (HCL), T-cell prolymphocytic leukemia (T-PLL), large granular lymphocytic leukemia, and adult T-cell leukemia), a lymphoma (such as Hodgkin's lymphoma or non-Hodgkin's lymphoma), or a myeloma.

Under conditions sufficient for: A phrase that is used to describe any environment that permits a desired activity. In one example the desired activity is increased expression or activity of one or more PGC1α, Tfam, GABPA, and ERRα, for example in a T cell. In one example the desired activity is treatment of a tumor in vivo, for example using the disclosed recombinant T cells.

Vector: A nucleic acid molecule as introduced into a host cell (such as a T cell), thereby producing a transformed host cell. A vector may include nucleic acid sequences that permit it to replicate in the host cell, such as an origin of replication. A vector may also include one or more PGC1α, Tfam, GABPA, or ERRα coding sequences, for example in combination with a CAR or TCR coding sequence, and/or selectable marker genes and other genetic elements known in the art. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, protein coating or the like.

Overview

While tumor-specific T cells recognize cancer cells, they are often rendered dysfunctional due to an immunosuppressive microenvironment. As T cell activation is bioenergetically demanding, we hypothesized that T cell dysfunction in cancer is due in part to metabolic insufficiency caused by the dearth nutrient conditions of the tumor microenvironment. It is shown herein that T cells demonstrate a crippling loss of mitochondrial function and mass when infiltrating murine and human tumors. Persistent loss of mitochondrial function occurs specifically in the tumor microenvironment, and is not merely a product of robust activation. Tumor infiltrating T cells (TILs) show a progressive loss of PGC1α, a transcriptional coactivator programming mitochondrial biogenesis, induced in part by chronic Akt signaling in tumor-specific CD8+ T cells. Reprogramming tumor-specific T cells through enforced expression of PGC1α results in superior intratumoral metabolic and effector function. The data herein support a model in which signals present in the tumor microenvironment repress T cell oxidative metabolism, resulting in effector cells with metabolic needs that cannot be met. As such, the metabolic status of the tumor microenvironment may predict the response to immunotherapy. The results indicate that modulation or reprogramming of the altered metabolism of tumor-infiltrating T cells represents a potential strategy to reinvigorate dysfunctional T cells for the treatment of cancer.

The data herein place the persistence and function of mitochondria as central to sustained effector function of T cells, especially those under continual stimulation like in cancer or chronic viral infections. Observed most prominently in CD8+ T cells specifically in the tumor microenvironment, we demonstrate a progressive and persistent loss of mitochondrial function and mass. Importantly, at least in the timecourse of rapidly growing tumor, this effect could be observed concomitantly with PD-1 upregulation but largely independently of treatment with anti-PD-1, with only mild and temporary increases observed in response to of this particular checkpoint. Rather, Akt signaling associated with chronic activation results in repression of oxidative metabolism, thus driving an unsustainable metabolic program. Thus, the data herein bring to light the metabolic nature of T cell dysfunction, in cancer and in general.

While glucose metabolism, especially aerobic glycolysis, has been heavily studied as a key mediator of T cell effector fate and function, the results herein indicate that mitochondrial function and mass are dynamically regulated and required to maintain optimal effector function. This is consistent with data suggesting mitochondrial membrane potential may predict stemness in tumor-infiltrating T cells, and that cytokine production may be increased in T cells that display high mitochondrial activity (Sukumar et al., 2016).

There is some debate as to whether MitoTracker Deep Red FM is a potentiometric dye or one that stains for mitochondrial mass irrespective of membrane potential (Xiao et al., 2016). The data herein employing uncoupling agents such as CCCP indicate while Deep Red FM may show some sensitivity for membrane potential at high doses, this pales in comparison to results achieved with TMRE, a true potentiometric dye (FIG. 1A). The corollary data herein employing MitoTracker Green and VDAC antibodies indeed confirm that T cells infiltrating tumors exhibit losses of mitochondrial function and total mass, consistent with repressed PGC1-mediated mitochondrial biogenesis. While effector T cells have been shown to possess fewer mitochondria than their memory counterparts (van der Windt et al., 2012; van der Windt et al., 2013), it is unclear how chronic stimulation might alter this fate. The data herein suggest that the continued, inflammatory activation of T cells in cancer promotes a persistent defect in mitochondrial biogenesis, mediated in part by Akt-controlled inhibition of Foxo-programmed PGC1α transcription. While Akt does repress oxidative metabolism, more traditional roles for Akt suggest its potential as an in vivo therapeutic target may be limited, as T cells may require Akt and downstream signaling in situ to mediate effector functions (Macintyre et al., 2011). However, recent studies have revealed that this may not be the case. Akt inhibition has been employed in preclinical and translational settings as a means to reinvigorate TIL expansion, in part through modulating oxidative metabolism (Crompton et al., 2015). In addition, T cells lacking the mammalian target of rapamycin complex 2, the kinase for the hydrophobic motif (S473) of Akt, show superior effector function and increased oxidative metabolism, suggesting that full Akt activation may not be acutely required for effector function (Pollizzi et al., 2015). Thus, the data herein identify PGC1α as a crucial mechanistic link between Akt and repressed oxidative metabolism in tumor-infiltrating T cells. In addition, Akt inhibitors, which are currently being evaluated in clinical trials as anti-cancer agents, may have immunomodulatory effects that could be synergistic with immunotherapies.

PD-1 inhibits mTORC1 signaling (which has metabolic consequences), and modulates metabolism at the genetic level (Wherry and Kurachi, 2015). However, we only observed association between PD-1 upregulation and mitochondrial insufficiency, with mild and short-lived effects on mitochondrial metabolism arising from anti-PD-1 treatment. In the tumor microenvironment, there may be too many other signals to be offset by PD-1 blockade alone, or that other co-inhibitory molecules like LAG-3 or TIGI T may play additional roles in inhibiting oxidative metabolism in the tumor microenvironment. Likewise, we fail to see any effect of regulatory T cell suppression on mitochondrial function and mass, both using a genetic model of regulatory T cell depletion, Foxp3$^{DTR.GFP}$ mice treated with diphtheria toxin in established tumors, as well as coculture of purified $T_{reg}$ cells with activated CD8+ T cells.

The data herein point to PGC1α as a key node of signal integration tying a diverse array of cellular signals (including Akt signaling) to mitochondrial biogenesis. Type I/II interferons, TNF, IL-12, energy charge, and low NAD+/NADH or oleate/palmitate ratios have been shown to repress PGC1α expression, localization or transcriptional activity through a variety of signaling pathways (Alvarez-Guardia et al., 2010; Haghikia et al., 2015; Kauppinen et al., 2013; Kim et al., 2007b; Palomer et al., 2009; Scarpulla, 2011). Indeed, PGC1α is post-translationally modified by a number of signaling pathways important for T cell biology (Akt, p38-MAPK, AMPK, SIRT1, PRMT1) (Fernandez-Marcos and Auwerx, 2011). Thus, the balance of these signals in the inflammatory milieu may determine PGC1α activity and its ability to program mitochondrial biogenesis. Furthermore, these results indicate that determining the metabolic status of tumor-infiltrating T cells as well as the presence of various PGC1α repressors may predict responses to immunotherapeutic regimens like checkpoint blockade.

The results herein add to a growing number of reports that collectively suggest that the T cell dysfunction observed in chronic activation (T cell exhaustion) has underpinnings in basic cellular processes like metabolism. Unlike anergy (induced by minimal signaling, TCR ligation alone, in a non-inflammatory environment), persistent, inflammatory activation in cancer and chronic viral infections promote an effector state that T cells cannot sustain (Jiang et al., 2015; Schietinger and Greenberg, 2014; Wherry and Kurachi, 2015). This is especially perilous in the tumor microenvironment, as chronic inflammatory signals might drive a sustained reliance on glycolysis in a tissue site where glucose levels are extremely low (Siska and Rathmell, 2015). It was observed that T cells also show depressed glucose uptake compared to LN-resident cells (FIGS. 2A-2E) and glycolysis compared to matched, virus-activated cells (FIG. 3B), suggesting that, generally, T cell 'exhaustion' is characterized by metabolic insufficiency (Chang et al., 2015; Ho et al., 2015; Zhao et al., 2015). Teleologically, T cells in 'metabolic distress' might upregulate co-inhibitory molecules as a means to prevent terminal loss of metabolic sufficiency or survival, a model consistent with results obtained in chronic viral infection (Staron et al., 2014). These crippling metabolic defects can be persistent even when removed from that microenvironment (FIG. 3D) which may provide a potential explanation for situations in which concomitant tumor immunity is lost at distal sites.

Finally, the data herein support modulation and reprogramming of the metabolic state as a viable strategy for the improvement of immunotherapy for cancer. While advances in checkpoint blockade and other types of immunotherapy have revealed that the mechanisms blocking immune cell activation can be altered by therapeutic intervention, tumors present a harsh microenvironment that is immunosuppressive by its basic nature. Further, the data suggest that the metabolic status of individual tumor microenvironments, which can vary from model to model or patient to patient, may help predict the response to immunotherapies like checkpoint blockade. While these results demonstrate that the direct metabolic reprogramming of T cells can have efficacy, other strategies to remodel the metabolism of the microenvironment itself can be used to create a more permissive environment for T cell activity.

Metabolism is central to cellular function, so it is largely unsurprising that T cells fail in nutrient-poor conditions. These result have shed light on the fact that during chronic activation as in cancer, T cells are driven to proliferate and perform effector function at the expense of their continued persistence and longevity. Development of strategies to modify the bioenergetics of T cells or the tumor microenvironment itself has the promise to improve and synergize with other forms of immunotherapy to increase the efficacy of the treatment of cancer.

Recombinant T Cells

Provided herein are recombinant T cells that can be used to improve cellular immunotherapy, such as chimeric antigen receptor (CAR) T cell therapy or T cell receptor (TCR)-engineered T cells. For example, the disclosure provides recombinant T cells containing a vector that encodes one or more of peroxisome proliferator-activated receptor (PPAR) gamma coactivator 1-alpha (PGC1α), mitochondrial transcription factor A (Tfam), GA binding protein transcription factor alpha subunit (GABPA), and estrogen-related receptor alpha (ERRα). Expression of the vector in the T cell results in increased expression of one or more of these genes, and thus increased activity of these proteins. In some examples, the PGC1α, Tfam, GABPA, and/or ERRα expressed from the vector is a variant sequence that encodes a protein that is resistant to negative regulation.

The recombinant T cell expressing PGC1α, Tfam, GABPA, and/or ERRα may also include a chimeric antigen receptor (CAR), or a recombinant T cell receptor (TCR) (such as a TCR that targets the T cells to a tumor cells, such as WT1 for acute myeloid leukemia and chronic myeloid leukemia). The CAR or recombinant TCR can be expressed from the same or a different vector than the PGC1α, Tfam, GABPA, and/or ERRα.

Thus, in some examples, expression of PGC1α in the T cell increases PGC1α protein expression and/or activity in the recombinant T cells by at least 20%, at least 30%, at least 40%, at least 50%, at least 60%, at least 70%, at least 75%, at least 80%, at least 90%, at least 95%, at least 100%, at least 200%, at least 300%, at least 400%, at least 500% or at least 600%. In some examples, expression of Tfam in the T cell increases Tfam protein expression and/or activity in the recombinant T cells by at least 20%, at least 30%, at least 40%, at least 50%, at least 60%, at least 70%, at least 75%, at least 80%, at least 90%, at least 95%, at least 100%, at least 200%, at least 300%, at least 400%, at least 500% or at least 600%. In some examples, expression of GABPA in the T cell increases GABPA protein expression and/or activity in the recombinant T cells by at least 20%, at least 30%, at least 40%, at least 50%, at least 60%, at least 70%, at least 75%, at least 80%, at least 90%, at least 95%, at least 100%, at least 200%, at least 300%, at least 400%, at least 500% or at least 600%. In some examples, expression of ERRα in the T cell increases ERRα protein expression and/or activity in the recombinant T cells by at least 20%, at least 30%, at least 40%, at least 50%, at least 60%, at least 70%, at least 75%, at least 80%, at least 90%, at least 95%, at least 100%, at least 200%, at least 300%, at least 400%, at least 500% or at least 600%.

In some examples, expressing PGC1α, Tfam, GABPA, and/or ERRα in the recombinant T cells increases mitochondrial activity (e.g., oxidative metabolism) in the recombinant T cells by at least 20%, at least 30%, at least 40%, at least 50%, at least 60%, at least 70%, at least 75%, at least 80%, at least 90%, at least 95%, at least 100%, at least 200%, at least 300%, at least 400%, at least 500% or at least 600%. In some examples, expressing PGC1α, Tfam, GABPA, and/or ERRα in the recombinant T cells increases mitochondrial mass in the recombinant T cells by at least 20%, at least 30%, at least 40%, at least 50%, at least 60%, at least 70%, at least 75%, at least 80%, at least 90%, at least 95%, at least 100%, at least 200%, at least 300%, at least 400%, at least 500% or at least 600%. In some examples, combinations of these effects are achieved.

The vectors used to generate such recombinant T cells, such as a vector that includes a nucleic acid molecule encoding one or more of PGC1α, Tfam, GABPA, and ERRα and a nucleic acid molecule encoding a CAR a recombinant TCR, are provided herein. Examples of vectors that can be used include viral vectors, such as a lentiviral vector or retrovirus.

1. PGC1α, Tfam, GABPA, and ERRα

The PGC1α, Tfam, GABPA, or ERRα coding sequence in the vector can be native or variant PGC1α, Tfam, GABPA, or ERRα sequence. Native PGC1α, Tfam, GABPA, and ERRα sequences are provided above via GenBank® Accession Nos. for several species. Thus, in some examples, the vector introduced into the T cell includes a native PGC1α, Tfam, GABPA, and/or ERRα coding sequence. In some examples, the vector introduced into the T cell includes a non-native PGC1α, Tfam, GABPA, and/or ERRα coding sequence, but encodes a native PGC1α, Tfam, GABPA, and/or ERRα protein sequence (e.g., a coding sequence that is degenerate).

Variant PGC1α, Tfam, GABPA, or ERRα proteins, including variants of the protein sequences provided above via GenBank® Accession Nos., can contain one or more mutations, such as a single insertion, a single deletion, a single substitution. In some examples, the variant PGC1α, Tfam, GABPA, or ERRα protein includes 1-20 insertions, 1-20 deletions, 1-20 substitutions, and/or any combination thereof (e.g., single insertion together with 1-19 substitutions). In some examples, the disclosure provides a variant of any native PGC1α, Tfam, GABPA, or ERRα protein having 1, 2, 3, 4, 5, 6, 7, 8, 9, 10, 11, 12, 13, 14, 15, 16, 17, 18, 19 or 20 additional amino acid changes. In some examples, a variant PGC1α, Tfam, GABPA, or ERRα protein includes 1-8 insertions, 1-15 deletions, 1-10 substitutions, and/or any combination thereof (e.g., 1-15, 1-4, or 1-5 amino acid deletions together with 1-10, 1-5 or 1-7 amino acid substitutions). In some examples, the disclosure provides a variant PGC1α, Tfam, GABPA, or ERRα protein having 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acid changes. In one example, such variant peptides are produced by manipulating the nucleotide sequence encoding a peptide using standard procedures such as site-directed mutagenesis or PCR. Such variants can also be chemically synthesized.

One type of modification includes the substitution of amino acids for amino acid residues having a similar biochemical property, that is, a conservative substitution (such as 1-4, 1-8, 1-10, or 1-20 conservative substitutions). Typically, conservative substitutions have little to no impact on the activity of a resulting peptide. For example, a conservative substitution is an amino acid substitution in any native PGC1α, Tfam, GABPA, or ERRα protein sequence, which does not substantially affect the native function of the protein. An alanine scan can be used to identify which amino acid residues in a PGC1α, Tfam, GABPA, or ERRα protein can tolerate an amino acid substitution. In one example, the native function of PGC1α, Tfam, GABPA, or ERRα is not altered by more than 25%, for example not more than 20%, for example not more than 10%, when an alanine, or other conservative amino acid, is substituted for 1-4, 1-8, 1-10, or 1-20 native amino acids. Examples of amino acids which may be substituted for an original amino acid in a protein and which are regarded as conservative substitutions include: Ser for Ala; Lys, Gln, or Asn for Arg; Gln or His for Asn; Glu for Asp; Ser for Cys; Asn for Gln; Asp for Glu; Pro for Gly; Asn or Gln for His; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and Ile or Leu for Val.

More substantial changes can be made by using substitutions that are less conservative, e.g., selecting residues that differ more significantly in their effect on maintaining: (a) the structure of the polypeptide backbone in the area of the substitution, for example, as a sheet or helical conformation; (b) the charge or hydrophobicity of the polypeptide at the target site; or (c) the bulk of the side chain. The substitutions that in general are expected to produce the greatest changes in polypeptide function are those in which: (a) a hydrophilic residue, e.g., serine or threonine, is substituted for (or by) a hydrophobic residue, e.g., leucine, isoleucine, phenylalanine, valine or alanine; (b) a cysteine or proline is substituted for (or by) any other residue; (c) a residue having an electropositive side chain, e.g., lysine, arginine, or histidine, is substituted for (or by) an electronegative residue, e.g., glutamic acid or aspartic acid; or (d) a residue having a bulky side chain, e.g., phenylalanine, is substituted for (or by) one not having a side chain, e.g., glycine. The effects of these amino acid substitutions (or other deletions and/or additions) can be assessed by analyzing the function of the mutant variant PGC1α, Tfam, GABPA, or ERRα protein by analyzing the native function of the protein.

In one example, the PGC1α, Tfam, GABPA, and/or ERRα expressed from the vector is a variant form that is resistant to negative regulation. In one example, the variant PGC1α, Tfam, GABPA, or ERRα has an increased ability to be resistant to negative regulation, such as an increase of at least 10%, at least 20%, at least 30%, at least 40%, at least 50%, at least 60%, at least 70%, at least 75%, at least 80%, at least 90%, at least 92%, at least 95%, at least 96%, at least 97%, at least 98%, at least 99%, at least 100%, at least 200%, at least 300%, at least 400%, or at least 500% relative to a native protein. In one example, negative regulation is measured by transcriptional activity and effects on mitochondrial biogenesis. Examples of mutations that can be made to a PGC1α, Tfam, GABPA, and/or ERRα protein to increase its resistance to negative regulation are shown in Table 1:

TABLE 1

Exemplary Mutations

| Protein | Mutation (in human sequence) |
| --- | --- |
| PGC1α | S572A (e.g., of SEQ ID NO: 6) |
| Tfam | S55A, S56A, S61A (e.g., of SEQ ID NO: 8) |

TABLE 1-continued

Exemplary Mutations

| Protein | Mutation (in human sequence) |
| --- | --- |
| GABPA | T280E (e.g., of SEQ ID NO: 4) |
| ERRα | S19A (e.g., of SEQ ID NO: 2) |

2. Exemplary CARs

In some examples, the disclosed recombinant T cells can include a chimeric antigen receptor (CAR). CARs can be used to engineer T cells that target a tumor cell surface molecule for cancer immunotherapy. The CAR can be expressed from the same vector as PGC1α, Tfam, GABPA, and/or ERRα, or from a different vector. CARs are fusion proteins that include antigen recognition moieties and T-cell activation domains. Thus, the recombinant T cells provided herein that have increased PGC1α, Tfam, GABPA, and/or ERRα expression, can also be genetically modified to express CARs. For example, most B-cell malignancies express CD19, and thus adoptive transfer of anti-CD19 CAR T cells can be used to treat such tumors, such as lymphomas and leukemias.

CARs generally include an ectodomain (which includes a signal peptide, an antigen recognition region, and a spacer that provides flexibility and optimizes T cell and target cell engagement), a transmembrane domain (e.g., hydrophobic alpha helix, such as CD3-zeta or CD2, and optionally intracellular signaling domains), and an endodomain. A review of CARs and their design is provided in Jensen and Riddell (*Curr Opin Immunol.* 33:9-15, 2015, herein incorporated by reference) and Dotti et al., *Immunol Rev.* 257(1): doi10.1111/imr.12131 2014, herein incorporated by reference).

In one example, the ectodomain of CAR includes an antibody or antibody fragment (e.g., an scFv) specific for a tumor associated antigen (TAA). In one example, the ectodomain comprises a monoclonal antibody fragment. Examples of TAAs that can be targeted by CAR are shown in Table 2 and below (as well as Morello et al., *Cancer Discov* 6:133-46, 2016, herein incorporated by reference).

TABLE 2

Exemplary CAR Targets

| TAA | Tumor |
| --- | --- |
| CD19 | Liquid (e.g., leukemia, lymphoma) |
| HER1 | Adenocarcinoma (e.g., colorectal cancer, head and neck cancer) |
| HER2 | breast cancer, ovarian cancer, stomach cancer, uterine cancer |
| CD20 | Non-Hodgkin lymphoma |
| CD25 | T-cell lymphoma |
| CD33 | Acute myelogenous leukemia |
| CD52 | chronic lymphocytic leukemia |
| CEA | colorectal cancer, some gastric cancers, biliary cancer |
| Cancer antigen 125 (CA125) | ovarian cancer, mesothelioma, breast cancer |
| Alpha-fetoprotein (AFP) | hepatocellular carcinoma |
| Lewis Y | colorectal cancer, biliary cancer |
| TAG72 | adenocarcinomas including colorectal, pancreatic, gastric, ovarian, endometrial, mammary, and non-small cell lung cancer |
| Vascular endothelial growth factor | Colorectal cancer |
| Hypoglycosylated MUC1 | Epithelial cancers |

In one example, the TAA is a member of the EGF receptor family (e.g., HER1, 2, 3, and 4) or cytokine receptor (e.g., CD20, CD25, IL-13R, CD5, CD52, etc.). TAAs are proteins that are unique to cancer cells or are much more abundant on them, as compared to other cells, such as normal cells. For example HER2 is primarily found in breast cancers, while HER1 is primarily found in adenocarcinomas, which can be found in many organs, such as the pancreas, breast, prostate and colon.

Exemplary TAAs that can be targeted by a CAR, include but are not limited to: any of the various MAGEs (Melanoma-Associated Antigen E), including MAGE 1 (e.g., GenBank Accession Nos. M77481 and AAA03229), MAGE 2 (e.g., GenBank Accession Nos. L18920 and AAA17729), MAGE 3 (e.g., GenBank Accession Nos. U03735 and AAA17446), MAGE 4 (e.g., GenBank Accession Nos. D32075 and A06841.1), etc.; any of the various tyrosinases (e.g., GenBank Accession Nos. U01873 and AAB60319); mutant ras; mutant p53 (e.g., GenBank Accession Nos. X54156, CAA38095 and AA494311); p97 melanoma antigen (e.g., GenBank Accession Nos. M12154 and AAA59992); human milk fat globule (HMFG) associated with breast tumors (e.g., GenBank Accession Nos. S56151 and AAB19771); any of the various BAGEs (Human B melanoma-Associated Antigen E), including BAGEL (e.g., GenBank Accession No. Q13072) and BAGE2 (e.g., GenBank Accession Nos. NM_182482 and NP_872288), any of the various GAGEs (G antigen), including GAGE1 (e.g., GenBank Accession No. Q13065) or any of GAGE2-6; various gangliosides, CD25 (e.g., GenBank Accession Nos. NP 000408.1 and NM_000417.2).

Other TAAs that can be targeted by a CAR include HPV 16/18 and E6/E7 antigens associated with cervical cancers (e.g., GenBank Accession Nos. NC_001526, FJ952142.1, ADB94605, ADB94606, and U89349), mucin (MUC 1)-KLH antigen associated with breast carcinoma (e.g., GenBank Accession Nos. J03651 and AAA35756), CEA (carcinoembryonic antigen) associated with colorectal cancer (e.g., GenBank Accession Nos. X98311 and CAA66955), gp100 (e.g., GenBank Accession Nos. S73003 and AAC60634) associated with for example melanoma, MART1 antigens associated with melanoma (e.g., GenBank Accession No. NP_005502), cancer antigen 125 (CA125, also known as mucin 16 or MUC16) associated with ovarian and other cancers (e.g., GenBank Accession Nos. NM_024690 and NP_078966); alpha-fetoprotein (AFP) associated with liver cancer (e.g., GenBank Accession Nos. NM_001134 and NP_001125); Lewis Y antigen associated with colorectal, biliary, breast, small-cell lung, and other cancers; tumor-associated glycoprotein 72 (TAG72) associated with adenocarcinomas; and the PSA antigen associated with prostate cancer (e.g., GenBank Accession Nos. X14810 and CAA32915).

Other exemplary TAAs that can be targeted by a CAR include, but are not limited to, PMSA (prostate membrane specific antigen; e.g., GenBank Accession Nos. AAA60209 and AAB81971.1) associated with solid tumor neovasculature, as well prostate cancer; HER-2 (human epidermal growth factor receptor 2, e.g., GenBank Accession Nos. M16789.1, M16790.1, M16791.1, M16792.1 and AAA58637) associated with breast cancer, ovarian cancer, stomach cancer and uterine cancer, HER-1 (e.g., GenBank Accession Nos. NM_005228 and NP_005219) associated with lung cancer, anal cancer, and gliobastoma as well as adenocarcinomas; NY-ESO-1 (e.g. GenBank Accession Nos. U87459 and AAB49693) associated with melanoma, sarcomas, testicular carcinomas, and other cancers, hTERT (aka telomerase) (e.g., GenBank Accession. Nos. NM_198253 and NP_937983 (variant 1), NM_198255 and NP_937986 (variant 2)); proteinase 3 (e.g., GenBank Accession Nos. M29142, M75154, M96839, X55668, NM 00277, M96628, X56606, CAA39943 and AAA36342), and Wilms tumor 1 (WT-1, e.g. GenBank Accession Nos. NM_000378 and NP_000369 (variant A), NM_024424 and NP_077742 (variant B), NM_024425 and NP_077743 (variant C), and NM_024426 and NP_077744 (variant D)).

In one example the TAAs targeted by a CAR is CD52 (e.g., GenBank Accession. Nos. AAH27495.1 and CAI15846.1) associated with chronic lymphocytic leukemia; CD33 (e.g., GenBank Accession. Nos. NM_023068 and CAD36509.1) associated with acute myelogenous leukemia; and CD20 (e.g., GenBank Accession. Nos. NP_068769 NP_031667) associated with Non-Hodgkin lymphoma.

In one example the endodomain includes one or more costimulatory domains fused to CD3ζ such as CD28, CD137, or OX-40, such as a CD3zeta-CD28-41BB or CD3-zeta-CD28-OX40.

3. Exemplary TCR Sequences

In some examples, the disclosed recombinant T cells can include a recombinant T cell receptor (TCR). The TCR can be expressed from the same vector as PGC1α, Tfam, GABPA, and/or ERRα, or from a different vector. Introducing mutation-specific TCR genes into T cells for adoptive transfer allow, for tumor-specific therapy. A review of TCRs and their design is provided in Blankenstein et al. (*Curr Opin Immunol.* 33:112-9, 2015, herein incorporated by reference). Like CARs, TCRs that target a TAA (such as those listed above) can be used. In other examples, provided in Table 3, a normal cell can be targeted, where the normal cells are dispensable. Harris and Kranz (*Trends Pharmacol. Sci.* 37:220-30, 2016, herein incorporated by reference) provides an comparison of TCRs and CARs.

TABLE 3

Exemplary TCRs

| Tumor | TCR |
| --- | --- |
| Leukemia | WT1 |
| Multiple myeloma, melanoma | NY-ESO-1 |
| Melanoma | MART1, gp100 |
| Colorectal | CEA |

Making Recombinant T cells

1. Obtaining T Cells

In some examples, T cells are obtained from a subject to be treated, such as one having cancer. In some examples, T cells are obtained from a donor subject. T cells can be obtained from circulating peripheral blood. In some examples, aphersis or leukapheresis is used. In some examples, PBMCs are obtained, and T cells enriched for by using anti-CD3/anti-CD28 beads. In some examples, T cells are obtained from a tumor (e.g., tumor infiltrating lymphocytes).

2. Vectors

Nucleic acid molecules encoding a native or variant PGC1α, Tfam, GABPA, and/or ERRα protein can be incorporated into a vector. Similarly, nucleic acid molecules encoding a CAR or recombinant TCR can be incorporated into a vector, which may be the same or a different vector than the one containing the native or variant PGC1α, Tfam, GABPA, and/or ERRα coding sequence. Nucleic acid sequences coding for g a native or variant PGC1α, Tfam, GABPA, and/or ERRα such as those having at least 90%, at least 92%, at least 95%, at least 96%, at least 97%, at least 98%, or at least 99% sequence identity to those shown in a GenBank® Accession No. provided herein, can be routinely generated. Similarly, nucleic acid molecules coding for a CAR or recombinant TCR, such as those having at least 90%, at least 92%, at least 95%, at least 96%, at least 97%, at least 98%, or at least 99% sequence identity to a known a CAR or recombinant TCR, can be routinely generated. In addition, one of skill can readily construct a variety of clones containing functionally equivalent nucleic acids, such as nucleic acids which differ in sequence but which encode the same protein sequence. In some examples, such a sequence is optimized for expression in a host cell, such as a host T cell used to express the desired protein(s).

Nucleic acid molecules include DNA, cDNA and RNA sequences which encode a peptide. Silent mutations in the coding sequence result from the degeneracy (i.e., redundancy) of the genetic code, whereby more than one codon can encode the same amino acid residue. Thus, for example, leucine can be encoded by CTT, CTC, CTA, CTG, TTA, or TTG; serine can be encoded by TCT, TCC, TCA, TCG, AGT, or AGC; asparagine can be encoded by AAT or AAC; aspartic acid can be encoded by GAT or GAC; cysteine can be encoded by TGT or TGC; alanine can be encoded by GCT, GCC, GCA, or GCG; glutamine can be encoded by CAA or CAG; tyrosine can be encoded by TAT or TAC; and isoleucine can be encoded by ATT, ATC, or ATA.

Codon preferences and codon usage tables for a particular species can be used to engineer isolated nucleic acid molecules encoding a PGC1α, Tfam, GABPA, ERRα, CAR and/or recombinant TCR protein that take advantage of the codon usage preferences of that particular species. For example, the PGC1α, Tfam, GABPA, ERRα, CAR and/or recombinant TCR protein expressed from the vector(s) can be designed to have codons that are preferentially used by a particular organism of interest (e.g., in one whom the recombinant T cells are introduced).

A nucleic acid encoding a PGC1α, Tfam, GABPA, ERRα, CAR and/or recombinant TCR protein can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). A wide variety of cloning and in vitro amplification methodologies are well known to persons skilled in the art. In addition, nucleic acids encoding sequences encoding a PGC1α, Tfam, GABPA, ERRα, CAR and/or recombinant TCR protein can be prepared by cloning techniques. Examples of appropriate cloning and sequencing techniques, and instructions sufficient to direct persons of skill through cloning are found in Sambrook et al. (ed.), Molecular Cloning: A Laboratory Manual 2nd ed., vol. 1-3, Cold Spring Harbor Laboratory Press, Cold Spring, Harbor, N.Y., 1989, and Ausubel et al., (1987) in "Current Protocols in Molecular Biology," John Wiley and Sons, New York, N.Y.

Nucleic acid sequences encoding a PGC1α, Tfam, GABPA, ERRα, CAR and/or recombinant TCR protein can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. One of skill would recognize that while chemical synthesis of DNA is generally limited to sequences of about 100 bases, longer sequences may be obtained by the ligation of shorter sequences.

In one example, a PGC1α, Tfam, GABPA, ERRα, CAR and/or recombinant TCR protein is prepared by inserting the cDNA which encodes the PGC1α, Tfam, GABPA, ERRα, CAR and/or recombinant TCR protein into a vector. The insertion can be made so that the protein(s) is read in frame so that the protein(s) is produced. Techniques for preparing recombinant vectors (e.g., plasmid or virus) containing a heterologous nucleic acid sequence encoding the PGC1α, Tfam, GABPA, ERRα, CAR and/or recombinant TCR protein are known.

The nucleic acid coding sequence for a PGC1α, Tfam, GABPA, ERRα, CAR and/or recombinant TCR protein can be inserted into an expression vector including, but not limited to a plasmid, virus or other vehicle that can be manipulated to allow insertion or incorporation of sequences and can be expressed in a T cell. Methods of expressing coding sequences from a vector are known in the art. Biologically functional viral and plasmid DNA vectors capable of expression and replication in a T cell are known in the art. The expression vector can contain additional elements necessary for the transfer and subsequent replication of the expression vector containing the PGC1α, Tfam, GABPA, ERRα, CAR and/or recombinant TCR protein coding sequence in the T cell. Examples of such elements include, but are not limited to, origins of replication and selectable markers, such as a thymidine kinase gene or an antibiotic resistance marker, a 'suicide gene' like an inducible caspase 9, or a truncated (nonfunctional) EGFR.

Nucleic acid sequences encoding a PGC1α, Tfam, GABPA, ERRα, CAR and/or recombinant TCR protein can be operatively linked to expression control sequences. In one example, the PGC1α, Tfam, GABPA, and/or ERRα protein is expressed from the same expression control sequence as the CAR and/or recombinant TCR protein. An expression control sequence operatively linked to a PGC1α, Tfam, GABPA, ERRα, CAR and/or recombinant TCR protein coding sequence is ligated such that expression of the PGC1α, Tfam, GABPA, ERRα, CAR and/or recombinant TCR protein coding sequence is achieved under conditions compatible with the expression control sequences. Exemplary expression control sequences include, but are not limited to appropriate promoters, enhancers, transcription terminators, a start codon (i.e., ATG) in front of a PGC1α, Tfam, GABPA, ERRα, CAR and/or recombinant TCR protein-encoding gene, splicing signal for introns, maintenance of the correct reading frame of that gene to permit proper translation of mRNA, and stop codons. Examples of expression control elements that can be used include, but are not limited to, lac system, operator and promoter regions of phage lambda, and promoters derived from polyoma, adenovirus, retrovirus or SV40. Additional operational elements include, but are not limited to, leader sequence, termination codons, polyadenylation signals and any other sequences necessary for the appropriate transcription and subsequent translation of the nucleic acid sequence encoding the PGC1α, Tfam, GABPA, ERRα, CAR and/or recombinant TCR protein in the T cell. In one example, the promoter is a lentiviral promoter. In one example, an IRES is used to drive expression. In some examples, two promoters are used.

Viral vectors can be prepared that encode a PGC1α, Tfam, GABPA, ERRα, CAR and/or recombinant TCR protein. In one example, PGC1α, Tfam, GABPA, and/or ERRα, are expressed from the same vector as a CAR and/or recombinant TCR protein. In one example, PGC1α, Tfam, GABPA, and/or ERRα, are expressed from a separate vector as a CAR and/or recombinant TCR protein. Exemplary viral vectors that can be used include, but are not limited to, polyoma, SV40, adenovirus, vaccinia virus, adeno-associated virus, herpes viruses including HSV and EBV, Sindbis viruses, alphaviruses and retroviruses of avian, murine, and human origin. Baculovirus (Autographa californica multinuclear polyhedrosis virus; AcMNPV) vectors can also be used. Other suitable vectors include orthopox vectors, avipox vectors, fowlpox vectors, capripox vectors, suipox vectors, lentiviral vectors, alpha virus vectors, and poliovirus vectors. Specific exemplary vectors are poxvirus vectors such as vaccinia virus, fowlpox virus and a highly attenuated vaccinia virus (MVA), adenovirus, baculovirus and the like. Pox viruses of use include orthopox, suipox, avipox, and capripox virus. Orthopox include vaccinia, ectromelia, and raccoon pox. One example of an orthopox of use is vaccinia. Avipox includes fowlpox, canary pox and pigeon pox. Capripox include goatpox and sheeppox. In one example, the suipox is swinepox. Other viral vectors that can be used include other DNA viruses such as herpes virus and adenoviruses, and RNA viruses such as retroviruses and polio.

3. Expression of Recombinant Nucleic Acid Molecules

Exemplary methods that can be used to introduce a vector that includes a PGC1α, Tfam, GABPA, ERRα, CAR and/or recombinant TCR protein coding sequence into a eukaryotic cell, such as a T cell, include but are not limited to: calcium phosphate coprecipitates; mechanical procedures such as microinjection, electroporation, insertion of a plasmid encased in liposomes, and infection with a viral vector (see for example, *Eukaryotic Viral Vectors*, Cold Spring Harbor Laboratory, Gluzman ed., 1982).

After introducing the vector that includes a PGC1α, Tfam, GABPA, ERRα, CAR and/or recombinant TCR protein coding sequence into the T cell, the T cell can be cultured under conditions that permit expression of PGC1α, Tfam, GABPA, ERRα, CAR and/or recombinant TCR protein(s). Such methods can include incubating or culturing the recombinant T cells in the presence of a culture media under conditions that allow for expansion of the recombinant T cells. In some examples, the method of ex vivo expansion can include incubating the recombinant T cells in a culture medium, such as serum-free media (e.g., AIM V® medium) or human AB serum. The method of ex vivo expansion can further include contacting the recombinant T cells with a gamma-chain cytokine (such as interleukin 2 (IL-2) and/or IL-15), anti-CD3, anti-CD28, or combinations thereof. In some examples, the anti-CD3 and the anti-CD28 are present on a bead. The amount of anti-CD3, anti-CD28 and IL-2 can vary, such as from 3-10 µg/mL anti-CD3 (immobilized), 2-10 ug/mL anti-CD28, and 10 U/mL to 6000 U/mL IL-2. In some examples, additional agents are present in the ex vivo culture, such as gamma chain cytokines (as well as reagents provided in U.S. Pat. No. 5,126, 132). In typical examples, the recombinant T cells are expanded ex vivo at 37° C.

In some examples, the recombinant T cells are incubated ex vivo to allow for sufficient expansion (e.g., reproduction of the recombinant T cells) as needed for transplantation, such as a period of days or weeks (such as at least 1 week, at least 2 weeks, at least 3 weeks, at least 4 weeks, or at least 6 weeks). In some examples, the recombinant T cells are allowed to expand until millions or billions of recombinant T cells are obtained, such as tens of billions recombinant T cells.

In some examples, the method includes monitoring the expanding recombinant T cells, for example determining the number of cells, determining or measuring the mitochondrial activity (e.g., oxidative metabolism), determining or measuring the mitochondrial mass of the TILs, determining or measuring nucleic acid and/or protein expression of one or more of PGC1α, Tfam, GABPA, ERRα, CAR and/or recombinant TCR.

Methods of Using Recombinant T Cells

The recombinant T cells provided herein, for example generated using the disclosed methods, can be used in cancer immunotherapy, for example to treat a tumor in vivo. Solid and liquid tumors can be treated with the disclosed methods. Specific examples of tumors that can be treated include, but are not limited to, a leukemia, lymphoma, colorectal cancer, melanoma, cervical cancer, lung cancer, ovarian cancer, bladder cancer, breast cancer, or head and neck cancer. Other examples are provided herein.

For example, an effective amount of the disclosed recombinant T cells (such as at least $1 \times 10^6$ recombinant T cells, at least $2 \times 10^6$ recombinant T cells, at least $5 \times 10^6$ recombinant T cells, at least $1 \times 10^7$ recombinant T cells, at least $1 \times 10^8$ recombinant T cells, at least $1 \times 10^9$ recombinant T cells, at least $1 \times 10^{10}$ recombinant T cells, at least $5 \times 10^{10}$, or at least $5 \times 10^{11}$ recombinant T cells) are administered to the subject, thereby treating a tumor (such as a primary tumor and/or a metastasis) in the subject. In some examples, the recombinant T cells are administered intravenously. In one example, the method further includes administering an effective amount of nonmyeloablative chemotherapy or radiotherapy to deplete native lymphocytes prior to administering an effective amount of the recombinant T cell (but prior to harvesting T cells if the T cells used are from the same patient). In some examples, such subjects are also administered an effective amount of IL-2 (such as 10,000 to 100,000 units/kg body weight) to the subject before, after, or both before and after, administering the disclosed recombinant T cells.

In some examples the subject administered the disclosed recombinant T cells was previously treated unsuccessfully with a chemotherapy, radiation therapy, biologic therapy, or combinations thereof (e.g., the tumor in the subject did not significantly decrease in size or even increased in size, and/or metastasized). In some examples the subject has a tumor that was not responsive to a PD-1 antagonist or a PD-L1 antagonist (e.g., the tumor in the subject did not significantly decrease in size or even increased in size, and/or metastasized), such as an antibody that specifically binds PD-1 or PD-L1, such as Atezolizumab, MPDL3280A, BNS-936558 (Nivolumab), Pembrolizumab, Pidilizumab, CT011, AMP-224, AMP-514, MEDI-0680, BMS-936559, BMS935559, MEDI-4736, MPDL-3280A, MSB-0010718C.

Additional Therapies

The subject treated with the disclosed recombinant T cells can receive one or more additional therapies, such as one or more of an effective amount of chemotherapy an effective amount of radiotherapy (for example administration of radioactive material or energy (such as external beam therapy) to the tumor site to help eradicate the tumor or shrink it), an effective amount of a biologic, and surgery (for example surgical resection of the cancer or a portion of it).

In one example, the subject is further treated with one or more chemotherapeutic agents. Chemotherapeutic agents include any chemical agent with therapeutic usefulness in the treatment of diseases characterized by abnormal cell growth, such as cancer. One of skill in the art can readily identify a chemotherapeutic agent of use (see for example, Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., © 2000 Churchill Livingstone, Inc; Baltzer, L., Berkery, R. (eds): *Oncology Pocket Guide to Chemotherapy*, 2nd ed. St. Louis, Mosby-Year Book, 1995; Fischer, D. S., Knobf, M. F., Durivage, H. J. (eds): *The Cancer Chemotherapy Handbook*, 4th ed. St. Louis, Mosby-Year Book, 1993; Chabner and Longo, *Cancer Chemotherapy and Biotherapy: Principles and Practice* (4th ed.). Philadelphia: Lippincott Willians & Wilkins, 2005; Skeel, *Handbook of Cancer Chemotherapy* (6th ed.). Lippincott Williams & Wilkins, 2003). Combination chemotherapy is the administration of more than one agent to treat cancer.

Examples of chemotherapeutic agents that can be used include alkylating agents, antimetabolites, natural products, or hormones and their antagonists. Examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine). Specific non-limiting examples of alkylating agents are temozolomide and dacarbazine. Examples of antimetabolites include folic acid analogs (such as methotrexate), pyrimidine analogs (such as 5-FU or cytarabine), and purine analogs, such as mercaptopurine or thioguanine. Examples of natural products include vinca alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitocycin C), and enzymes (such as L-asparaginase). Examples of miscellaneous agents include platinum coordination complexes (such as cis-diamine-dichloroplatinum II also known as cisplatin), substituted ureas (such as hydroxyurea), methyl hydrazine derivatives (such as procarbazine), and adrenocrotical suppressants (such as mitotane and aminoglutethimide). Examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), anti-estrogens (such as tamoxifen), and androgens (such as testerone proprionate and fluoxymesterone).

Examples of commonly used chemotherapy drugs include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin and calcitriol. Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech).

Additional therapeutic agents that can be used include microtubule binding agents, DNA intercalators or cross-linkers, DNA synthesis inhibitors, DNA and/or RNA transcription inhibitors, antibodies, enzymes, enzyme inhibitors, gene regulators, angiogenesis inhibitors. These agents (which are administered at a therapeutically effective amount) and treatments can be used alone or in combination. Methods and therapeutic dosages of such agents are known to those skilled in the art, and can be determined by a skilled clinician.

Microtubule binding agent refers to an agent that interacts with tubulin to stabilize or destabilize microtubule formation thereby inhibiting cell division. Examples of microtubule binding agents that can be used in conjunction with the disclosed therapy include, without limitation, paclitaxel, docetaxel, vinblastine, vindesine, vinorelbine (navelbine), the epothilones, colchicine, dolastatin 15, nocodazole, podophyllotoxin and rhizoxin. Analogs and derivatives of such compounds also can be used and are known to those of ordinary skill in the art. For example, suitable epothilones and epothilone analogs are described in International Publication No. WO 2004/018478. Taxoids, such as paclitaxel and docetaxel, as well as the analogs of paclitaxel taught by U.S. Pat. Nos. 6,610,860; 5,530,020; and 5,912,264 can be used.

Suitable DNA and/or RNA transcription regulators, including, without limitation, actinomycin D, daunorubicin, doxorubicin and derivatives and analogs thereof also are suitable for use in combination with the disclosed therapies. DNA intercalators and cross-linking agents that can be administered to a subject include, without limitation, cisplatin, carboplatin, oxaliplatin, mitomycins, such as mitomycin C, bleomycin, chlorambucil, cyclophosphamide and derivatives and analogs thereof. DNA synthesis inhibitors suitable for use as therapeutic agents include, without limitation, methotrexate, 5-fluoro-5'-deoxyuridine, 5-fluorouracil and analogs thereof. Examples of suitable enzyme inhibitors include, without limitation, camptothecin, etoposide, formestane, trichostatin and derivatives and analogs thereof. Suitable compounds that affect gene regulation include agents that result in increased or decreased expression of one or more genes, such as raloxifene, 5-azacytidine, 5-aza-2'-deoxycytidine, tamoxifen, 4-hydroxytamoxifen, mifepristone and derivatives and analogs thereof.

The disclosed methods can further include administering to the subject a therapeutically effective amount of an immunotherapy. Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech). The immunotherpautic agent can be a PD-1 antagonist or a PD-L1 antagonist, such as an antibody that specifically binds PD-1 or PD-L1, such as Atezolizumab, MPDL3280A, BNS-936558 (Nivolumab), Pembrolizumab, Pidilizumab, CT011, AMP-224, AMP-514, MEDI-0680, BMS-936559, BMS935559, MEDI-4736, MPDL-3280A, MSB-0010718C. The immunotherpautic agent can also be a CTLA-4, LAG-3, or B7-H3 antagonist, such as Tremelimumab, BMS-986016, and MGA271.

Non-limiting examples of anti-angiogenic agents include molecules, such as proteins, enzymes, polysaccharides, oligonucleotides, DNA, RNA, and recombinant vectors, and small molecules that function to reduce or even inhibit blood vessel growth. Examples of suitable angiogenesis inhibitors include, without limitation, angiostatin K1-3, staurosporine, genistein, fumagillin, medroxyprogesterone, suramin, interferon-alpha, metalloproteinase inhibitors, platelet factor 4, somatostatin, thromobospondin, endostatin, thalidomide, and derivatives and analogs thereof. For example, in some embodiments the anti-angiogenesis agent is an antibody that specifically binds to VEGF (e.g., Avastin, Roche) or a VEGF receptor (e.g., a VEGFR2 antibody). In one example the anti-angiogenic agent includes a VEGFR2 antibody, or DMXAA (also known as Vadimezan or ASA404; available commercially, e.g., from Sigma Corp., St. Louis, Mo.) or both. The anti-angiogenic agent can be bevacizumab, sunitinib, an anti-angiogenic tyrosine kinase inhibitors (TKI), such as sunitinib, xitinib and dasatinib. These can be used individually or in any combination.

Exemplary kinase inhibitors include Gleevac, Iressa, and Tarceva, sunitinib, sorafenib, anitinib, and dasatinib that prevent phosphorylation and activation of growth factors. Antibodies that can be used include Herceptin and Avastin that block growth factors and the angiogenic pathway. These can be used individually or in combination.

In some examples, the additional therapeutic agent administered is a biologic, such as a monoclonal antibody, for example, 3F8, Abagovomab, Adecatumumab, Afutuzumab, Alacizumab, Alemtuzumab, Altumomab pentetate, Anatumomab mafenatox, Apolizumab, Arcitumomab, Bavituximab, Bectumomab, Belimumab, Besilesomab, Bevacizumab, Bivatuzumab mertansine, Blinatumomab, Brentuximab vedotin, Cantuzumab mertansine, Capromab pendetide, Catumaxomab, CC49, Cetuximab, Citatuzumab bogatox, Cixutumumab, Clivatuzumab tetraxetan, Conatumumab, Dacetuzumab, Detumomab, Ecromeximab, Eculizumab, Edrecolomab, Epratuzumab, Ertumaxomab, Etaracizumab, Farletuzumab, Figitumumab, Galiximab, Gemtuzumab ozogamicin, Girentuximab, Glembatumumab vedotin, Ibritumomab tiuxetan, Igovomab, Imciromab, Intetumumab, Inotuzumab ozogamicin, Ipilimumab, Iratumumab, Labetuzumab, Lexatumumab, Lintuzumab, Lorvotuzumab mertansine, Lucatumumab, Lumiliximab, Mapatumumab, Matuzumab, Mepolizumab, Metelimumab, Milatuzumab, Mitumomab, Morolimumab, Nacolomab tafenatox, Naptumomab estafenatox, Necitumumab, Nimotuzumab, Nofetumomab merpentan, Ofatumumab, Olaratumab, Oportuzumab monatox, Oregovomab, Panitumumab, Pemtumomab, Pertuzumab, Pintumomab, Pritumumab, Ramucirumab, Rilotumumab, Rituximab, Robatumumab, Satumomab pendetide, Sibrotuzumab, Sonepcizumab, Tacatuzumab tetraxetan, Taplitumomab paptox, Tenatumomab, TGN1412, Ticilimumab (tremelimumab), Tigatuzumab, TNX-650, Trastuzumab, Tremelimumab, Tucotuzumab celmoleukin, Veltuzumab, Volociximab, Votumumab, Zalutumumab, or combinations thereof.

In some examples, the subject is administered an effective amount of nonmyeloablative chemotherapy or radiotherapy to deplete native lymphocytes prior to administering an effective amount of the recombinant T cells. For example, the subject may receive an effective amount of nonmyeloablative chemotherapy, such as administration of one or more of cisplatin, fludarabine, idarubicin, melphalan, ara-C, 2-chlorodeoxyadenosine, antithymocyte globulin, and cyclophosphamide (such as 10 to 50 mg/kg body weight). In some examples, the subject receives an effective amount of solid tumor irradiation, thymic irradiation, or total body irradiation (e.g., 2 Gy), or combinations thereof. Other specific examples are provided in Phan and Rosenberg, *Cancer Control* 20:289-97, 2013.

In some examples, following administration of the recombinant T cells, the subject is administered one or more of an effective amount of tacrolimus, cyclosporine, and/or methotrexate.

Clinical Response

Such methods can treat the tumor in the subject by reducing the volume or weight of the tumor, reducing the number of metastases, reducing the size or weight of a metastasis, or combinations thereof. In some examples a metastasis is cutaneous or subcutaneous. Thus, in some examples, administration of disclosed recombinant T cells treats a tumor in a subject by reducing the size or volume of the tumor by at least 10%, at least 20%, at least 30%, at least 40%, at least 50%, at least 60%, at least 70%, at least 75%, at least 80%, at least 90%, at least 95%, at least 98% or at least 99%, for example as compared to no administration of disclosed recombinant T cells or administration of recombinant T cells not containing a vector expressing a native or variant PGC1α, Tfam, GABPA, and/or ERRα coding sequence. In some examples, administration of disclosed recombinant T cells treats a tumor in a subject by reducing the weight of the tumor by at least 10%, at least 20%, at least 30%, at least 40%, at least 50%, at least 60%, at least 70%, at least 75%, at least 80%, at least 90%, at least 95%, at least 98% or at least 99%, for example as compared to no administration of disclosed recombinant T cells or administration of recombinant T cells not containing a vector expressing a native or variant PGC1α, Tfam, GABPA, and/or ERRα coding sequence. In some examples, administration of disclosed recombinant T cells treats a tumor in a subject by reducing the size or volume of a metastasis by at least 10%, at least 20%, at least 30%, at least 40%, at least 50%, at least 60%, at least 70%, at least 75%, at least 80%, at least 90%, at least 95%, at least 98% or at least 99%, for example as compared to no administration of disclosed recombinant T cells or administration of recombinant T cells not containing a vector expressing a native or variant PGC1α, Tfam, GABPA, and/or ERRα coding sequence. In some examples, administration of disclosed recombinant T cells treats a tumor in a subject by reducing the number of metastases by at least 10%, at least 20%, at least 30%, at least 40%, at least 50%, at least 60%, at least 70%, at least 75%, at least 80%, at least 90%, at least 95%, at least 98% or at least 99% for example as compared to no administration of disclosed recombinant T cells or administration of recombinant T cells not containing a vector expressing a native or variant PGC1α, Tfam, GABPA, and/or ERRα coding sequence. In some examples, combinations of these effects are achieved.

Compositions and Kits

Also provided are compositions and kits that can be used with the disclosed methods. In some examples, the composition or kit includes one or more disclosed recombinant T cells and/or vectors, for example with a pharmaceutically acceptable carrier. The kits can include additional reagents, such as one or more of anti-CD3, anti-CD28, IL-2, and IL-15. In some examples, in a kit, such reagents are present in a separate container. In one example, anti-CD3 and anti-CD28 are in the same container, and may be present on a bead for example. In some examples, the kit further includes one or more of a transfection reagent, culture medium, antibiotic, IL-2, IL-15, and IL-7, optionally wherein such reagents are present in separate containers. In some examples the kit or composition includes media in which the recombinant T cells can be cultured or expanded ex vivo, such as AIM V® media.

Example 1

Materials and Methods

This example provides the materials and methods used to generate the data discussed in the Examples below.

Mice

All animal work was done in accordance with the Institutional Animal Care and Use Committee of the University of Pittsburgh. All mice were housed in specific pathogen free conditions prior to use. C57/BL6, SJ/L (Thy1.1), Ppargc1a$^{f/f}$, Cd4$^{Cre}$, Foxp3$^{GFP.Cre.ERT2}$, Foxp3$^{DTR.GFP}$ and OT-I mice were obtained from The Jackson Laboratory.

Cell Lines, Antibodies, and Other Reagents

B16-F10 and LLC were obtained from ATCC. MC38 was obtained from Dario Vignali. B16$^{OVA}$ (MO5) was obtained from Per Basse and Lou Falo. OVA-expressing Vaccinia virus was originally generated by Yewdell and Bennink and obtained from Jonathan Powell. Most antibodies for flow cytometry were obtained from BioLegend. MitoTracker Green FM, MitoTracker Deep Red FM, tetramethylrhodamine ester (TMRE), and H2-DCFDA were obtained from ThermoFisher. VDAC antibody was obtained from Abcam. LC3B, pAkt, pFoxo1/3a antibodies were obtained from Cell Signaling Technologies and detected after surface staining with simultaneous fixation and permeabilization in 1.5% PFA made up in 1× Permeabilization buffer (eBioscience). 2-NBD-glucose, m-divi-1, and Akt inhibitor VIII were purchased from Cayman Chemical. PGC1α antibody (H-300) was obtained from Santa Cruz Biotechnology, and was detected using the Foxp3 Fix/Perm kit (eBioscience) and Alexa Fluor 647 or Alexa Fluor 488-conjugated anti-rabbit IgG (Jackson Immunoresearch). Anti-PD-1 blocking antibody (J43) and its hamster IgG control were obtained from Bio-X-Cell. CellTrace Violet was from eBioscience, and CFSE was from BioLegend.

T Cell Osolations from Lymph Node and Tumor and Adoptive Transfer

Spleen and lymph node CD8$^+$ T cells were isolated from 6-8 week-old OT-I (Thy1.2 or Thy1.1) mice. Tissue was harvested, mechanically disrupted, and incubated with a biotinylated antibody cocktail consisting of antibodies (BioLegend) to B220, CD11b, CD11c, CD16/32, CD19, CD25, CD105, NK1.1, TCRγδ, and CD4. After a wash step, cells were incubated with streptavidin-coated magnetic nanoparticles (BioLegend). After washing, CD8$^+$ cells were isolated by applying a magnetic field and removing untouched cells. In some experiments, these OT-I CD8$^+$ T cells were also labeled with the proliferation dye CellTrace Violet according to the manufacturer's protocol. Mice bearing B16$^{OVA}$ tumors or immunized with Vaccinia$^{OVA}$ received cells intravenously. To obtain single-cell suspensions of tumor infiltrating lymphocytes, tumor bearing mice were sacrificed and tumors were harvested. Excised, whole tumors were injected repeatedly using 20 G needles with 2 mg/mL collagenase type VI, 2 U/mL hyluronidase (Dispase), and 10 U/mL DNAse I (Sigma) in buffered RPMI with 10% FBS and incubated for 30 min at 37° C. Tumors were then mechanically disrupted between frosted glass slides and filtered to remove particulates, then vortexed for 2 minutes. In many experiments (especially prior to sorting), tumor homogenates were debulked of tumor cells using CD105-biotin mediated magnetic depletion.

Patients and Specimens

Peripheral venous blood samples were obtained from HNC patients with stage III/IVA disease previously untreated. Tumor biopsies or surgical tumor specimens were preserved for a maximum of 12 hours in complete media until tumor infiltrating lymphocytes were isolated.

Human Tumor Infiltrating Lymphocyte (TIL) Isolation

Fresh tumors from patients with HNC were minced into small pieces manually or using a gentleMACS dissociator (Miltenyi Biotec), then transferred to 70 μm cell strainers (BD) and mechanically separated using the plunger of a 5-mL syringe. The cells passing through the cell strainer were collected, washed and subjected to Ficoll-Hypaque gradient centrifugation. After centrifugation, mononuclear cells were recovered and immediately used for experiments.

Human PBMC Isolation from Peripheral Blood

Blood from healthy donors (Western Pennsylvania blood bank) or patients with HNC treated with cetuximab during or within 1 month of treatment (UPCI clinical trial #08-013 NCT 01218048). Lymphocytes were purified by Ficoll-Paque PLUS centrifugation following standard protocol (Amersham Biosciences), pulsed with 2NBDG, and stained for flow cytometry.

Metabolism Assays

Single-cell metabolic capacity was assayed by flow cytometry. Specifically, 2-NBD-glucose (Cayman Chemical) and MitoTracker FM dyes (ThermoFisher) were utilized to assay the propensity of cells to take up glucose or generate intermediates via their mitochondria. Nondraining and draining lymph node or tumor preparations were pulsed with 20 μM 2-NBDG in 5% FBS-containing media for 30 mM at 37° C. Cells were surface stained and loaded with MitoTracker FM dyes or TMRE to measure mitochondrial mass and function.

A Seahorse XFe96 Bioanalyzer was utilized to measure metabolic flux in real-time. T cells were plated on Cell-Tak coated Seahorse culture plates (50,000-100,000 T cells/well) in assay media consisting of minimal, unbuffered DMEM supplemented with 1% BSA and 25 mM glucose, 1 mM pyruvate, and 2 mM glutamine Basal extracellular acidification and oxygen consumption rates were taken for 30 minutes. Cells were stimulated with oligomycin (2 μM), FCCP (0.5 μM), 2-deoxyglucose (100 mM) and rotenone/antimycin A (100 μM) to obtain maximal respiratory and control values. Spare respiratory capacity is measured as the difference between basal OCR values and maximal OCR values obtained after FCCP uncoupling.

Electron Microscopy

CD8$^+$ T cells were sorted from LNs and TIL and fixed in 4% glutaraldehyde, then sectioned and stained for electron microscopy as previously described. (Li et al., 2013)

Retroviral Expression

PGC1α was originally generated by Dr. B. Spiegelman, obtained from Addgene (plasmid 1026) (Monsalve et al., 2000), and cloned into an MSCV-driven retroviral expression vector which also encodes an IRES-mCherry cassette, from Dario Vignali. This vector was transiently transfected into Phoenix ecotropic cells. OT-I T cell were stimulated with SIINFEKL peptide at 250 ng/mL in the presence of 100 U/mL IL-2 for 24 h. Retroviral supernatants were harvested, and filtered, and supplemented with 6 μg/mL polybrene. OT-I T cell cultures were spinduced with the retroviral supernatant for 90 min at 2500 rpm. 24 h later spinduction this was repeated. Cells were then expanded and sorted for mCherry expression prior to analysis and adoptive transfer.
B16$^{OVA}$ In Vitro Stimulation Freshly isolated OT-I splenocytes or purified, previously activated OT-I CD8$^+$ T cells were CellTrace Violet labeled and plated at various ratios on B16 or B16$^{OVA}$ cells in 10% RPMI for 72 h. Proliferation and mitochondrial mass of the T cells was examined flow cytometrically.

$T_{reg}$ Cell Suppression Assay

Lymph nodes and spleens from Foxp3 reporter mice (Foxp3$^{DTR.GFP}$) were sorted based on expression of CD4 and GFP, then cocultured with CellTrace Violet-labeled CD8$^+$ T cells from WT mice at a 1:4 ratio ($T_{reg}$:$T_{eff}$ cell) in the presence of antigen presenting cells (CD4$^-$CD8$^-$ splenic cells at a 2:1 APC:T cell ratio) and 1 µg/mL anti-CD3. After 72 h, proliferation and mitochondrial mass of the CD8$^+$ T cells were analyzed by flow cytometry.

Figure 13A:
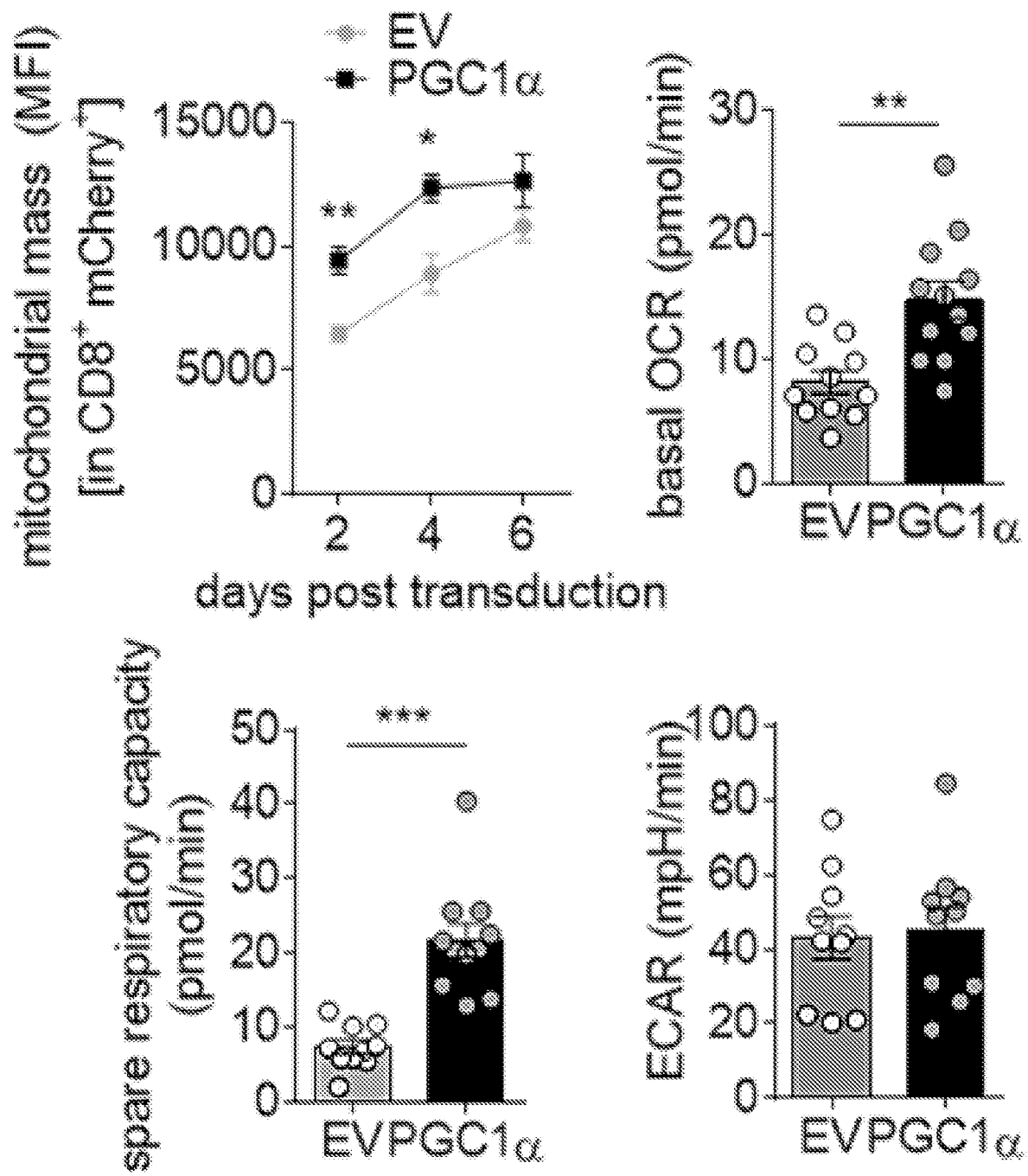

Fuel Usage Test 100,000 previously activated, transduced T cells (Generated in FIG. 13) were plated on CellTak-coated Seahorse plates in minimal, unbuffered Seahorse media containing glucose, and glutamine. Basal measurements were taken and then cells were uncoupled with FCCP and subjected to inhibition by UK5099, etomoxir, and BPTES. FIG. 13A shows the percentage of the total FCCP uncoupled OCR inhibited by these agents.

Example 2

Tumor Infiltrating T Cells Display Decreased Mitochondrial Mass

To assay the metabolic capacity of tumor-infiltrating T cells, flow cytometric analyses were used. Mitochondrial function and mass were measured using MitoTracker Deep Red FM (a membrane permeable, carbocyanine-based dye for mitochondria used previously to stain mitochondrial mass) (Cottet-Rousselle et al., 2011) and competency for glucose uptake using fluorescently labeled 2-NBD-glucose (2NBDG) in T cells infiltrating implantable tumors. While MitoTracker Deep Red has been shown to be membrane potential sensitive in some systems, uncoupling using CCCP showed that, using our staining protocols, MitoTracker Deep Red was highly resistant to collapse of membrane potential, especially compared to TMRE, a well-known membrane-potential sensitive dye (FIG. 1A).

Figure 1D:
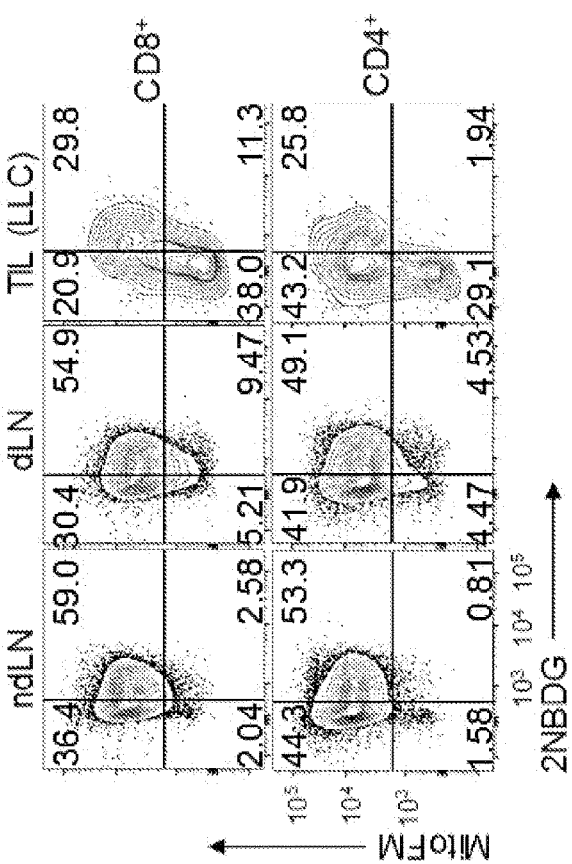
Figure 1E:
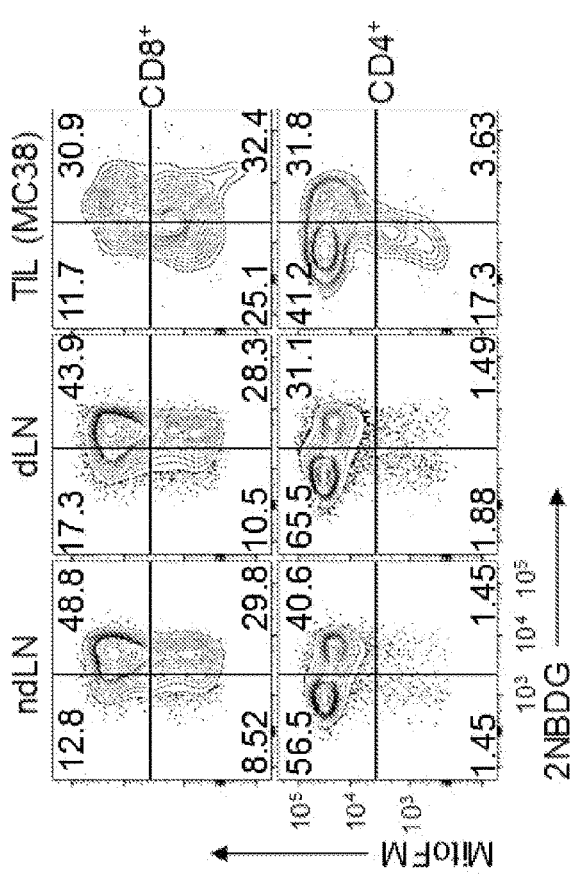
Figure 2A:
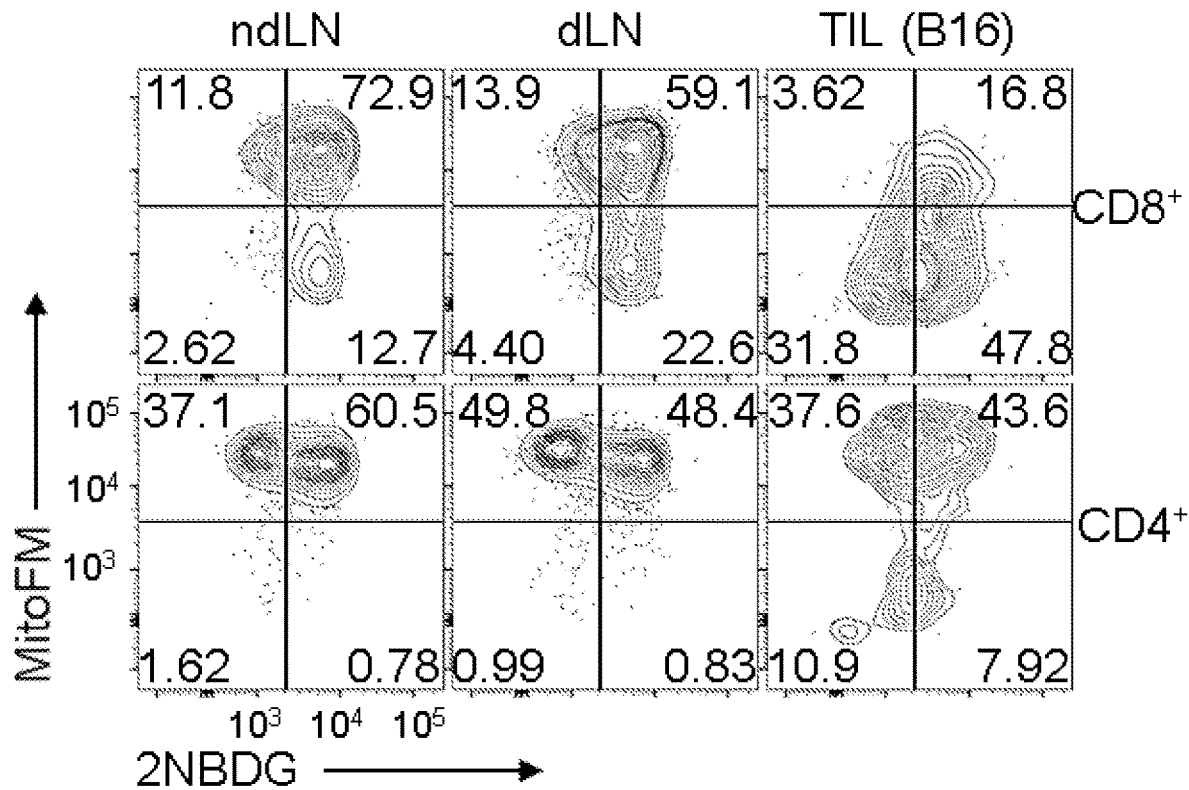
FIGS. 2A-2E. Tumor-infiltrating CD8+ T cells display suppressed mitochondrial function and mass. (A), Representative flow cytogram of nondraining (ndLN), draining (dLN) lymph node, or tumor-infiltrating lymphocyte (TIL) preparations from C57/BL6 mice inoculated with B16 melanoma cells 12 d prior, gated on CD8 or CD4 as indicated. (B), Tabulated flow cytometric data from CD8+ T cells isolated from mice bearing the indicated tumor types. Each circle represents an individual animal. (C), Transmission electron microscopy of activated or tumor-infiltrating CD8+ T cells. (D) MitoTracker FM staining of CD8+ T cells from PBL or TIL of HNSCC patients. (E) OCR trace (left) and metabolic analysis panels (middle, right) from CD8+ T cells isolated from the indicated sites from B16-bearing animals. T cells activated 24 h with anti-CD3/anti-CD28 (Teff) are included as a control. Spare respiratory capacity is calculated as the difference between initial, basal OCR values and the maximal OCR values achieved after FCCP uncoupling. Data represent the mean or are representative of 3-5 independent experiments. *, p<0.05, p<0.01, *p<0.001 by unpaired t-test. Error bars indicate s.e.m.
Figure 2C:
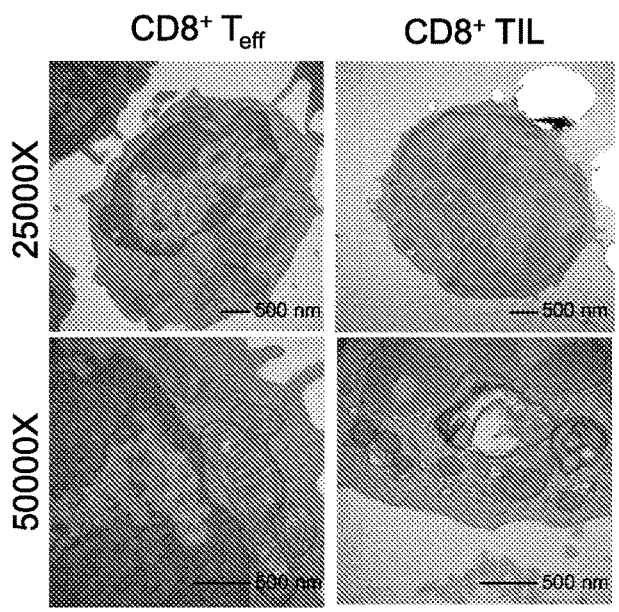
Figure 2B:
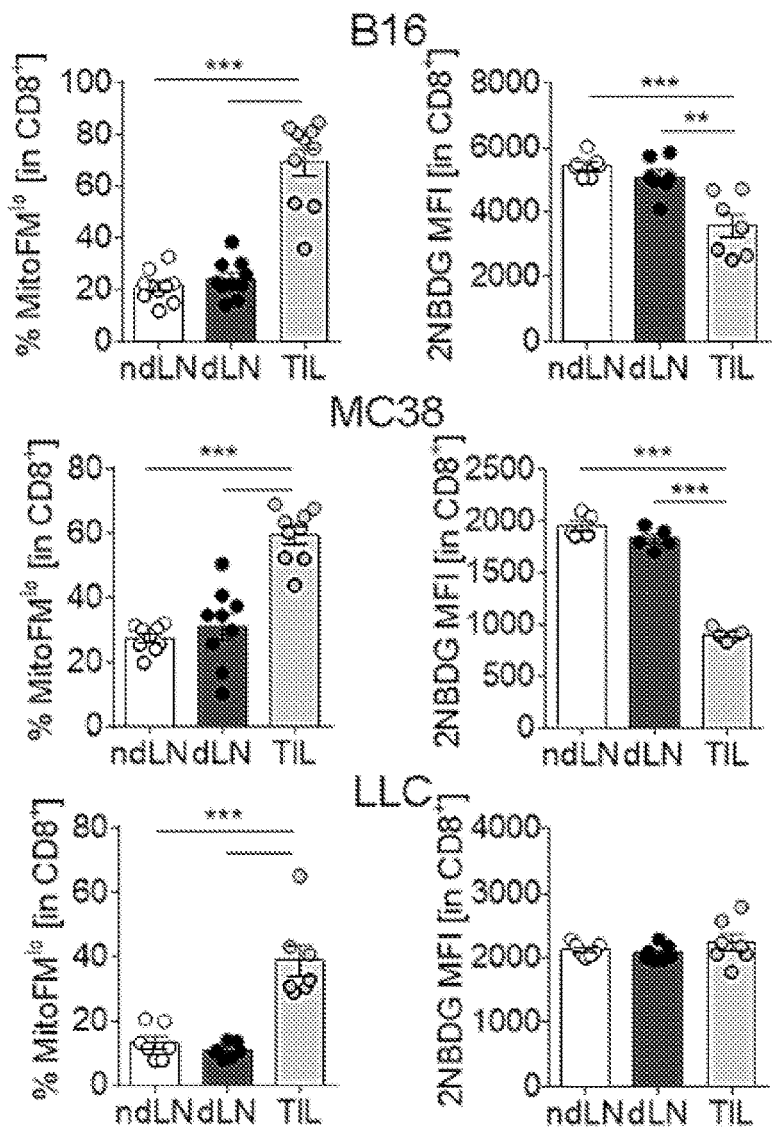
Figure 2D:
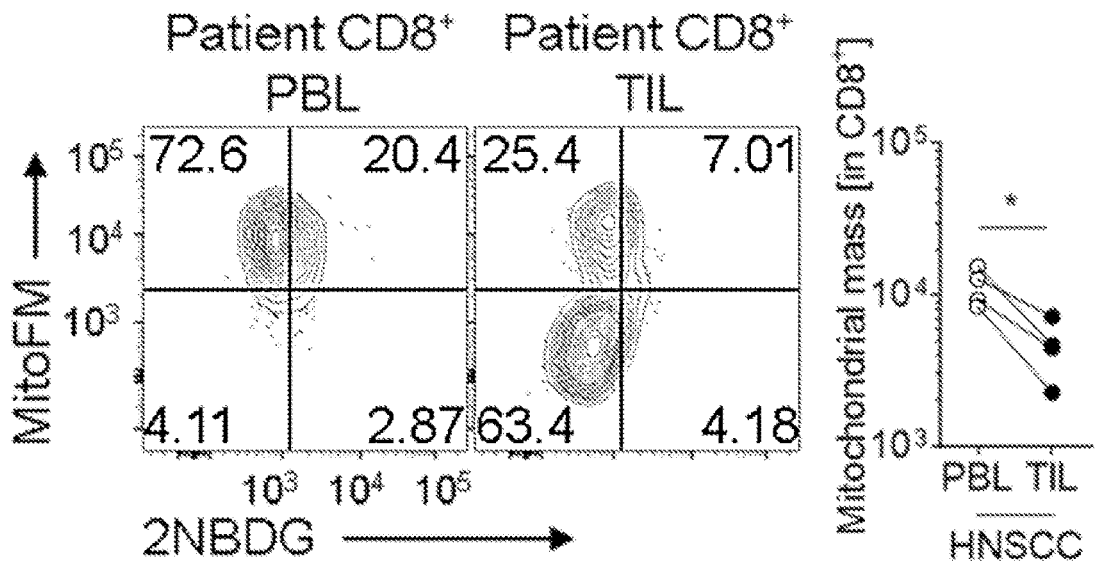

C57/BL6 mice were inoculated with B16 melanoma, and at day 12 (the height of the antitumor immune response), lymph node and tumor preparations were pulsed with 2-NBDG and stained for flow cytometric analysis. While T cells in the lymph nodes, both non-draining (ndLN) and tumor draining (dLN), effectively take up glucose and have relatively high MitoTracker FM staining, CD8$^+$ T cells tumor infiltrating lymphocytes (TIL) show a dramatic reduction of mitochondrial mass as well as the ability to take up glucose (FIGS. 2A, 2B). To confirm the phenotype observed was due to loss of mitochondrial mass and not only mitochondrial depolarization, we observed similar losses employing both MitoTracker Green FM staining (another carbocyanine-based dye) and antibodies to the mitochondrial outer membrane protein Voltage Dependent Anion Channel (VDAC) (FIG. 1B). T cells of various effector and memory phenotypes have been shown to have distinct mitochondrial masses (van der Windt et al., 2013), which was confirmed with dyes; however, these differences are substantially less compared to those observed within the tumor microenvironment (FIG. 1C). For clarity, throughout this study, we primarily gate solely on CD8$^+$ T cells and without further subdivision unless explicitly stated. This response was largely specific to CD8$^+$ T cells, as CD4$^+$ T cells retain most of their mitochondrial mass in B16 tumors. This phenotype was common to three different implantable tumor models inoculated into B6 mice, including MC38 and LLC, although with some notable differences. Mitochondrial mass loss was observed in a proportion of CD4$^+$ T cells in LLC, and no significant differences in glucose uptake was observed (FIG. 2B and FIGS. 1D and 1E). This loss of mitochondrial mass was confirmed by transmission electron microscopy, which revealed that tumor-infiltrating CD8$^+$ T cells not only show lower mitochondrial mass, but also abnormal mitochondrial morphology (FIG. 2C). The metabolic status of T cells infiltrating human head and neck squamous cell carcinoma (HNSCC) was examined, and a similar loss of mitochondrial staining when compared to peripheral blood T cells was observed (FIG. 2D).

Figure 2E:
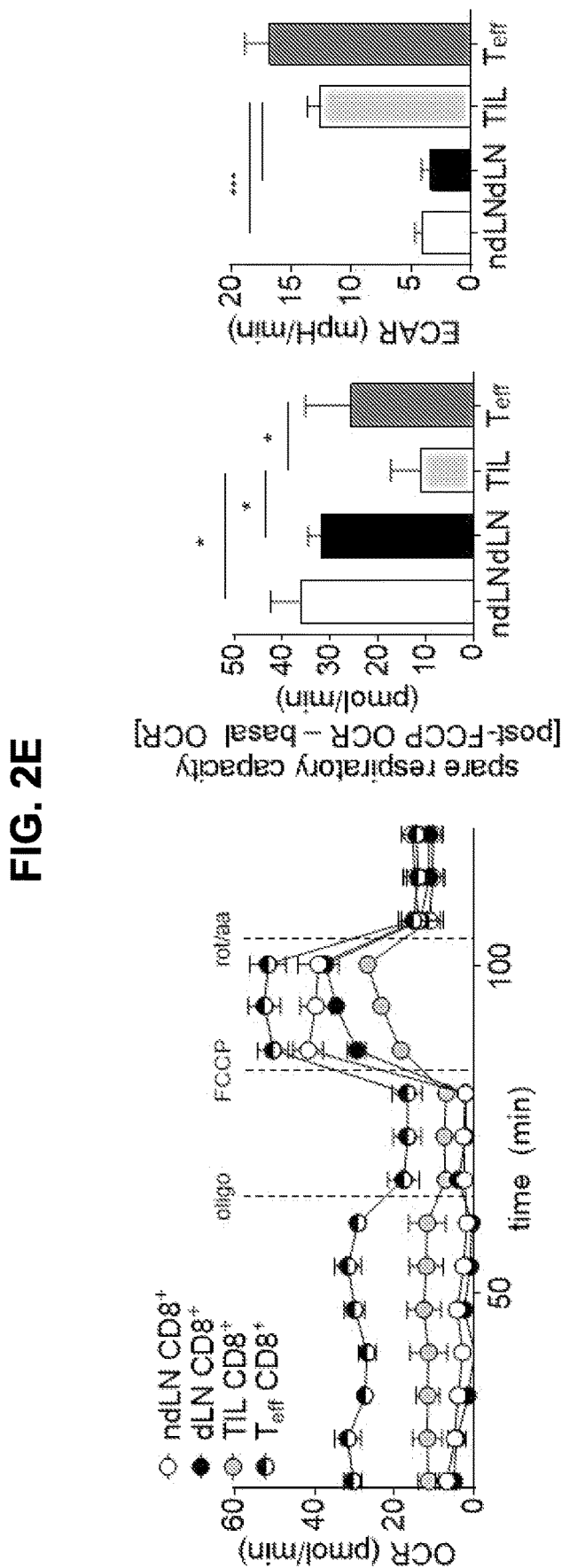

The metabolic output of tumor-infiltrating T cells was examined using a Seahorse extracellular flux analyzer. Metabolic flux analysis of effector, LN-resident, or tumor-infiltrating CD8$^+$ T cells confirmed a persistent defect in oxidative phosphorylation, with significant loss of spare respiratory capacity (a measure of mitochondrial reserve, measured as the difference between basal and uncoupled maximal oxygen consumption) compared to naïve, LN-resident cells or previously activated effector T cells (FIG. 2E). This results in an increased dependence on glycolytic metabolism, as evidenced by increased extracellular acidification rate (FIG. 2E). Thus, T cells infiltrating mouse and human tumors show a dramatic loss of mitochondrial mass and dependence of glycolytic metabolism, rendering them unable to carry out critical cellular functions in the glucose-poor tumor microenvironment.

Example 3

Loss of Mitochondrial Function is Specific T Cell Responses in the Tumor Microenvironment To determine whether this mitochondrial dysfunction was specific to the anti-tumor response or if it occurred in other types of robust effector responses, an adoptive transfer system of naïve, congenically mismatched OT-I T cells into mice bearing OVA-expressing B16 tumors or mice infected with OVA-expressing Vaccinia virus (VV$^{OVA}$) for 6 days was utilized. This experiment compared the chronic activation seen in cancer to a robust, acute in vivo response in which antigen is effectively cleared (Pollizzi et al., 2015).

Figure 3A:
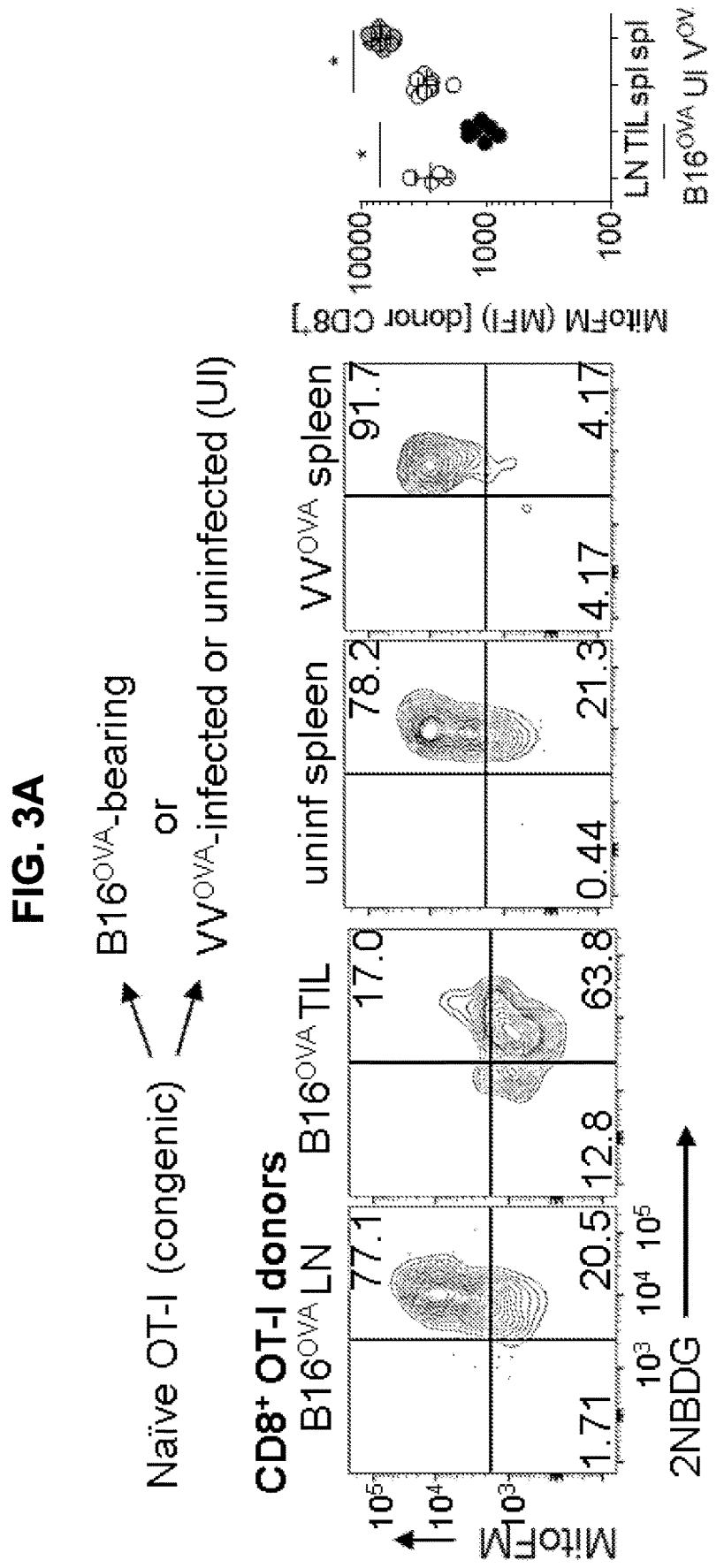

Consistent with the data generated in polyclonal populations from mouse and human tumors, OT-I T cells infiltrating tumors showed dramatically decreased MitoTracker FM staining relative to their LN-resident counterparts (FIGS. 3A, 3B). In stark contrast, OT-I T cells responding in the spleen to VV$^{OVA}$ infection had increased mitochondrial mass compared to splenic OT-I T cells adoptively transferred into mock infected mice, as evidenced by increased MitoTracker FM and intracellular VDAC staining (FIGS. 3A, 4A). T cells responding to OVA in the context of VV$^{OVA}$ also increased basal OXPHOS and spare respiratory capacity (FIG. 3B). VV$^{OVA}$-responsive T cells also displayed heightened glycolytic function, even compared to OT-I T cells isolated from tumors (FIG. 3B). Comparisons of ATP reserves from OT-I T cells responding in B16$^{OVA}$ tumors compared to VV$^{OVA}$-infected spleens revealed TIL show an inability to maintain ATP reserves, while this pool is dramatically increase in cells responding to viral infection (FIG. 3C). Functionally led to differential patterns of cytokine production upon peptide or PMA/ionomycin restimulation (FIG. 4B). Importantly the phenotype of mitochondrial insufficiency observed in tumor-infiltrating lymphocytes was quite stable; OT-I T cells isolated from B16$^{OVA}$ tumors retained a phenotype of low mitochondrial mass, even when isolated and transferred into a new, VV$^{OVA}$ infected mouse for 7 days (FIG. 3D). Thus, T cell dysfunction associated with loss of mitochondria occurs specifically within the chronic activation and microenvironment of cancer.

Example 4

Mitochondria are Depolarized as T Cells Respond in the Tumor Microenvironment

Figure 5C:
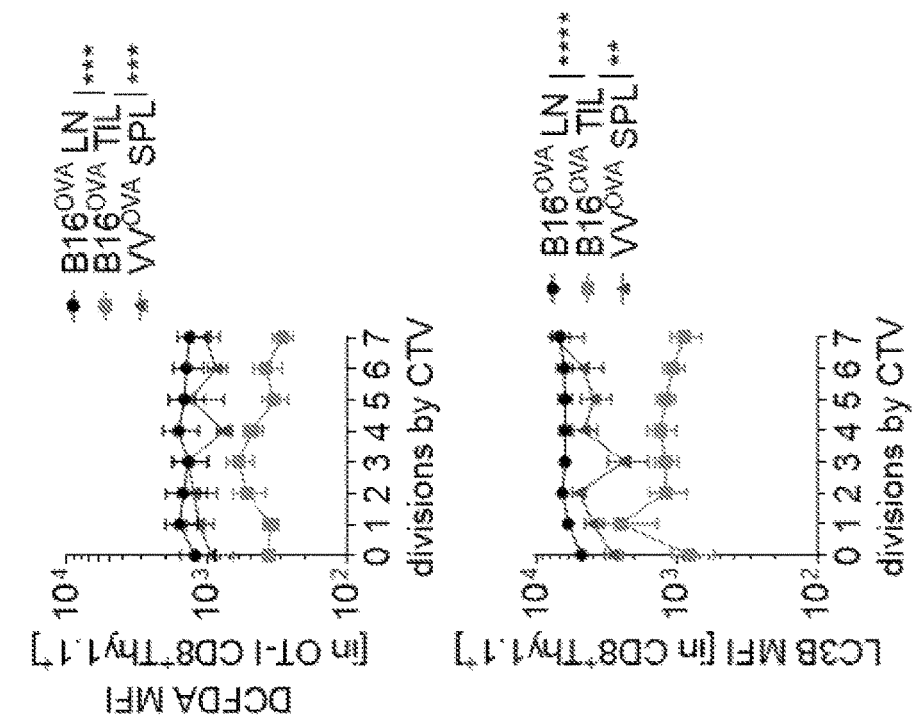

This adoptive transfer model was used to explore the metabolic consequences of activated T cells as they enter the tumor microenvironment versus responding to acute infection. Naïve. OT-I Thy1.1$^+$ T cells were labeled with CellTrace Violet to monitor their proliferation and then transferred into B16$^{OVA}$-bearing or VV$_{OVA}$-infected C57/BL6 (Thy1.2$^+$) mice for 72 h. This resulted in robust proliferation in both scenarios, with OT-I T cells undergoing as many as seven cell divisions during this time (FIG. 5A). Loss of mitochondrial mass was observed as T cells enter the tumor microenvironment, as observed with longer incubations (6 days, FIG. 3A). Experiments employing DCFDA, a ROS indicator, and TMRE, a mitochondrial membrane potential-sensitive dye (FIG. 1A), indicate that T cells responding to antigen in the tumor microenvironment show mitochondrial depolarization as well as a loss of ROS production (FIGS. 5B, 5C).

Figure 5D:
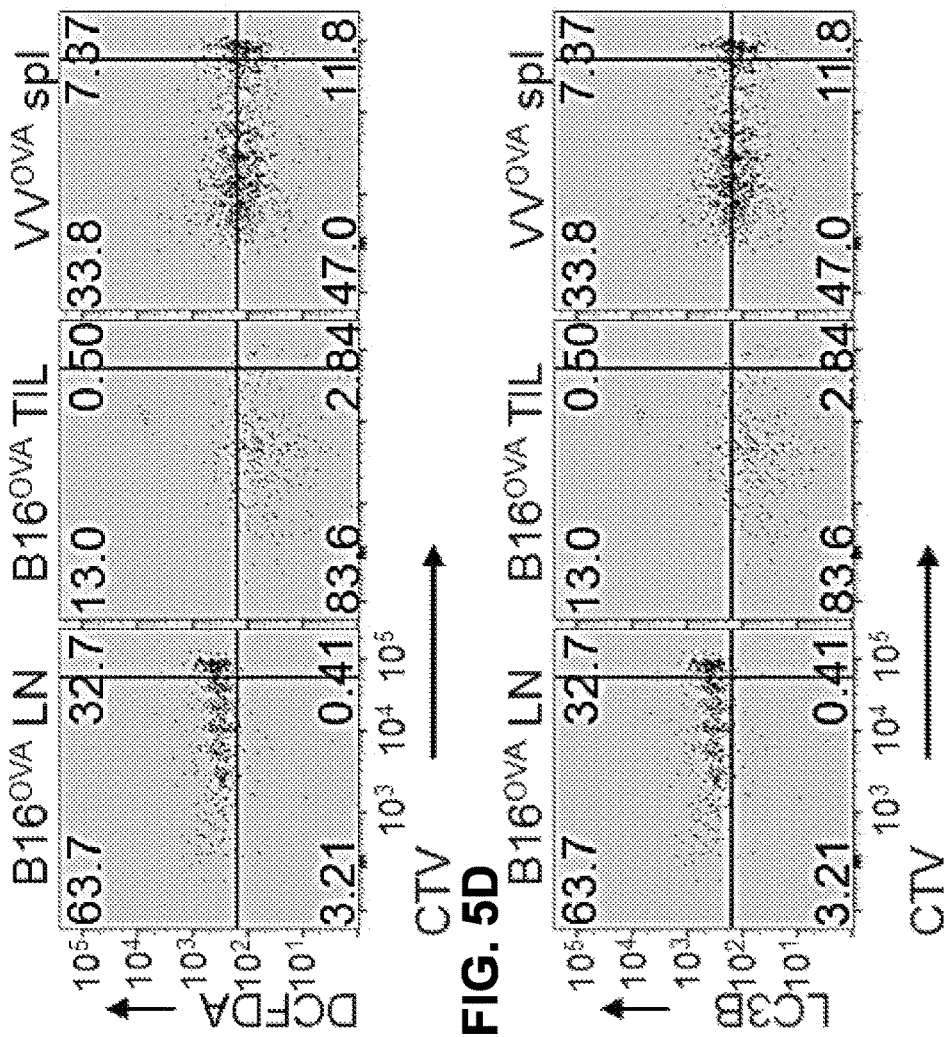
Figure 5E:
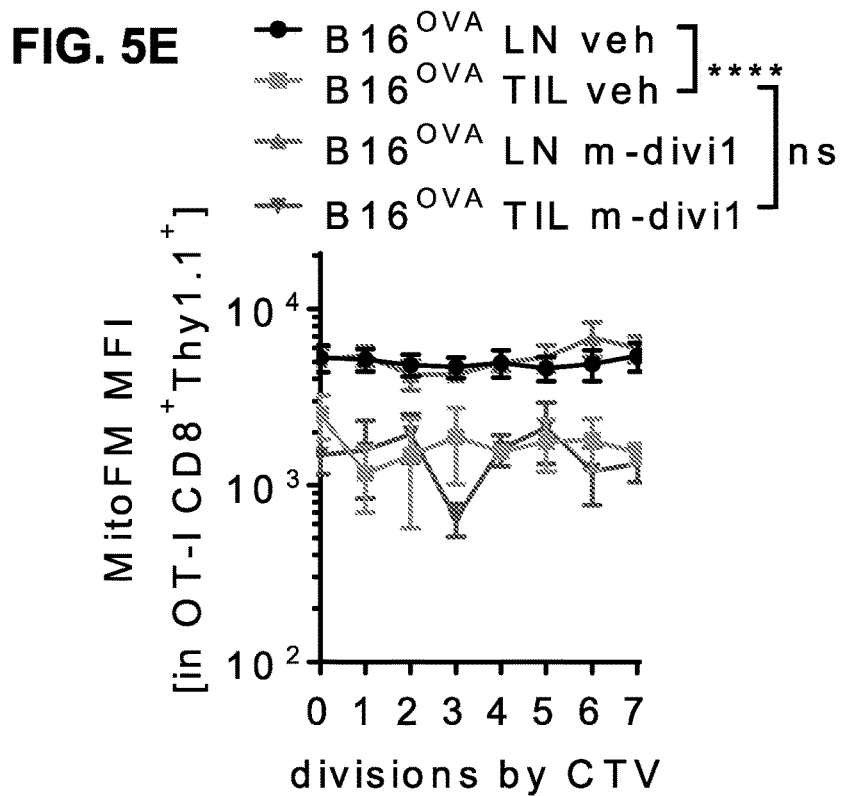
Figure 6B:
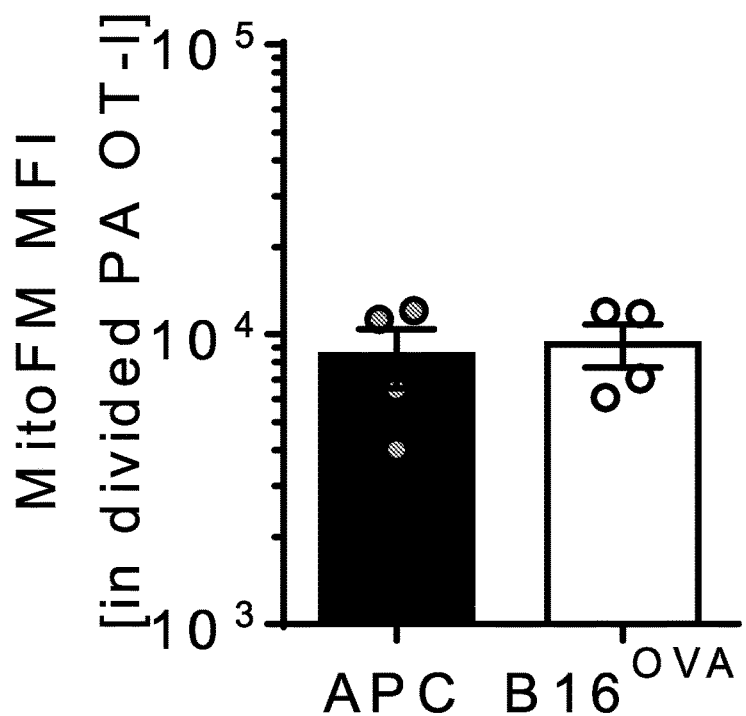
FIGS. 6A-6B. OT-I T cells do not lose mitochondrial activity when activated by tumor cells in vitro. (A) Flow cytogram and tabulated data of CTV-labeled OT-I splenocytes cocultured with either 25 ng/mL SIINFEKL peptide or in a 1:4 ratio with B16$^{OVA}$ cells, seeded 8 h prior to coculture, in the presence of 10 U/mL IL-2. (B) As in A, but using previously activated, purified effector OT-I T cells. Results represent the mean of 3 (of 8) independent experiments. Error bars indicate s.e.m.
Figure 6A:
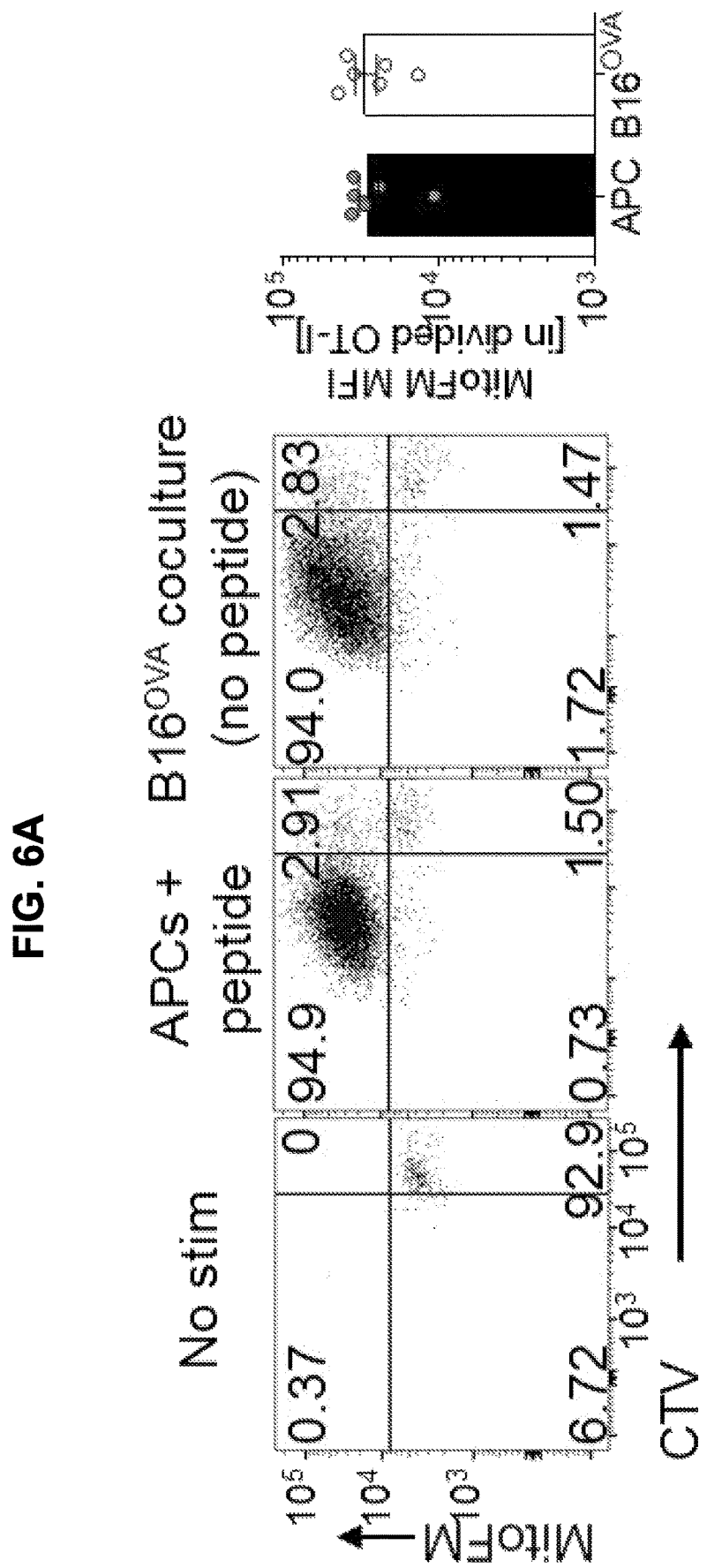

As mitochondrial depolarization can lead to autophagy, it was determined whether mitophagy may be mediating the loss of mitochondria in tumor-infiltrating T cells. No significant increases were observed in LC3b staining in permeabilized OT-I T cells, suggesting that autophagic processes are likely not overtly deregulated in these cells (FIG. 5D). Tumor-bearing mice were treated 24 h after adoptive transfer with the mitophagy and mitochondrial fission inhibitor m-divi-1 (Cui et al., 2010); this also failed to improve mitochondrial staining in tumor infiltrating T cells (FIG. 5E). It was observed that response of naïve or previously activated OT-I T cells to B16$^{OVa}$ tumor cells in vitro did not result in mitochondrial mass loss (FIGS. 6A, 6B).

Thus, T cells responding to cancer lose oxidative metabolism relatively rapidly, but this requires signals that are present specifically in the tumor microenvironment.

Example 5

Figure 7C:
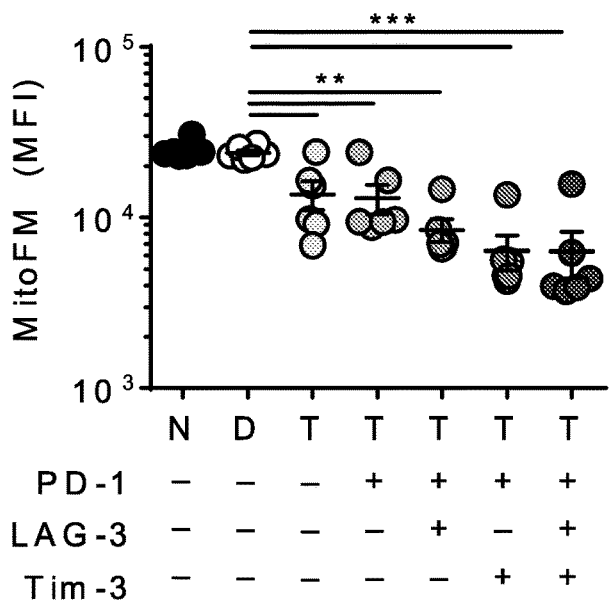
Figure 7D:
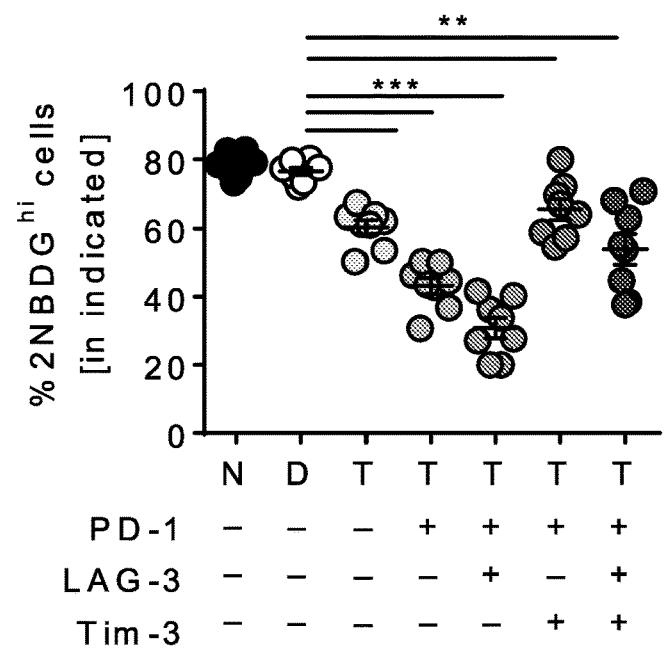
Figure 7E:
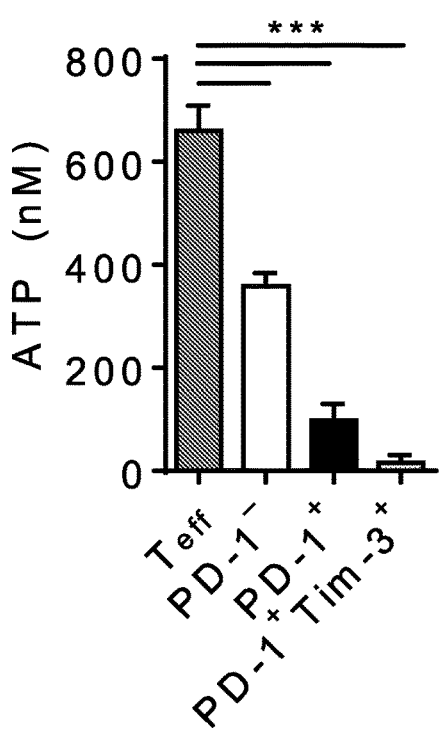
Figure 8A:
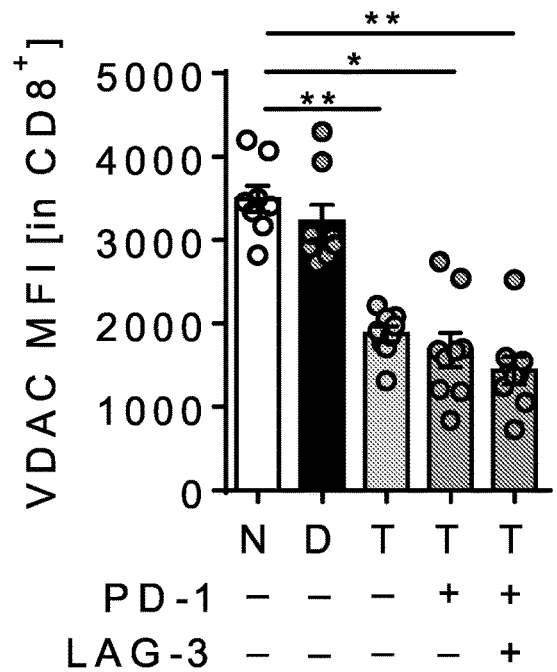
FIGS. 8A-8D. Mitochondrial mass loss is a characteristic of exhausted T cells. (A) VDAC staining of LN or TIL CD8+ T cells from B16-bearing mice expressing co-inhibitory molecules PD-1 and LAG-3. (B) Co-inhibitory molecule expression on CD8+ and CD4+ T cells that are LN-resident or infiltrating MC38 or (C) LLC tumors on day 18 post inoculation (7-10 mm diameter tumors). (D) CD8+ T cells were sorted flow cytometrically from B16-bearing animals based on MitoFM staining and washed extensively. Cells were then stimulated with anti-CD3/anti-CD28 for 6 h in the presence of a protein transport inhibitor, and then stained intracellularly for cytokines. Results for IFNγ staining are tabulated to the right. Results represent the mean of four independent experiments. Error bars indicate s.e.m.

Loss of Mitochondrial Mass Correlates with Upregulation of Co-Inhibitory Molecules As loss of mitochondrial function was progressive and specific to the tumor microenvironment, the relationship between the loss of mitochondria seen in tumor-infiltrating T cells and the expression of molecular markers for dysfunctional, 'exhausted' T cells was determined. B16 melanoma is highly enriched for dysfunctional T cells expressing high levels of PD-1, LAG-3 and Tim-3 (FIG. 7A). Indeed, mitochondrial loss in the polyclonal T cell response appeared to be progressive, as T cells expressing more co-inhibitory molecules had decreased mitochondrial mass, as evidenced by MitoTracker FM staining as well as staining for VDAC (FIGS. 7B, 7C, and FIG. 8A). While mitochondrial mass was inversely correlated with upregulation of coinhibitory molecules, glucose competency was consistently depressed in tumor-infiltrating T cells and did not specifically correlate with these markers (FIG. 7D), in agreement with previous reports (Chang et al., 2015; Ho et al., 2015). This resulted in a failure to maintain a sufficient reserve of ATP (as measured directly ex vivo) (FIG. 7E).

Figure 8B:
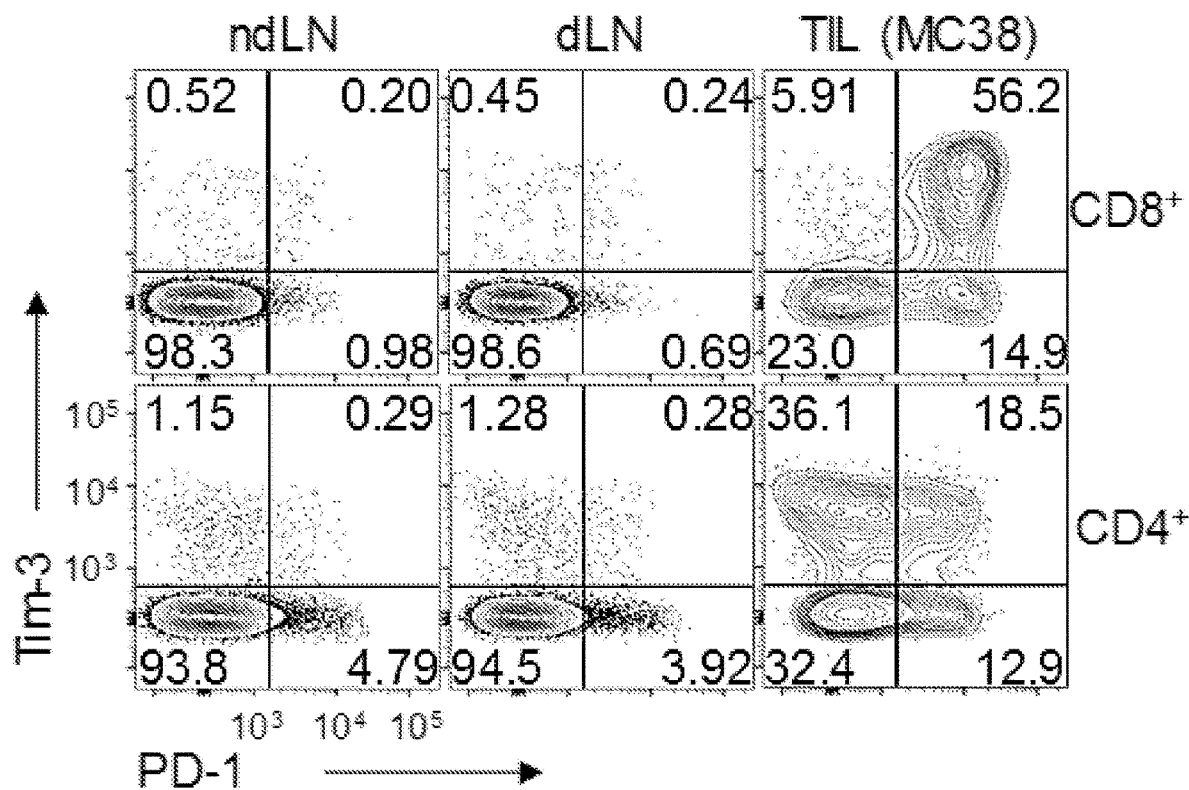
Figure 8C:
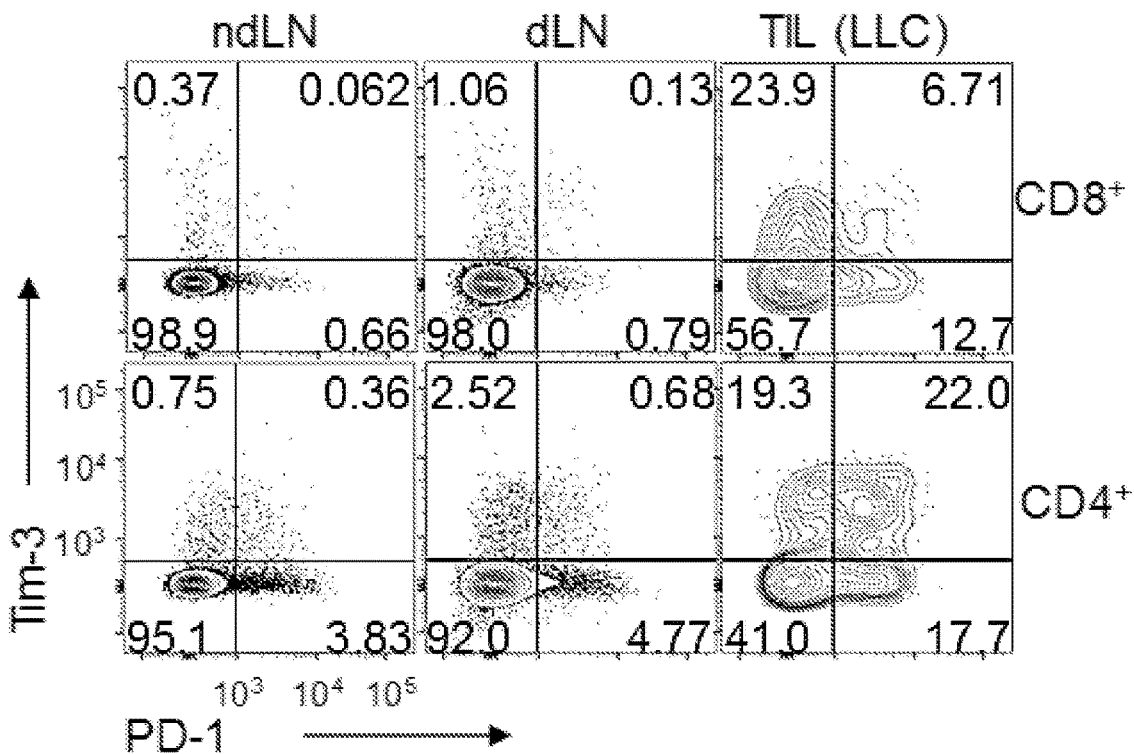
Figure 8C:
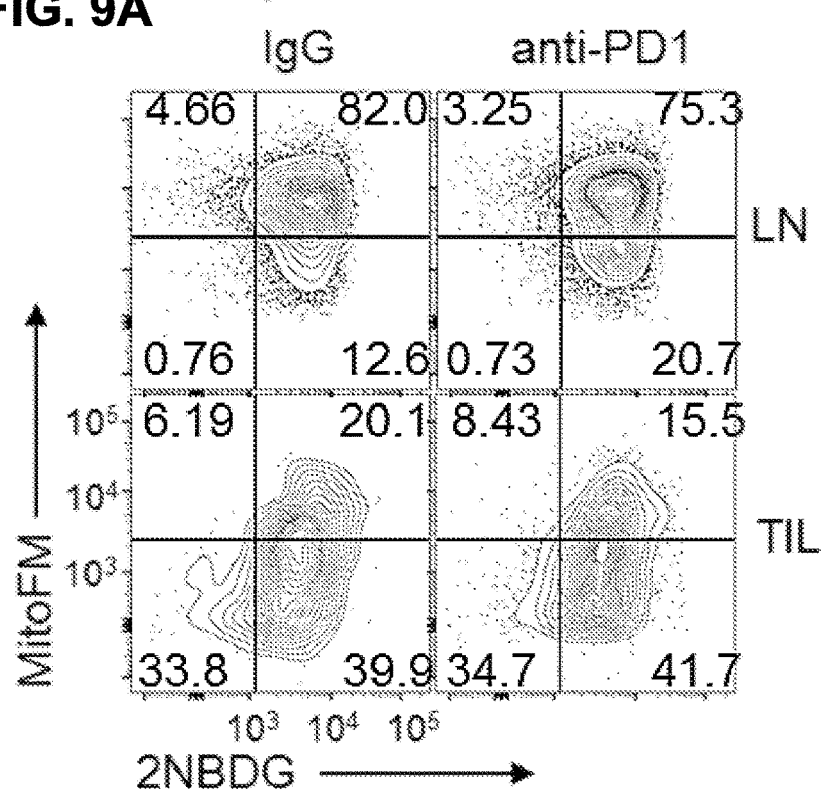

Similar results were observed in MC38 and LLC (FIGS. 8B, 8C). Notably, LLC does not induce similar sustained co-inhibitory molecule expression in CD8$^+$ T cells (compared to the other two models) (FIG. 8C) but still exhibited a significant mitochondrial defect (FIGS. 2B, 1A-1E). CD8$^+$ T cells infiltrating head-and-neck cancers exhibit decreased MitoTracker staining compared to PBL T cells (FIG. 2D) and high levels of coinhibitory molecule expression (FIG. 7F) that correlated with mitochondrial loss (FIG. 7G).

Figure 8D:
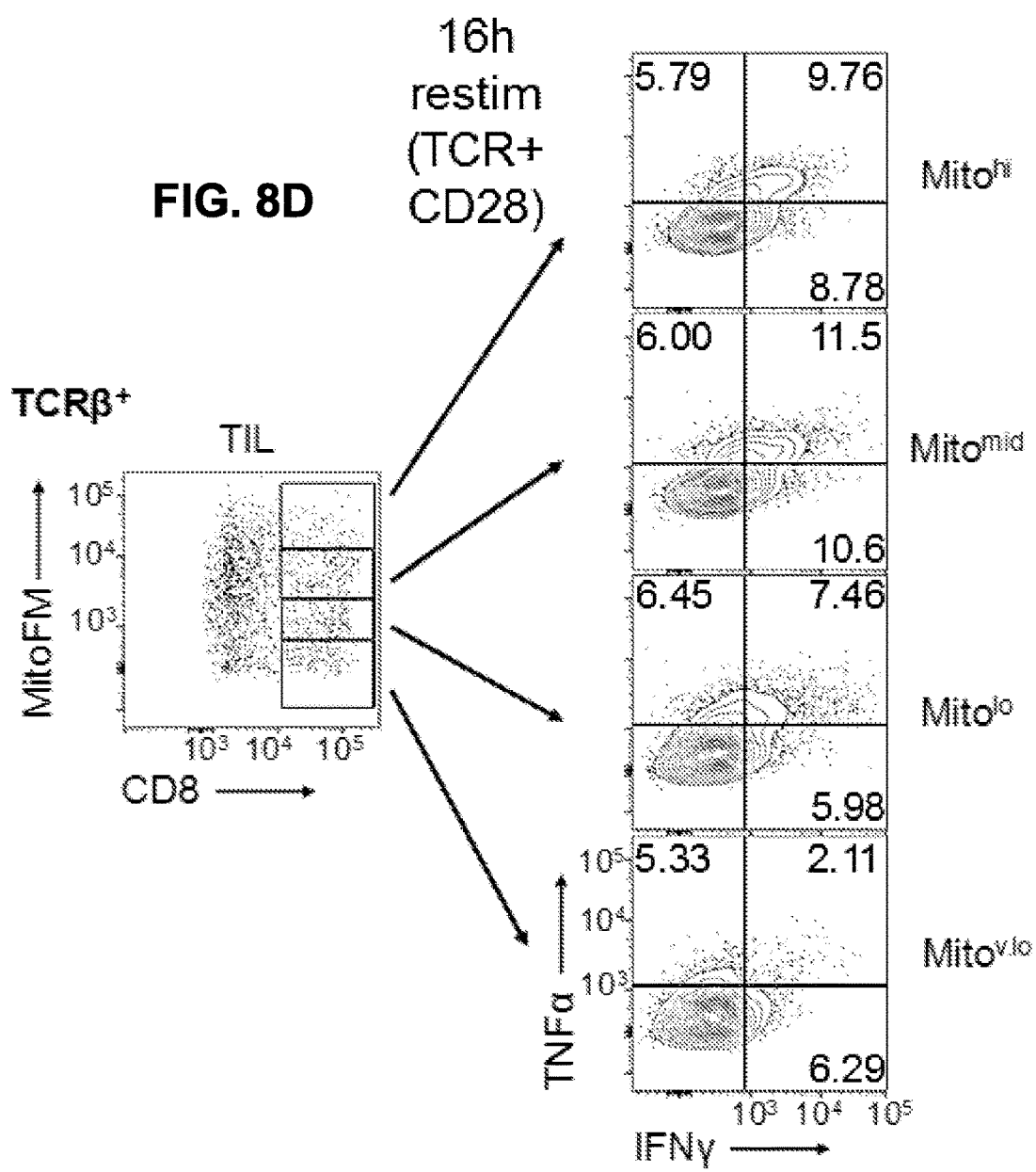
Figure 8D:
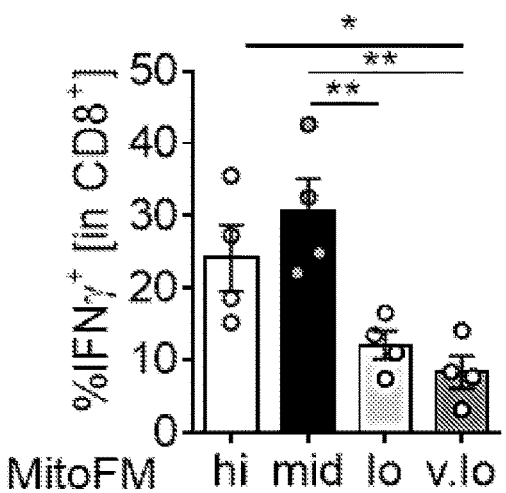

To determine whether, directly, lower MitoTracker FM staining correlated with poor cytokine production, tumor-infiltrating T cells were sorted based on MitoTracker FM staining and then stimulated 16 h to monitor cytokine production. Consistent with their 'exhausted' phenotype, T cells having the lowest mitochondrial staining have the lowest cytokine production (FIG. 8D). Thus, T cells infiltrating solid tumors show a progressive loss of mitochondrial mass and function that appears to be progressive, such that the most 'exhausted' cells show the lowest mitochondrial mass.

Example 6

Figures 9B, 9C:
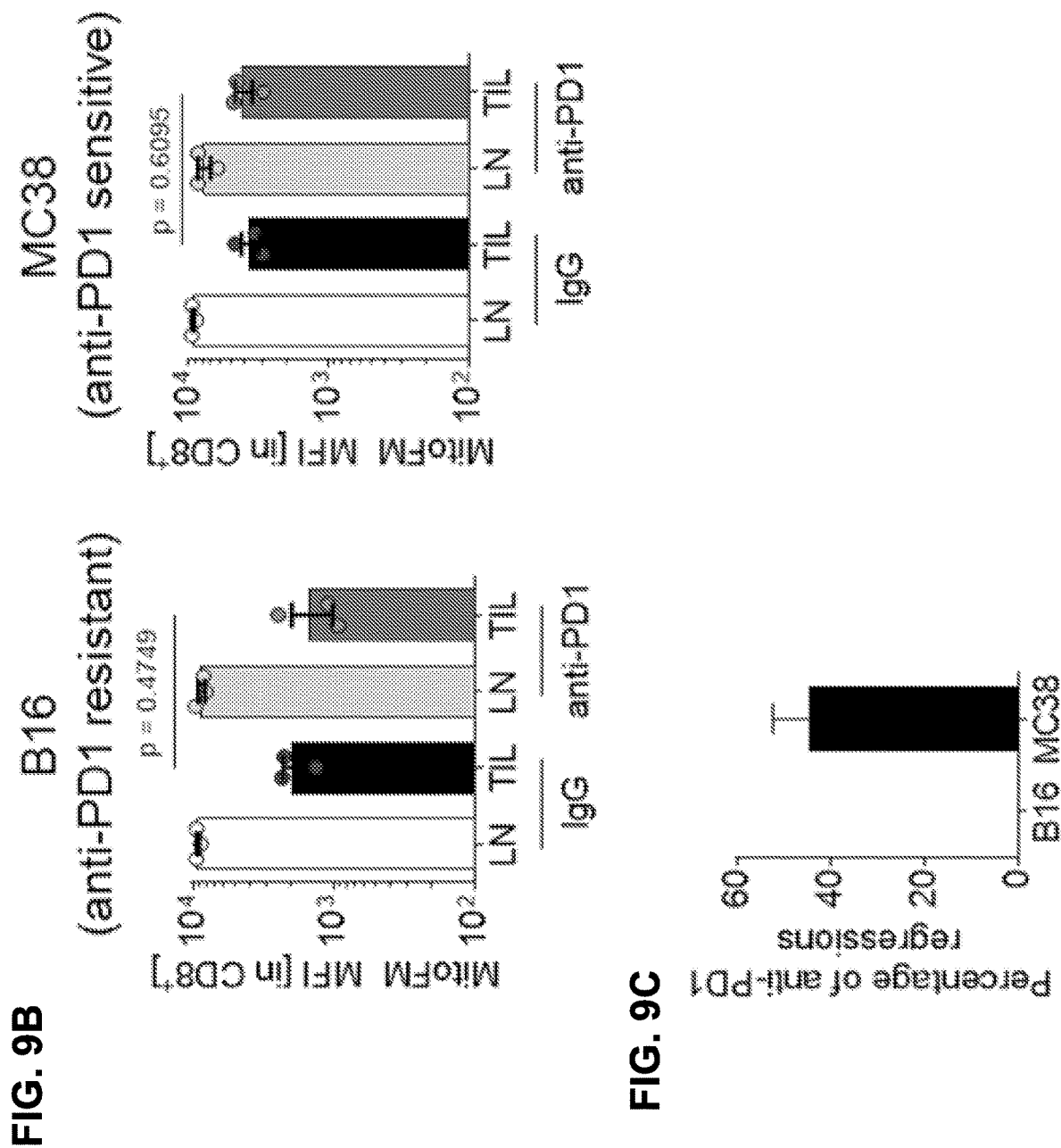

Loss of Oxidative Metabolism in Cancer is Largely Independent of PD-1 Signaling and Regulatory T Cells PD-1 blockade can reverse tumor-induced T cell dysfunction and lead to heightened antitumor immunity and cancer regression (La-Beck et al., 2015). To determine if PD-1 blockade might rescue loss of mitochondrial function in tumor-infiltrating T cells, B16 was used, in which PD-1 therapy is not effective, despite the presence of large numbers of PD-1$^+$ T cells, as well as MC38, which is sensitive to PD-1 monotherapy (Woo et al., 2012). Mice were inoculated with B16 or MC38 tumors and received anti-PD-1 therapy (200 µg, thrice weekly) or its isotype control when palpable tumors were present (1×1 mm). However, regardless of treatment or tumor type, tumor-infiltrating T cells showed similar decreases in mitochondrial mass (FIGS. 9A, 9B). The PD-1 blockade strategy was therapeutically effective, resulting in 40% regression in MC38 bearing mice (FIG. 9C).

Figure 9D:
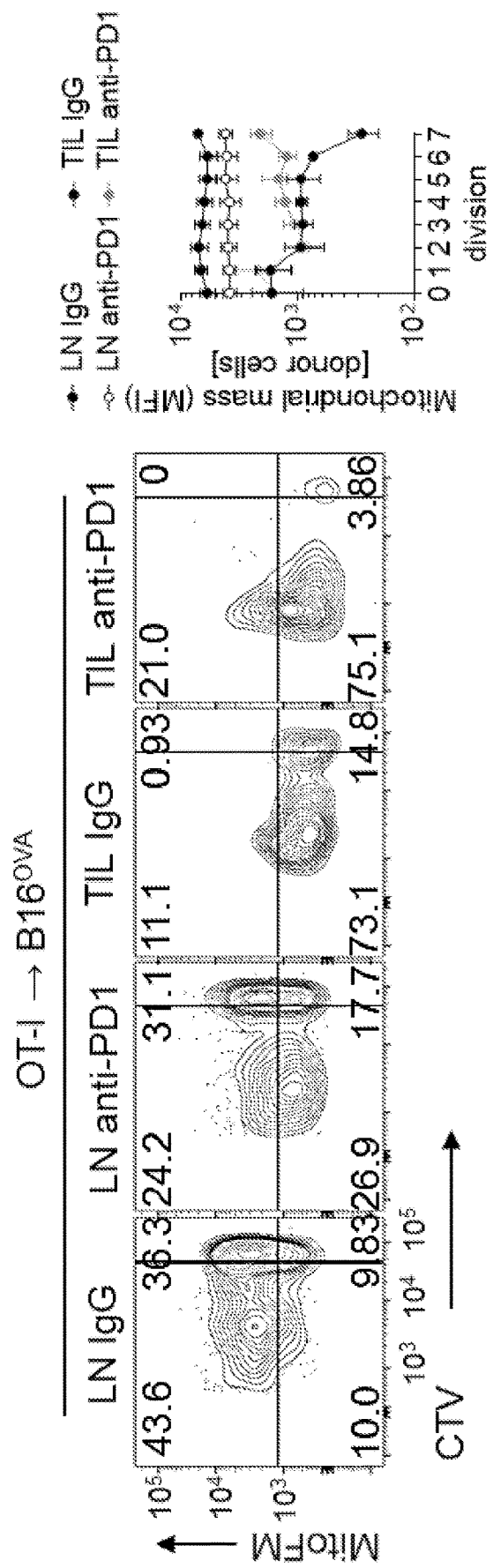

To determine whether PD-1 signaling might impact the mitochondrial sufficiency of recent entrants into the tumor, dye-labeled OT-I T cells were transferred into mice bearing established B16$^{OVA}$ tumors under the cover of PD-1 blockade or its control for 72 h. In this situation, a temporary and incomplete recovery of MitoTracker FM staining in later cell divisions was observed (FIG. 9D). However, these changes were statistically significant only when analyzed as broken down by cell division, and could not be sustained or detected past 72 h. Thus, while PD-1 may play a role in modulation of metabolism, blockade of PD-1 is not sufficient to reverse mitochondrial insufficiency observed in tumor-infiltrating T cells.

Figure 10A:
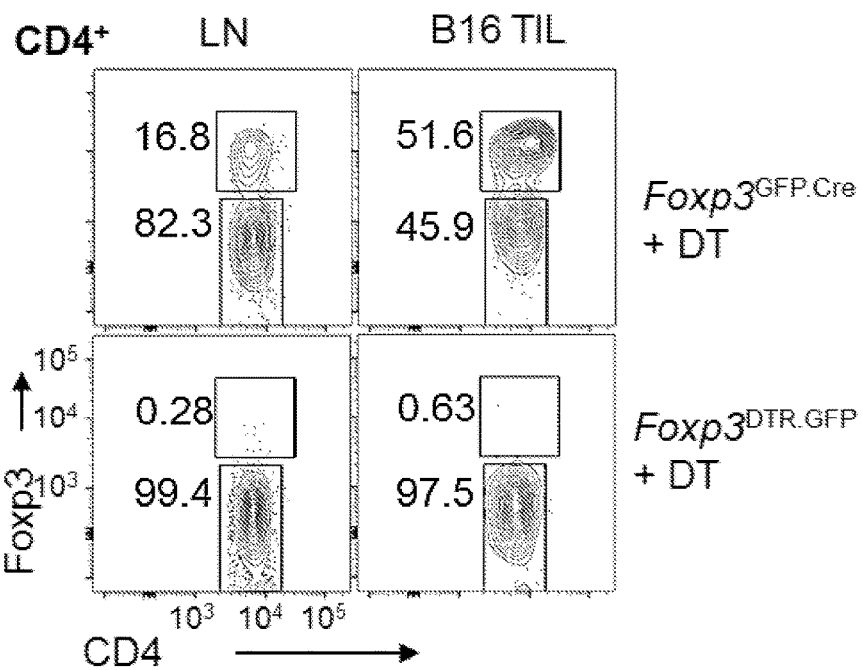
Figure 10B:
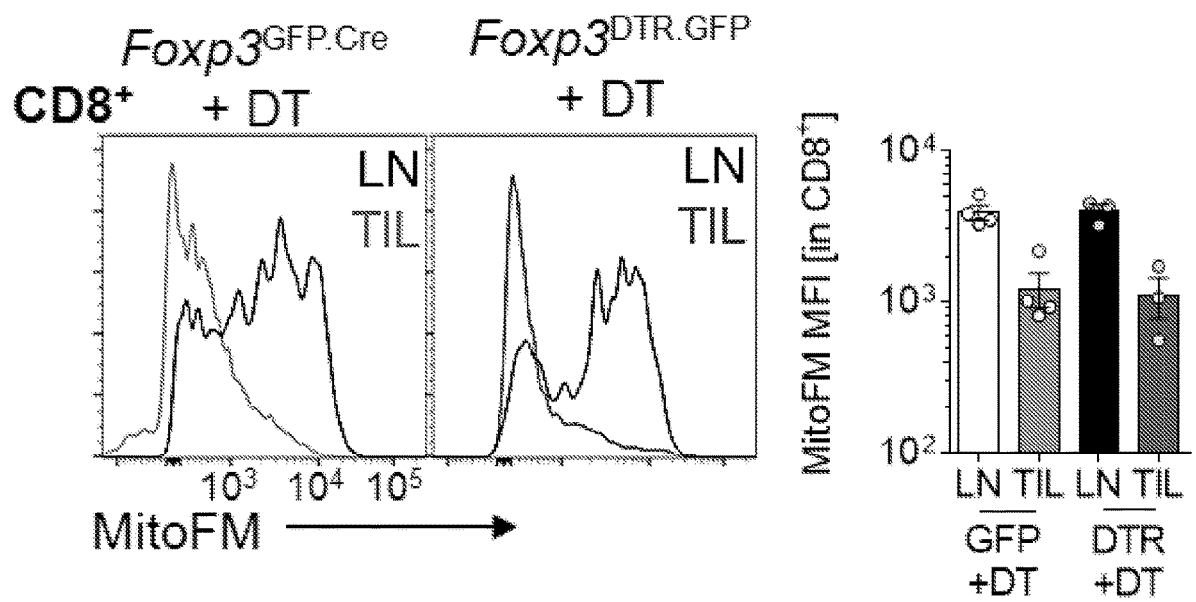

Regulatory T cells also represent a major immunosuppressive player in the tumor microenvironment (Liu et al., 2016). Thus, it was determined whether T$_{reg}$ cells mediate metabolic insufficiency in the tumor microenvironment by examining CD8+ TIL from Foxp3$^{DTR.GFP}$ mice treated with diphtheria toxin (Kim et al., 2007a). This results in near complete depletion of tumor-infiltrating $T_{reg}$ cells (FIG. 10A) but no significant increases in CD8+ T cell MitoTracker FM staining (FIG. 10B). In agreement with these in vivo findings, CD8+ T cells suppressed in vitro by purified $T_{reg}$ cells also maintain mitochondrial sufficiency (FIG. 10C).

Thus, metabolic insufficiency in CD8+ TIL appears to be driven in a manner independent of 'classic' immunosuppressive mechanisms in the tumor microenvironment.

Example 7

Figure 11A:
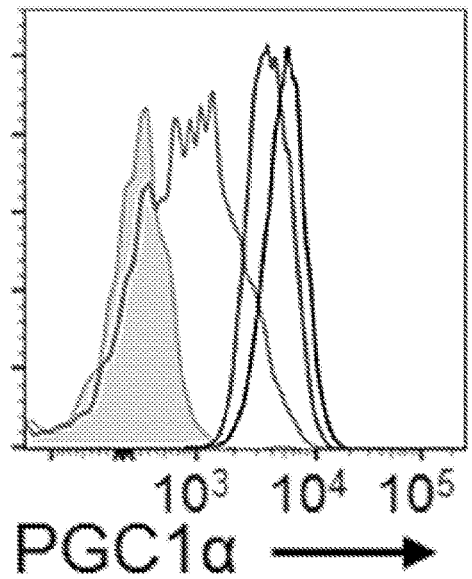
FIGS. 11A-11H. Intratumoral T cell mitochondrial biogenesis is repressed by chronic Akt-mediated repression of PGC1α (A) Flow cytogram (left) and tabulated data (right) of PGC1α intracellular staining in CD8+ T cells isolated from nondraining or draining LNs or TIL preparations from B16 or MC38 bearing mice. Shaded histogram indicates isotype control. (B) Flow cytogram of PGC1α expression in CTV-labeled, naïve OT-I T cells adoptively transferred into B16$^{OVA}$ bearing mice for 72 h. Tabulation for multiple experiments is to the right. (C) Flow cytogram of cytokine production of congenically mismitached WT OT-I T cells transferred into B16$^{OVA}$-bearing or VV$^{OVA}$-infected mice for 96 h, then restimulated with SIINFEKL peptide. (D) Representative and tabulated phospho-Akt (S473) and phospho-Foxo1 (T24)/3a(T32) staining of the indicated cell populations in mice bearing 14-day B16 tumors. MFI is reported. (E) Representative flow cytogram and tabulated data indicating PGC1α staining in pAkt low or high cells. (F) MFI of pAkt staining in naïve OT-I T cells, or OT-I T cells transferred for 3 or 6 days into a B16$^{OVA}$-bearing or VV$^{OVA}$ infected mouse. (G) PGC1α levels and (H) mitochondrial mass of CD8+ T cells from LN and TIL of 14-day B16-bearing mice treated for 60 h with Akt inhibitor VIII or its vehicle. Results are representative of 5 (A,B, D) 3 (C, E, G, H) or 2 (F) independent experiments. *, p<0.05, p<0.01, *p<0.001 by unpaired t-test (A, F, G, H) or paired t-test (D, E, G, H). ***p<0.001 by two-way ANOVA. Error bars indicate s.e.m.
Figure 11A:
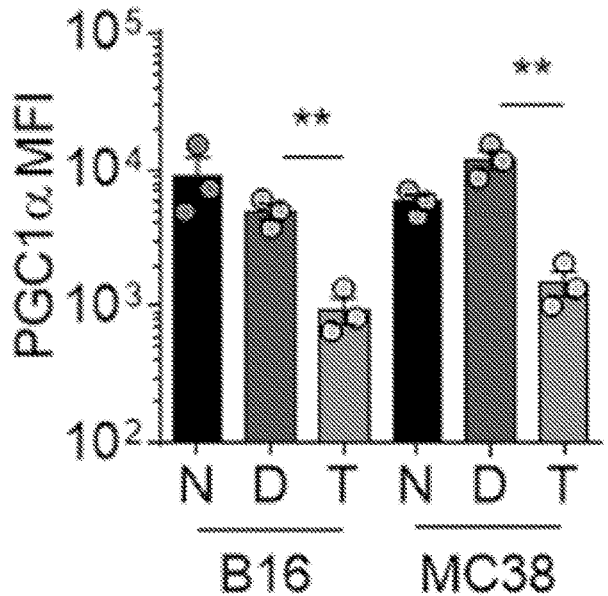
Figure 11B:
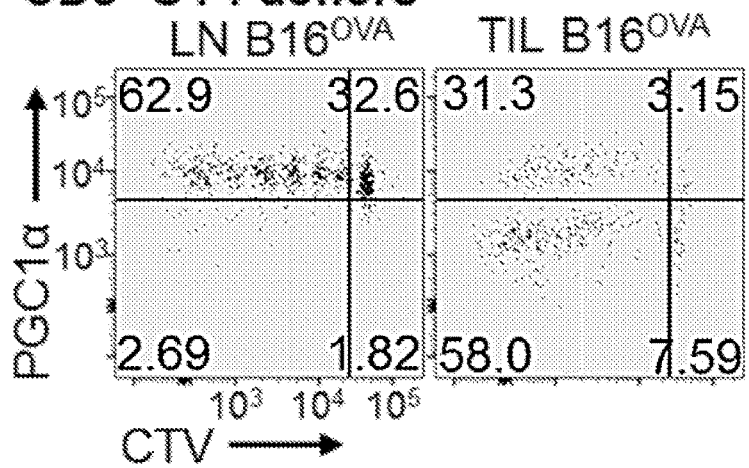
Figure 11B:
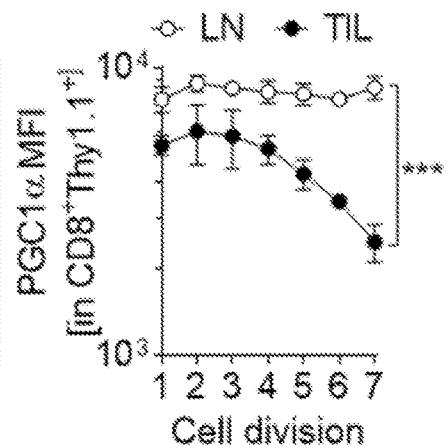
Figure 12A:
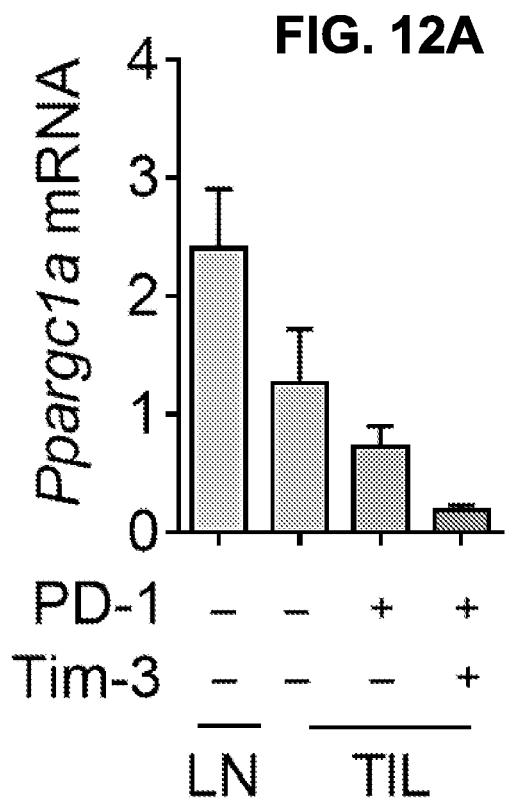
Figure 12B:
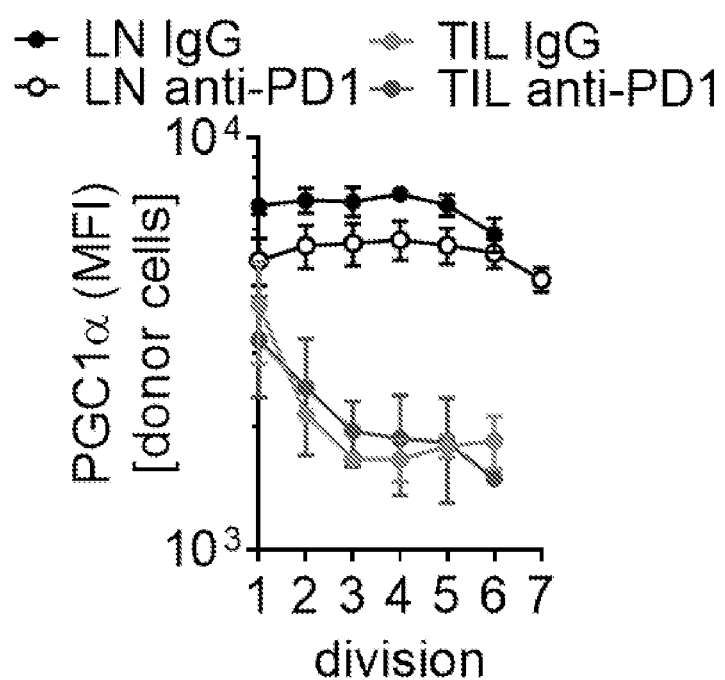

PGC1α-Mediated Mitochondrial Biogenesis is Repressed by Akt in Tumor-Infiltrating T Cells Having found that PD-1 and $T_{reg}$ cells did not appear to outright cause the mitochondrial dysfunction seen in tumor-infiltrating T cells, the molecular mechanism for this metabolic phenotype was determined. Kinetic analyses showed that these T cells divided extremely rapidly in response to tumor antigen in the LNs, so it was hypothesized that T cells failed to properly program mitochondrial biogenesis during rapid cell division upon entry into the tumor microenvironment. Mitochondrial replication is programmed in part by the transcription factor TFAM and regulated by the transcriptional coactivator PGC1α (encoded by Ppargc1a) (Finck and Kelly, 2006; Spiegelman, 2007). Intracellular staining and qPCR analysis revealed that tumor infiltrating CD8+ T cells have dramatically lower levels of PGC1α (FIGS. 11A and 12A). Kinetic analysis of dye labeled, naïve OT-I cells injected into B16$^{OVA}$-bearing mice showed PGC1α downregulation occurred concomitant with cell division specifically in the tumor microenvironment, suggesting microenvironment-derived signals promoted a downregulation of mitochondrial biogenesis during T cell proliferation (FIG. 11B). Repression of PGC1α occurred even in the presence of PD-1 blockade, suggesting that another dominant signal present in the tumor microenvironment suppresses PGC1α expression (FIG. 12B).

Figure 11C:
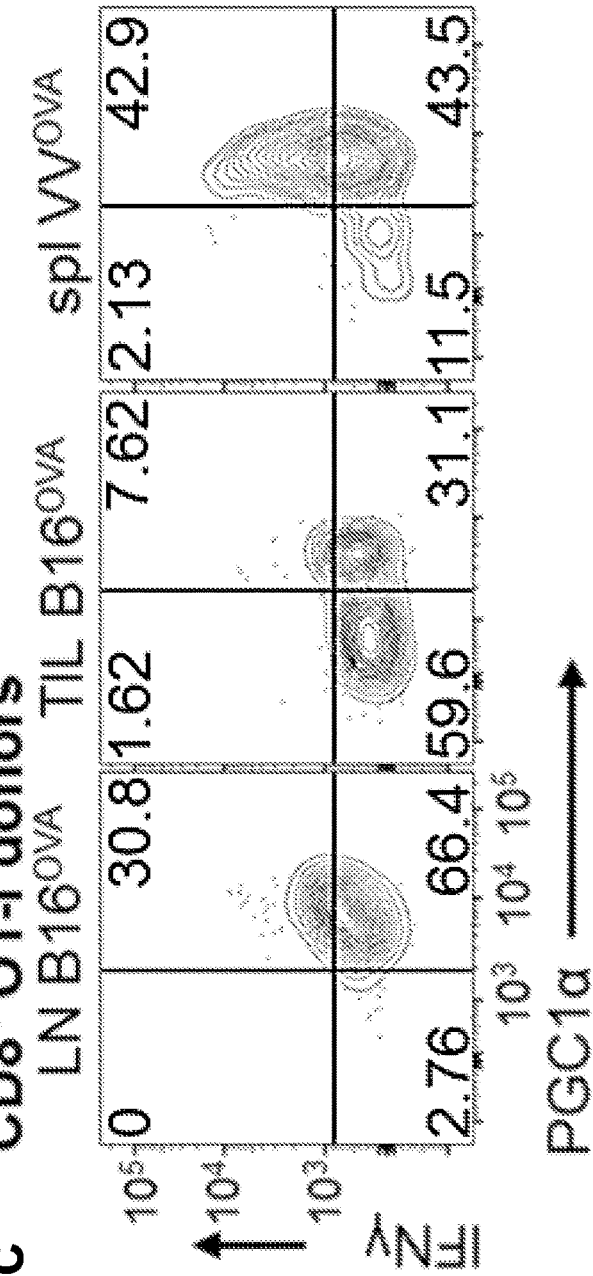
Figure 12C:
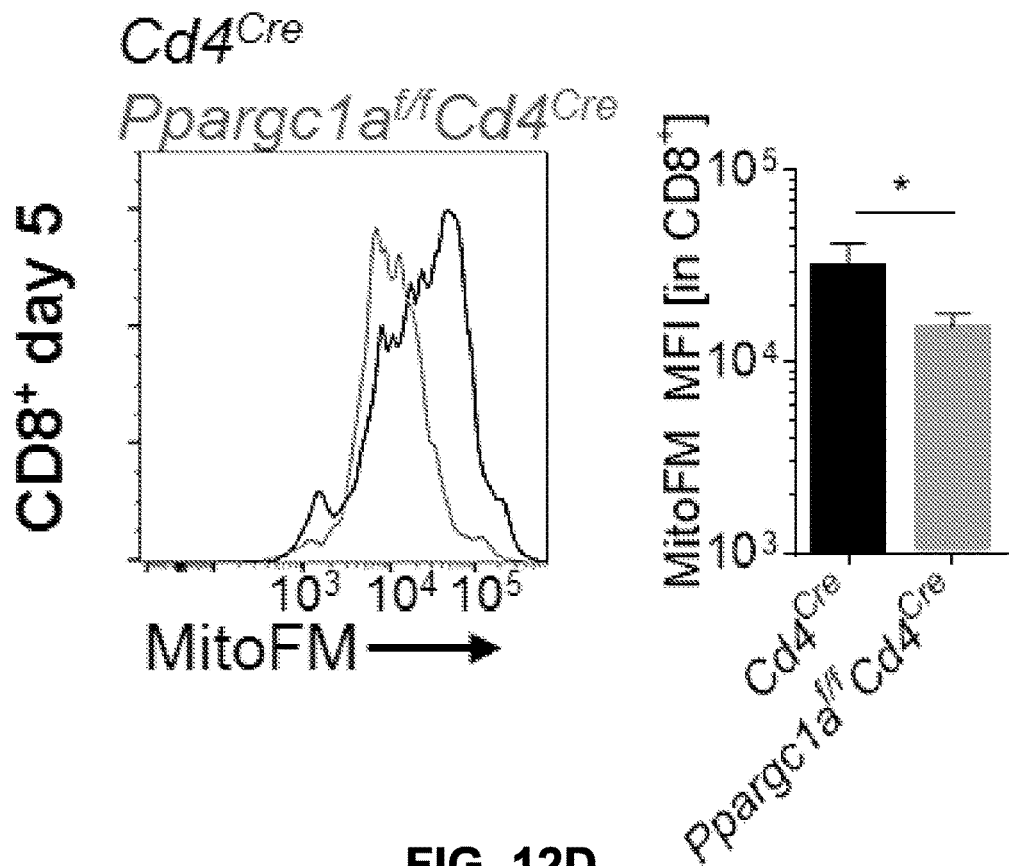
Figure 12D:
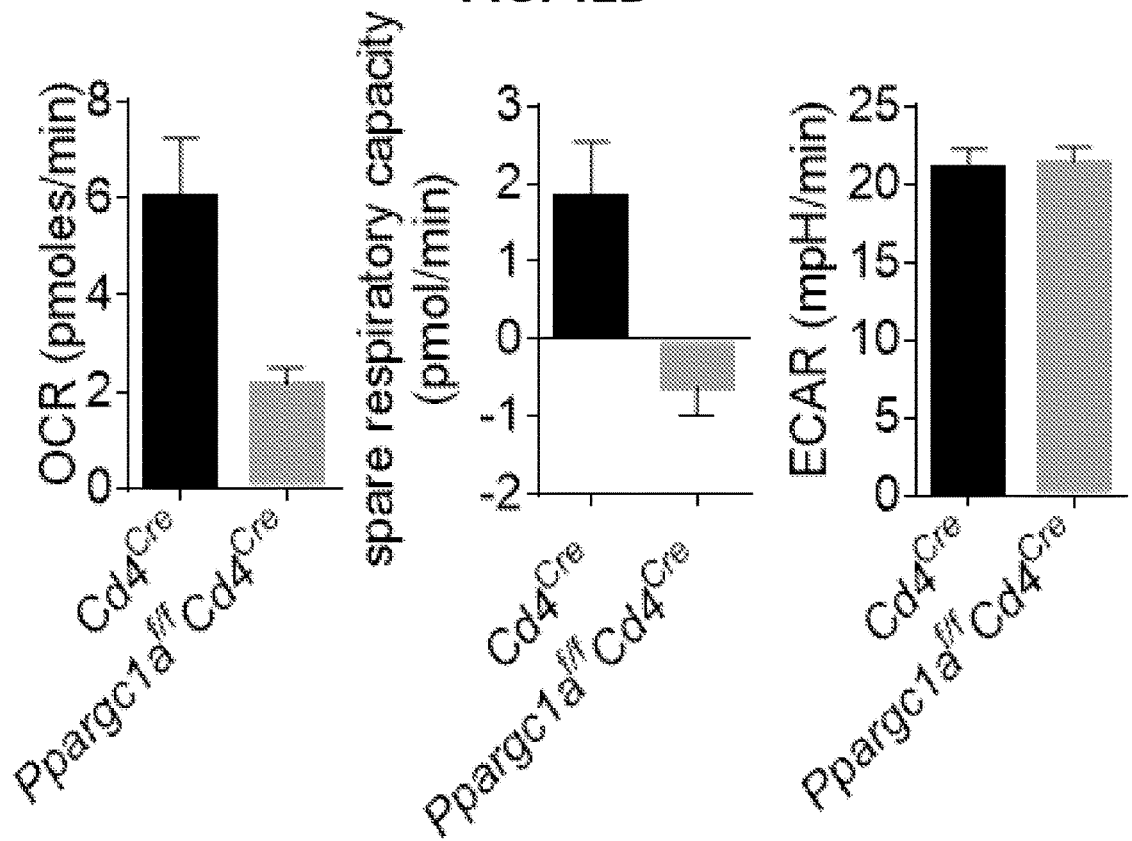
Figure 12E:
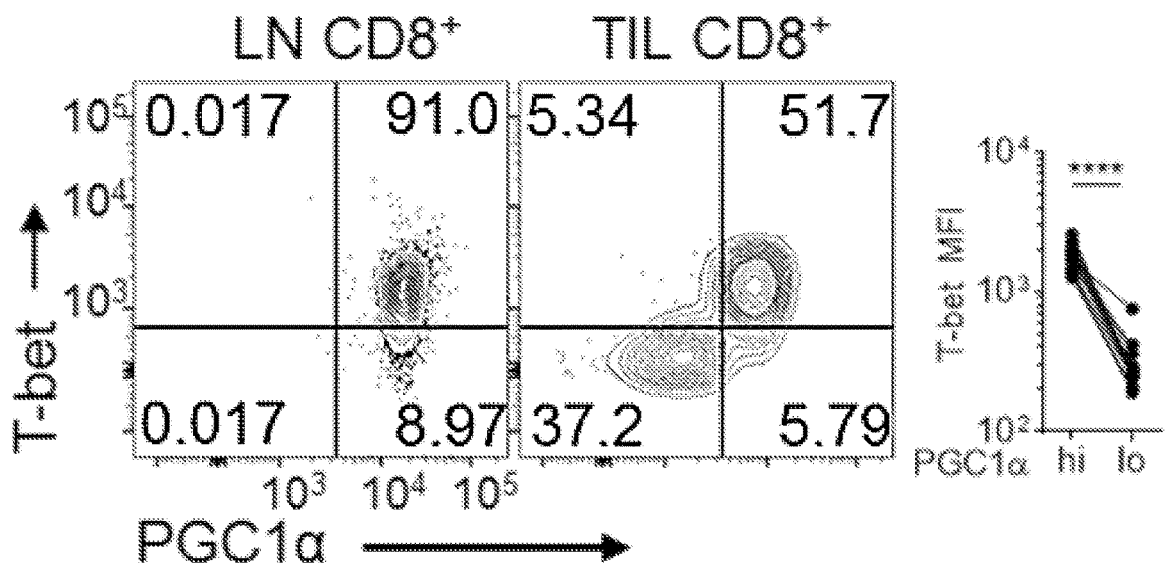
Figure 12F:
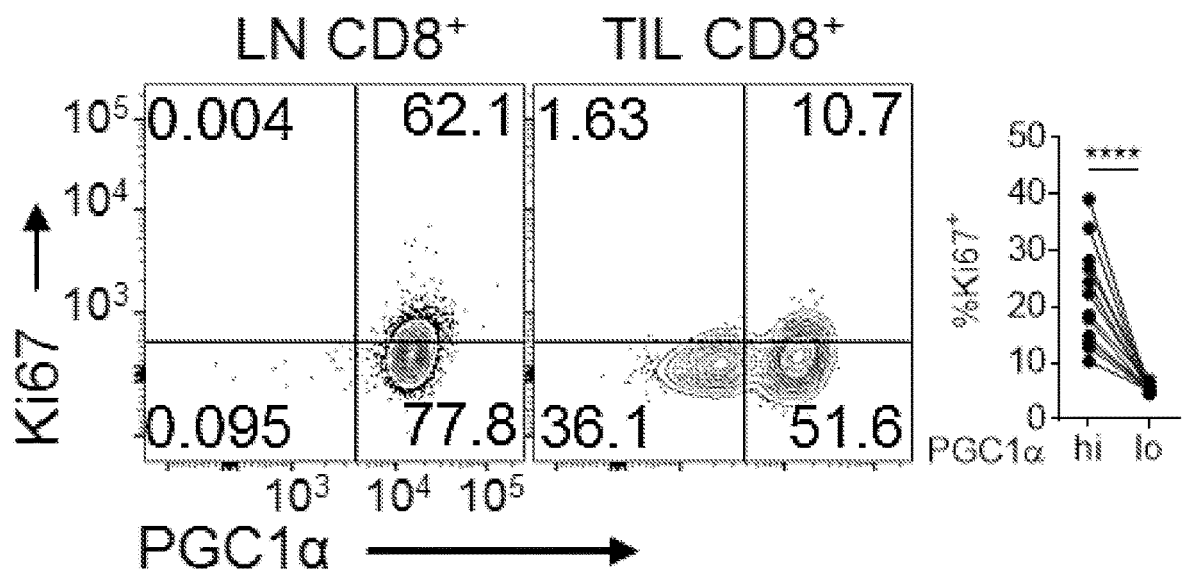

Analysis of PGC1α-deficient T cells (Ppargc1$^{f/f}$Cd4$^{cre}$ mice) revealed progressive losses of mitochondrial mass in vitro after activation, resulting in decreased OCR (FIGS. 12C, 12D). Comparison of cytokine production in LN- and TIL-resident OT-I T cells responding to cognate peptide revealed that the small proportion of PGC1α+ cells in tumor-infiltrating compartments marked the T cells that were competent to produce cytokines, indicating that this pathway is important for intratumoral T cell function (FIG. 11C). In agreement with this observation, T cells showing repressed PGC1α staining also show decreased T-bet and Ki-67 staining, consistent with a model in which PGC1α repression is concomitant with a terminally exhausted phenotype (FIGS. 12E, 12F).

PGC1α is dynamically regulated by a number of signaling pathways relevant to T cell activation, but a prominent repressive pathway is mediated by Akt (Fernandez-Marcos and Auwerx, 2011). Akt has been shown to upregulate glycolytic metabolism through a variety of mechanisms, but it also can actively repressive oxidative programs, particularly through the phosphorylation and consequent inactivation of Foxo family transcription factors, which have been previously shown to promote PGC1α expression (Borniquel et al., 2010; Olmos et al., 2009). Thus, the Akt status of tumor-infiltrating T cells was determined, with the hypothesis that the strong, chronic activation signals mediated by persistent antigen in cancer might promote Akt activation and repress the oxidative phenotype programmed by Foxo.

Figure 11D:
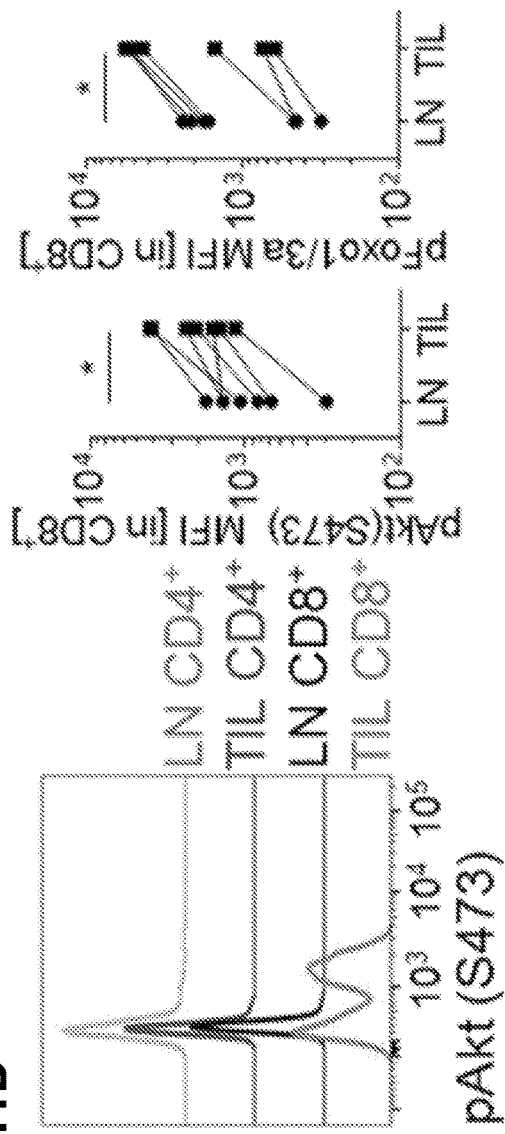

CD8+ T cells infiltrating B16 tumors show increased Akt activation and Akt-mediated inhibitory Foxo phosphorylation compared to LN (where the vast majority of T cells are resting) (FIG. 11D). Comparison of Akt activation to PD-1 status revealed that Akt is highest in tumor-infiltrating T cells that are PD-1$^{mid}$ as well as those expressing very high levels of PD-1 (as well as LAG-3), suggesting that Akt is persistent in newly activated T cells as well as those receiving chronic stimulation and differentiating toward terminal exhaustion (FIG. 12G). Intratumoral cells that have high pAkt are particularly low in PGC1α protein levels (FIG. 11E).

Figure 11F:
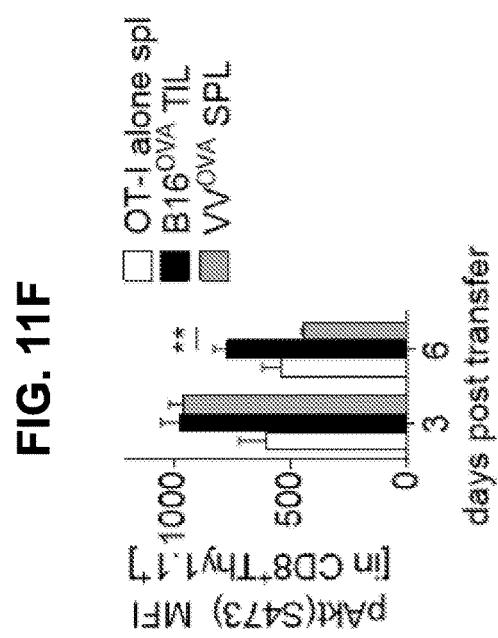
Figure 11E:
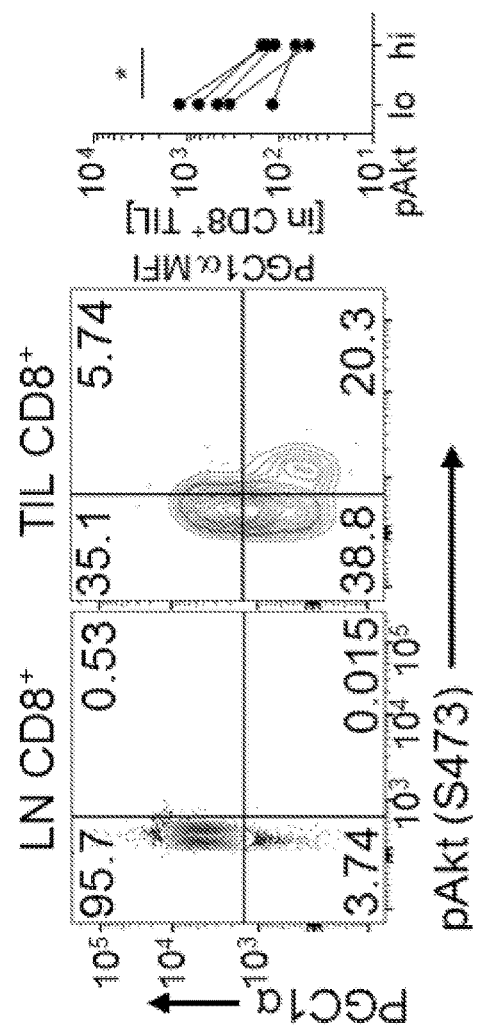
Figure 11G:
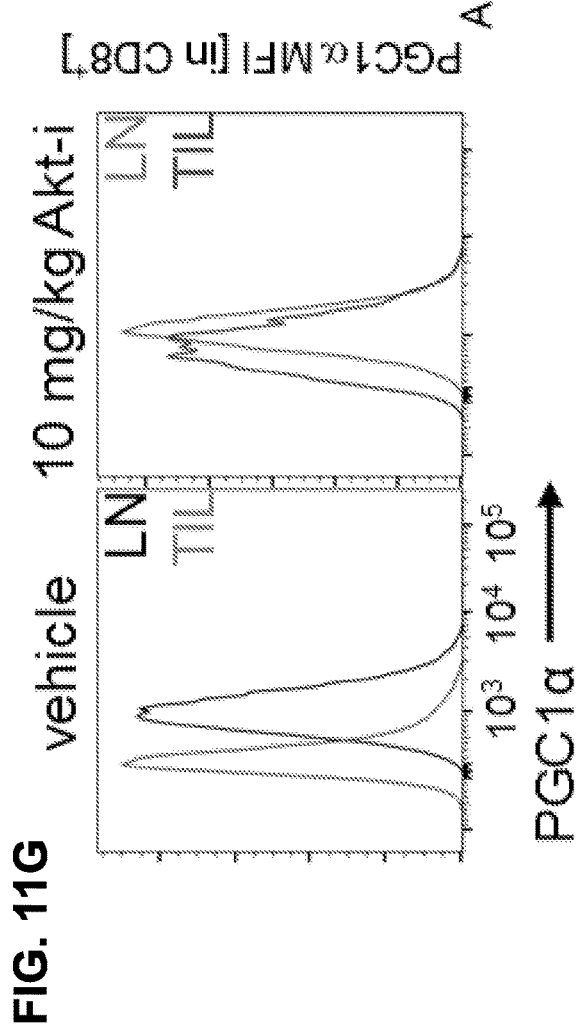
Figure 11H:
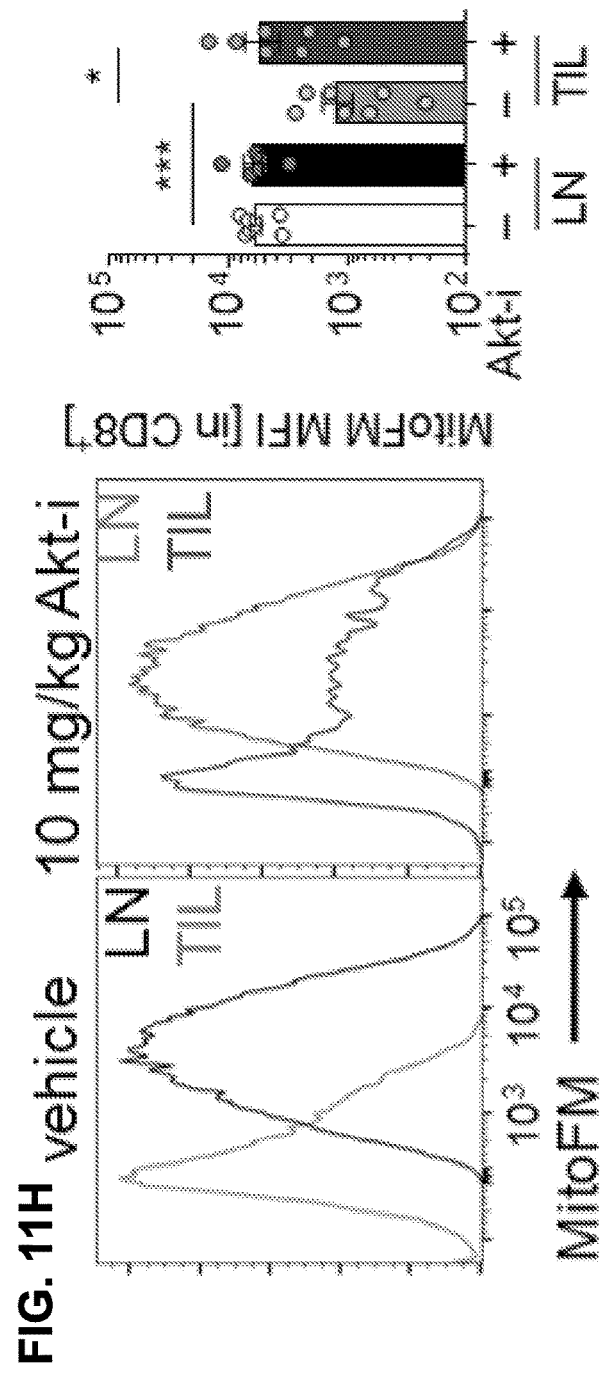

Early (3 d) and late (6 d) responses of T cells responding to B16$^{OVA}$ or VV$^{OVA}$ were examined, and it was observed that while Akt activation in acute viral infection is transient, T cells activated in the tumor microenvironment appear to show chronic Akt signaling, persisting 6 days after adoptive transfer (FIG. 11F). Short-term treatment (72 h) of B16-bearing mice with a potent Akt kinase inhibitor revealed the Akt, in part, mediates losses in PGC1α and mitochondrial sufficiency, such that treatment with Akt inhibitor results in partial rescue of the metabolically suppressive phenotype (FIGS. 11G, 11H).

Thus, T cells responding in tumor microenvironments repress mitochondrial biogenesis through repression of PGC1α, driven, in part, by chronic Akt activation and consequent repression of Foxo activity.

Example 8

Metabolic Reprogramming of Tumor-Specific T Cells Results in Increased Antitumor Immunity Having demonstrated that PGC1α acts as a key node of dysregulation for mitochondrial sufficiency in tumor-specific T cells, it was determined whether reprogramming T cells to favor mitochondrial biogenesis would result in increased intratumoral T cell persistence and function. To this end, retroviral vectors were used to overexpress PGC1α and transduced OT-I T cells. PGC1α overexpression significantly increased mitochondrial levels early (48 and 96 h) after transduction in in vitro culture, although during the expansion phase, empty-vector expressing cells initiate mitochondrial biogenesis and eventually reach mitochondrial levels equivalent to their reprogrammed counterparts (FIG. 13A); however, even at this later stage, PGC1α-reprogrammed T cells show significantly increased OXPHOS (FIG. 13A).

Figure 14A:
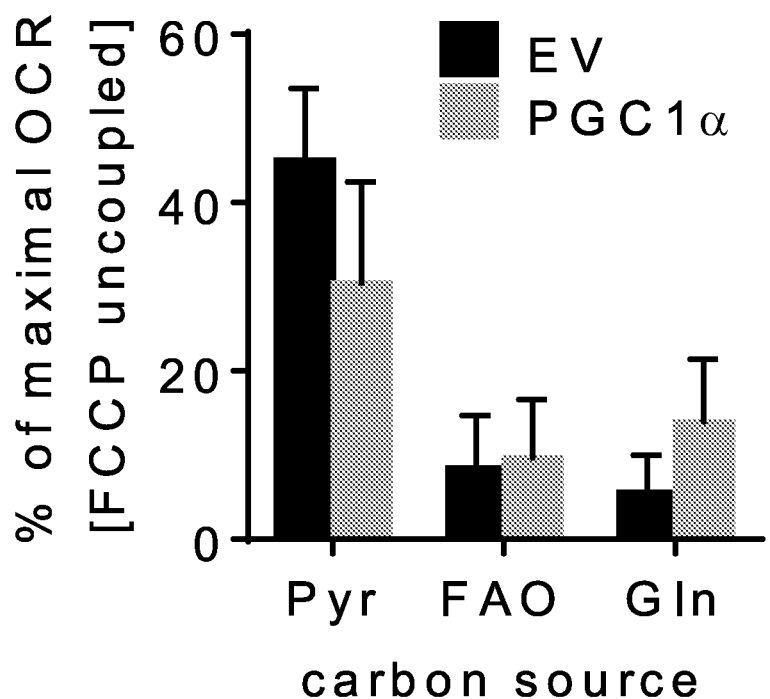
FIGS. 14A-14C. Enforced PGC1α expression results in general increases in mitochondrial function. (A) Fuel usage test of PGC1α- or EV-expressing OT-I T cells. Cells were uncoupled with FCCP and then subjected to sequential inhibition of pyruvate oxidation (UK5099), fatty acid oxidation (etomoxir), and glutaminolysis (BPTES). Results are displayed as % of FCCP-uncoupled OCR sensitive to the appropriate inhibitor. (B) IFNγ and TNFα production of EV or PGC1α expressing T cells prior to adoptive transfer. (C) Expression of PD-1 and LAG-3 on LN or TIL-resident reprogrammed T cells. Results represent the mean of three (A, B) or are representative of five (C) independent experiments. Error bars indicate s.e.m.
Figure 14B:
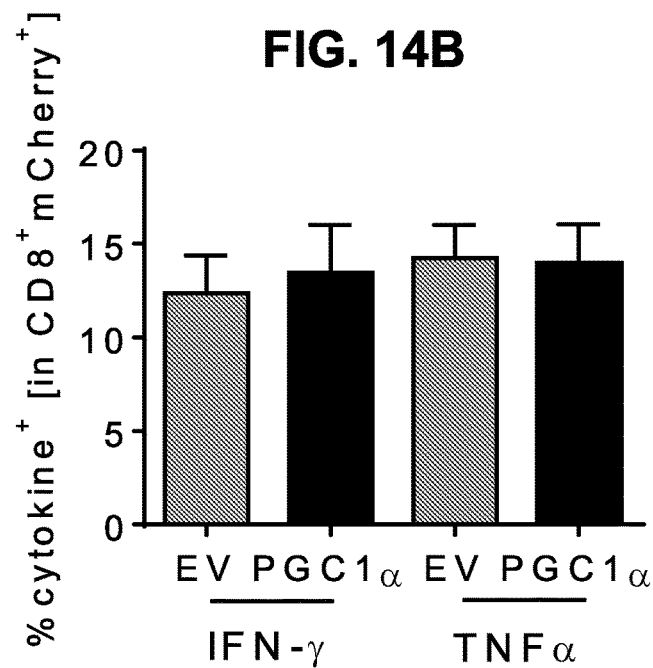

In addition, PGC1α-overexpressing T cells showed a significant upregulation of spare respiratory capacity (FIG. 13A), indicating high mitochondrial reserve and that mitochondrial biogenesis was primed in these reprogrammed cells. No significant increases in aerobic glycolysis (ECAR) was observed in these cells, although a trend was observed in some experiments (FIG. 13A). It was determined if any particular carbon source dominated this increase in SRC. FCCP-uncoupled T cells were treated with inhibitors of pyruvate, fatty acid, or glutamine oxidation, revealing that the increased respiratory capacity did not preferentially apply to a particular carbon source, suggesting that mitochondrial capacity was improved generally when PGC1α expression was enforced (FIG. 14A). In vitro, these T cells exhibit similar effector function as their control counterparts, suggesting that in this environment where nutrients are not limiting, T cells are operating more or less at maximal capacity (FIG. 14B).

Figure 13B:
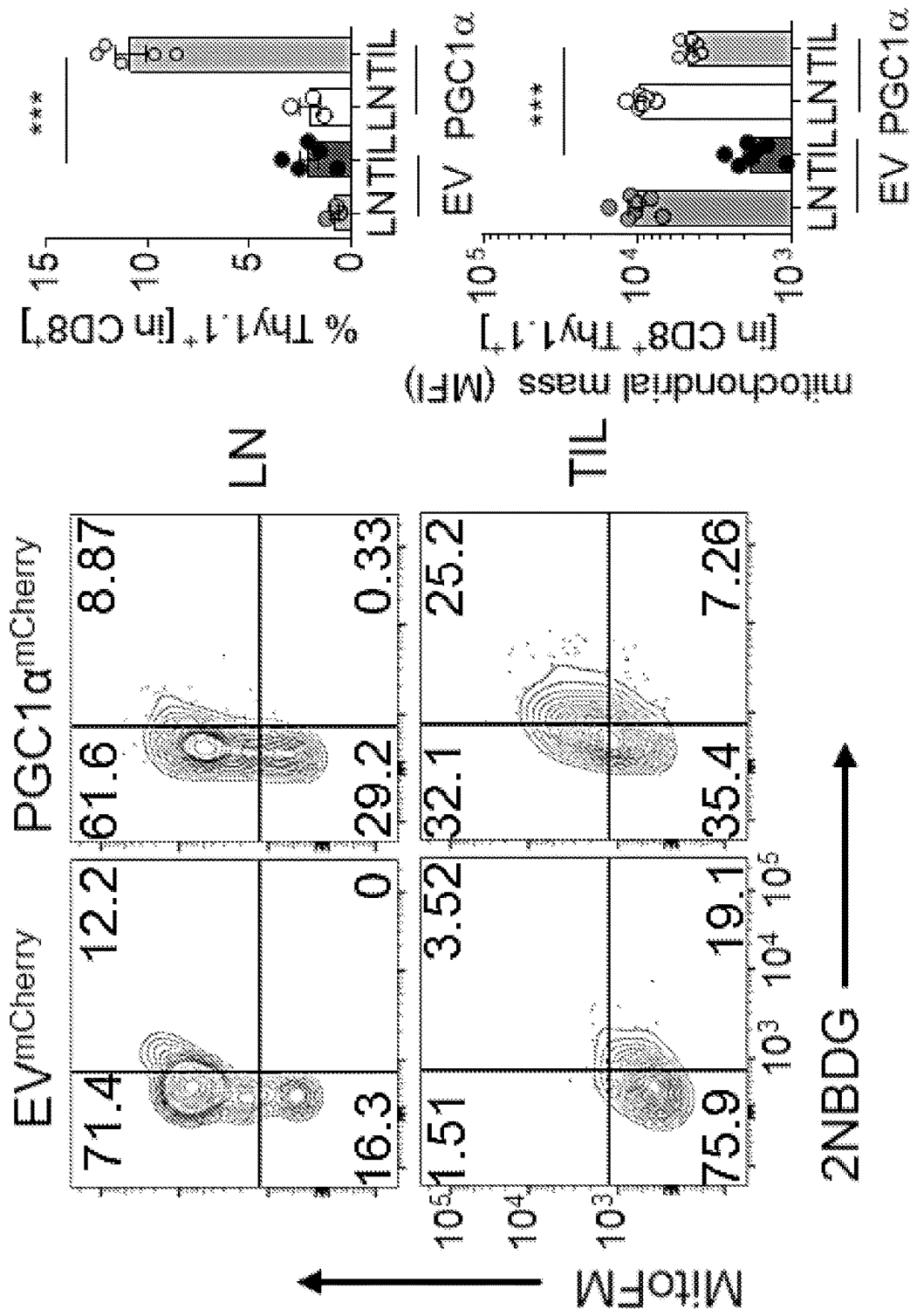
Figure 13C:
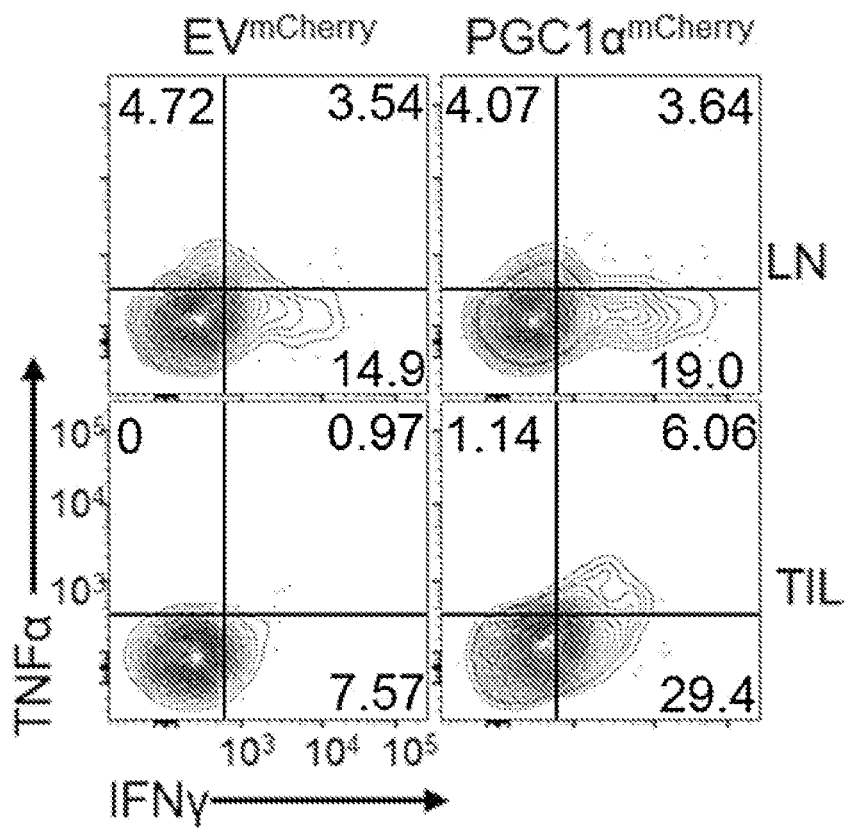
Figure 14C:
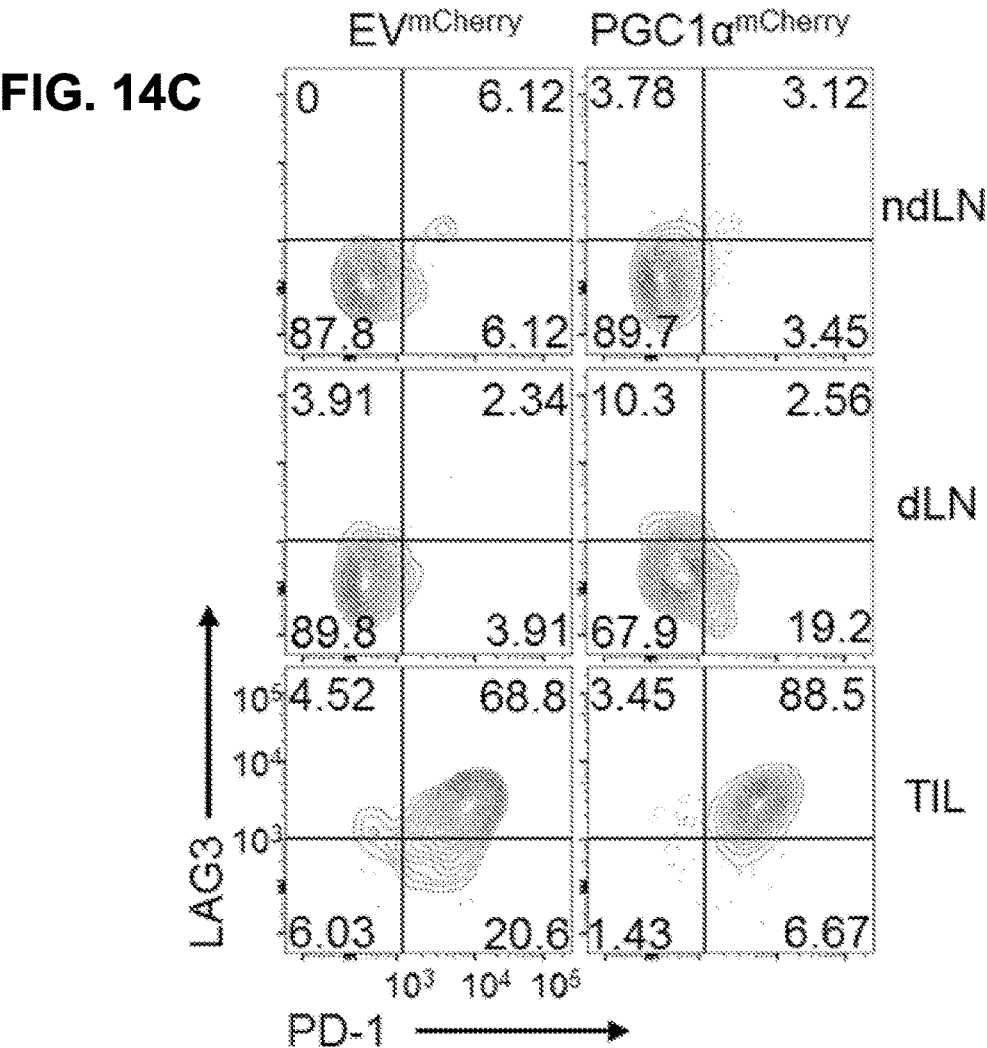

OT-I T cells overexpressing PGC1α transferred into mice with established B16$^{OVA}$ tumors were resistant to loss of mitochondrial sufficiency and highly enriched in the tumor microenvironment (FIG. 13B). Restimulation with OVA peptide showed that these metabolically reprogrammed T cells were superior at producing type 1 cytokines, compared to their wild-type counterparts (FIG. 13C). Notably, these reprogrammed T cells expressed (at even higher levels than EV) co-inhibitory molecules, suggesting retention of mitochondrial function promoted further activation and upregulation of these checkpoint molecules (FIG. 14C).

Having observed that PGC1α-reprogrammed T cells display increased effector function, it was determined whether these T cells had better therapeutic efficacy. Mice bearing small (2-6 mm$^2$) B16$^{OVA}$ tumors received an adoptive transfer of 250,000 (if tumor was <4 mm$^2$) or 500,000 (if starting tumor was >4 mm$^2$) PGC1α or empty-vector transduced OT-I T cells, and tumor growth was measured over time. PGC1α-reprogrammed T cells show enhanced antitumor efficacy resulting in significantly prolonged survival a higher incidence of complete regressions (20%) in this highly aggressive tumor model (FIGS. 13D, 13E).

Thus, reprogramming tumor-specific T cells to favor mitochondrial biogenesis protects them from the loss of function observed in the tumor microenvironment.

REFERENCES

Alvarez-Guardia et al., (2010). The p65 subunit of NF-kappaB binds to PGC-1alpha, linking inflammation and metabolic disturbances in cardiac cells. Cardiovascular research 87, 449-458.

Borniquel, et al., (2010). Inactivation of Foxo3a and subsequent downregulation of PGC-1 alpha mediate nitric oxide-induced endothelial cell migration. Molecular and cellular biology 30, 4035-4044.

Chang et al., (2015). Metabolic Competition in the Tumor Microenvironment Is a Driver of Cancer Progression. Cell 162, 1229-1241.

Cottet-Rousselle et al., (2011). Cytometric assessment of mitochondria using fluorescent probes. Cytometry Part A 79A, 405-425.

Crespo et al., (2013). T cell anergy, exhaustion, senescence, and stemness in the tumor microenvironment. Current opinion in immunology 25, 214-221.

Crompton et al. (2015). Akt inhibition enhances expansion of potent tumor-specific lymphocytes with memory cell characteristics. Cancer research 75, 296-305.

Cui et al., (2010). Perturbations in mitochondrial dynamics induced by human mutant PINK1 can be rescued by the mitochondrial division inhibitor mdivi-1. The Journal of biological chemistry 285, 11740-11752.

Delgoffe, G. M., and Powell, J. D. (2015). Feeding an army: The metabolism of T cells in activation, anergy, and exhaustion. Molecular immunology.

Fernandez-Marcos and Auwerx (2011). Regulation of PGC-1α, a nodal regulator of mitochondrial biogenesis. Am. J. Clin. Nut. 93, 884S-890S.

Finck and Kelly (2006). PGC-1 coactivators: inducible regulators of energy metabolism in health and disease. Journal of Clinical Investigation 116, 615-622.

Haghikia et al. (2015). Interferon-beta affects mitochondrial activity in CD4+ lymphocytes: Implications for mechanism of action in multiple sclerosis. Multiple sclerosis (Houndmills, Basingstoke, England) 21, 1262-1270.

Ho et al., (2015). Phosphoenolpyruvate Is a Metabolic Checkpoint of Anti-tumor T Cell Responses. Cell 162, 1217-1228.

Jiang, et al., (2015). T-cell exhaustion in the tumor microenvironment. Cell death & disease 6, e1792.

Kauppinen et al., (2013). Antagonistic crosstalk between NF-kappaB and SIRT1 in the regulation of inflammation and metabolic disorders. Cellular signalling 25, 1939-1948.

Kim et al., (2007a). Regulatory T cells prevent catastrophic autoimmunity throughout the lifespan of mice. Nature immunology 8, 191-197.

Kim, et al., (2007b). Tumor necrosis factor and interleukin 1 decrease RXRalpha, PPARalpha, PPARgamma, LXRalpha, and the coactivators SRC-1, PGC-1alpha, and PGC-1beta in liver cells. Metabolism: clinical and experimental 56, 267-279.

La-Beck et al., (2015). Immune Checkpoint Inhibitors: New Insights and Current Place in Cancer Therapy. Pharmacotherapy 35, 963-976.

Legat et al., (2013). Inhibitory Receptor Expression Depends More Dominantly on Differentiation and Activation than "Exhaustion" of Human CD8 T Cells. Frontiers in immunology 4, 455.

Li et al., (2013). Caveolae-dependent and -independent uptake of albumin in cultured rodent pulmonary endothelial cells. PloS one 8, e81903.

Liu et al., (2016). Targeting Regulatory T Cells in Tumors. FEBS J 283:2731-48.

Macintyre et al., (2011). Protein kinase B controls transcriptional programs that direct cytotoxic T cell fate but is dispensable for T cell metabolism. Immunity 34, 224-236.

Mahoney et al., (2015). Combination cancer immunotherapy and new immunomodulatory targets. Nature reviews. Drug discovery 14, 561-584.

Monsalve et al., (2000). Direct coupling of transcription and mRNA processing through the thermogenic coactivator PGC-1. Molecular cell 6, 307-316.

Odorizzi et al., (2015). Genetic absence of PD-1 promotes accumulation of terminally differentiated exhausted CD8+ T cells. J. Exp. Med. 212, 1125-1137.

Olmos et al., (2009). Mutual dependence of Foxo3a and PGC-1alpha in the induction of oxidative stress genes. J. Biol. Chem. 284, 14476-14484.

Palomer et al., (2009). TNF-alpha reduces PGC-1alpha expression through NF-kappaB and p38 MAPK leading to increased glucose oxidation in a human cardiac cell model. Cardiovascular research 81, 703-712.

Pauken and Wherry (2015). Overcoming T cell exhaustion in infection and cancer. Trends in immunology 36, 265-276.

Pearce et al., (2013). Fueling immunity: insights into metabolism and lymphocyte function. Science (New York, N.Y.) 342, 1242454.

Pollizzi et al., (2015). mTORC1 and mTORC2 selectively regulate CD8(+) T cell differentiation. The Journal of clinical investigation 125, 2090-2108.

Ribas, A. (2015). Adaptive Immune Resistance: How Cancer Protects from Immune Attack. Cancer discovery 5, 915-919.

Rizzuto et al., (2012). Mitochondria as sensors and regulators of calcium signalling. Nature reviews. Molecular cell biology 13, 566-578.

Roos and Loos. (1970). Changes in the carbohydrate metabolism of mitogenically stimulated human peripheral lymphocytes. I. Stimulation by phytohaemagglutinin. Biochimica et biophysica acta 222, 565-582.

Scarpulla, R. C. (2011). Metabolic control of mitochondrial biogenesis through the PGC-1 family regulatory network. Biochimica et Biophysica Acta (BBA)—Molecular Cell Research 1813, 1269-1278.

Schietinger and Greenberg (2014). Tolerance and exhaustion: defining mechanisms of T cell dysfunction. Trends in immunology 35, 51-60.

Siska and Rathmell (2015). T cell metabolic fitness in antitumor immunity. Trends in immunology 36, 257-264.

Spiegelman (2007). Transcriptional control of energy homeostasis through the PGC1 coactivators. Novartis Foundation symposium 286, 3-6; discussion 6-12, 162-163, 196-203.

Staron et al., (2014). The transcription factor FoxO1 sustains expression of the inhibitory receptor PD-1 and survival of antiviral CD8(+) T cells during chronic infection Immunity 41, 802-814.

Sukumar et al., (2016). Mitochondrial Membrane Potential Identifies Cells with Enhanced Stemness for Cellular Therapy. Cell metabolism 23, 63-76.

van der Windt et al., (2012). Mitochondrial respiratory capacity is a critical regulator of CD8+ T cell memory development. Immunity 36, 68-78.

van der Windt et al., (2013). CD8 memory T cells have a bioenergetic advantage that underlies their rapid recall ability. Proceedings of the National Academy of Sciences of the United States of America 110, 14336-14341.

Wenner (2012). Targeting mitochondria as a therapeutic target in cancer. Journal of cellular physiology 227, 450-456.

Wherry and Kurachi (2015). Molecular and cellular insights into T cell exhaustion. Nature reviews. Immunology 15, 486-499.

Woo et al., (2012) Immune inhibitory molecules LAG-3 and PD-1 synergistically regulate T-cell function to promote tumoral immune escape. Cancer research 72, 917-927.

Xiao et al., (2016). Flow Cytometry-Based Assessment of Mitophagy Using MitoTracker. Frontiers in Cellular Neuroscience 10, 76.

Zhao et al., (2015). Cancer mediates effector T cell dysfunction by targeting microRNAs and EZH2 via glycolysis restriction. Nature immunology.

In view of the many possible embodiments to which the principles of the disclosure may be applied, it should be recognized that the illustrated embodiments are only examples of the disclosure and should not be taken as limiting the scope of the invention. Rather, the scope of the invention is defined by the following claims. I therefore claim as my invention all that comes within the scope and spirit of these claims.

I claim:

1. A recombinant T cell, comprising:
 a vector encoding a variant peroxisome proliferator-activated receptor (PPAR) gamma coactivator 1-alpha (PGC1α),
 wherein the variant PGC1α comprises at least 95% sequence identity to SEQ ID NO: 6 or 9 and comprises at least one serine to alanine substitution, and
 wherein the at least one serine to alanine substitution comprises S576A of SEQ ID NO: 6 or S571A of SEQ ID NO: 9 and increases resistance to negative regulation.

2. The recombinant T cell of claim 1, wherein the recombinant T cell further comprises a chimeric antigen receptor (CAR).

3. The recombinant T cell of claim 1, wherein the recombinant T cell further comprises a recombinant T cell receptor (TCR).

4. The recombinant T cell of claim 1, wherein the vector is a viral vector.

5. The recombinant T cell of claim 4, wherein the viral vector is a lentiviral vector or a retroviral vector.

6. A method of generating the recombinant T cell of claim 1, comprising:
 introducing the vector encoding the variant PGC1α into a T cell, thereby generating the recombinant T cell.

7. The method of claim 6, wherein the T cell is obtained from a subject having cancer, or from a donor subject.

8. The method of claim 6, wherein the method further comprises incubating the recombinant T cell with interleukin 2 (IL-2), IL-7, and/or IL-15.

9. A method of treating a tumor in a subject, comprising:
 administering an effective amount of the recombinant T cell of claim 1 to the subject, thereby treating the tumor.

10. The method of claim 9, further comprising administering an effective amount of chemotherapy, radiation therapy, biologic therapy, or combinations thereof.

11. The method of claim 9, wherein treating the tumor comprises reducing the volume or weight of the tumor, reducing the number of metastases, reducing the size or weight of a metastasis, or combinations thereof.

12. The method of claim 9, wherein the tumor is a leukemia, colorectal cancer, melanoma, cervical cancer, lung cancer, ovarian cancer, bladder cancer, breast cancer, or head and neck cancer.

13. The method of claim 9, further comprising administering an effective amount of IL-2 to the subject before, after, or both before and after, administering the recombinant T cell.

14. The method of claim 9, wherein the subject is administered an effective amount of nonmyeloablative chemotherapy or radiotherapy to deplete native lymphocytes prior to administering an effective amount of the recombinant T cell.

15. A composition, comprising:
 the recombinant T cell of claim 1; and
 a pharmaceutically acceptable carrier.

16. A kit, comprising:
 the composition of claim 15; and
 one or more of a transfection reagent, culture medium, antibiotic, IL-2, IL-7, IL-15, anti-CD28, and anti-CD3.

17. The recombinant T cell of claim 1, wherein the at least one serine to alanine substitution comprises S571A of SEQ ID NO: 9.

18. The recombinant T cell of claim 1, wherein the at least one serine to alanine substitution comprises S576A of SEQ ID NO: 6.

19. The recombinant T cell of claim 1, wherein the recombinant T cell further comprises a chimeric antigen receptor (CAR) or recombinant T cell receptor (TCR).

20. A recombinant vector, comprising:
 a nucleic acid molecule encoding a variant PGC1α, wherein the variant PGC1α comprises at least 95% sequence identity to SEQ ID NO: 6 or 9 and comprises at least one serine to alanine substitution, wherein the at least one serine to alanine substitution comprises S576A of SEQ ID NO: 6 or S571A of SEQ ID NO: 9 and confers resistance to negative regulation; and
 a nucleic acid molecule encoding a chimeric antigen receptor (CAR) or a nucleic acid molecule encoding a recombinant T cell receptor (TCR).

* * * * *